US010544402B2

(12) United States Patent
Nazor et al.

(10) Patent No.: US 10,544,402 B2
(45) Date of Patent: *Jan. 28, 2020

(54) BIOCATALYSTS AND METHODS FOR SYNTHESIZING DERIVATIVES OF TRYPTAMINE AND TRYPTAMINE ANALOGS

(71) Applicant: Codexis, Inc., Redwood City, CA (US)

(72) Inventors: Jovana Nazor, Santa Clara, CA (US); Derek J. Smith, Singapore (SG); Michael A. Crowe, Singapore (SG); Shiwei Song, Singapore (SG); Steven J. Collier, Concord, MA (US)

(73) Assignee: Codexis Inc., Redwood City, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 15/623,698

(22) Filed: Jun. 15, 2017

(65) Prior Publication Data

US 2017/0283781 A1 Oct. 5, 2017

Related U.S. Application Data

(60) Continuation of application No. 15/180,355, filed on Jun. 13, 2016, now Pat. No. 9,708,588, which is a division of application No. 14/828,839, filed on Aug. 18, 2015, now Pat. No. 9,388,395, which is a division of application No. 14/386,082, filed as application No. PCT/US2013/033456 on Mar. 22, 2013, now Pat. No. 9,139,821.

(60) Provisional application No. 61/614,666, filed on Mar. 23, 2012.

(51) Int. Cl.

| | |
|---|---|
| ***C12N 9/10*** | (2006.01) |
| ***C12N 9/06*** | (2006.01) |
| ***C12N 15/00*** | (2006.01) |
| ***C12P 17/10*** | (2006.01) |

(52) U.S. Cl.

CPC ............ *C12N 9/1096* (2013.01); *C12P 17/10* (2013.01); *C12Y 206/01* (2013.01); *C12Y 206/01018* (2013.01); *Y02P 20/52* (2015.11)

(58) Field of Classification Search

CPC ...... C12N 9/1096; C12N 15/62; C12N 15/70; C12Y 206/01; C12P 13/005

USPC ........ 435/128, 193, 320.1, 252.33, 121, 122

See application file for complete search history.

(56) References Cited

U.S. PATENT DOCUMENTS

| | | |
|---|---|---|
| 6,117,679 A | 9/2000 | Stemmer |
| 6,376,246 B1 | 4/2002 | Crameri et al. |
| 6,537,746 B2 | 3/2003 | Arnold et al. |
| 6,586,182 B1 | 7/2003 | Patten et al. |
| 9,139,821 B2 | 9/2015 | Nazor et al. |
| 9,388,395 B2 | 7/2016 | Nazor et al. |
| 2006/0195947 A1 | 8/2006 | Davis et al. |
| 2008/0213845 A1 | 9/2008 | Fotheringham et al. |
| 2008/0220990 A1 | 9/2008 | Fox |
| 2009/0312196 A1 | 12/2009 | Colbeck et al. |
| 2010/0173824 A1 | 7/2010 | Busch et al. |
| 2010/0209981 A1 | 8/2010 | Dhawan et al. |
| 2010/0240897 A1 | 9/2010 | Hinze et al. |

FOREIGN PATENT DOCUMENTS

| | | |
|---|---|---|
| WO | 95/22625 A1 | 8/1995 |
| WO | 95/33836 A1 | 12/1995 |
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 2000/42651 A1 | 7/2000 |
| WO | 2001/75767 A2 | 10/2001 |
| WO | 2009/008908 A2 | 1/2009 |
| WO | 2009/132921 A1 | 11/2009 |
| WO | 2010/081053 A2 | 7/2010 |
| WO | 2011/159910 A2 | 12/2011 |

OTHER PUBLICATIONS

Altschul, S., et al., "Basic local alignment search tool," J. Mol. Biol., 215: 403-410 (1990).

Altschul, S.F., et al., "Gapped BLAST and PSI-BLAST: a new generation of protein database search programs," Nucleic Acids Res., 25(17):3389-3402 (1997).

Baldino, Jr., F., et al., "High-Resolution in Situ Hybridization Histochemistry," Methods Enzymology, 168:761-777 (1989).

Batzer, M.A., "Erratum: Structure and variability of recently inserted Alu family members", Nucleic Acids Res 19:698-699 [1991].

Beaucage, S.L., et al., "Deoxynucleoside phosphoamidites—A new class of key intermediates for deoxypolynucleotide synthesis," Tetrahedron Letters, 22(20):1859-62 (1981).

Black, M.E., et al., "Creation of drug-specific herpes simplex virus type 1 thymidine kinase mutants for gene therapy," Proc Natl Acad Sci USA, 93:3525-3529 (1996).

Bolton, E.T., et al., "A General Method for the lisolation of RNA Complementary to DNA," Proc. Natl. Acad. Sci. USA 48:1390 (1962).

Botstein, D., et al., "Strategies and applications of in vitro mutagenesis," Science, 229(4719):1193-1201, 1985.

Breslauer, K.J., et al., "Predicting DNA duplex stability from the base sequence," Proc. Natl. Acad. Sci. USA, 33:3746-3750 (1986).

Caldwell, R.C., et al., "Mutagenic PCR," PCR Methods Appl., 3:S136-S140 (1994).

(Continued)

*Primary Examiner* — Robert B Mondesi
*Assistant Examiner* — Mohammad Y Meah
(74) *Attorney, Agent, or Firm* — Codexis Inc.

(57) ABSTRACT

The present disclosure provides engineered transaminase polypeptides for the production of amines, polynucleotides encoding the engineered transaminases, host cells capable of expressing the engineered transaminases, and methods of using the engineered transaminases to prepare compounds useful in the production of active pharmaceutical agents.

5 Claims, No Drawings

Specification includes a Sequence Listing.

(56) References Cited

OTHER PUBLICATIONS

Carey, F., Organic Chemistry, 2nd ed., pp. 328-331 [1992].
Carter, P., "Site-directed mutagenesis," Biochem. J., 237:1-7 (1986).
Cho, B.K., et al., "Redesigning the substrate specificity of omega-aminotransferase for the kinetic resolution of aliphatic chiral amines," Biotechnol Bioeng. 99(2):275-84 [2008].
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Freier, S.M., et al., "Improved free-energy parameters for predictions of RNA duplex stability," Proc. Natl. Acad. Sci USA, 83:9373-9377 (1986).
Guo, Z., et al., "3'-End-Forming Signals of Yeast mRNA," Mol. Cell. Biol., 15(11):5983-5990 [1995].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S.,et al., "Amino acid substitution matrices from protein blocks," Proc. Natl. Acad. Sci., 89:10915-10919 (1992).
Höhne, M., et al., "Biocatalytic Routes to Optically Active Amines," Chem. Cat. Chem., 1(1):42-51 [2009].
Höhne, M., et al., "Efficient Asymmetric Synthesis of Chiral Amines by Combining Transaminase and Pyruvate Decarboxylase", ChemBioChem, 9:363-365 (2008).
Kabalka, G.W., et al., "Selected reductions of conjugated nitroalkenes," Tetrahedron, 46(21):7443-7457 [1990].
Kierzek, R., et al., "Polymer-Supported RNA Synthesis and Its Application to Test the Nearest-Neighbor Model for Duplex Stability," Biochemistry, 25:7840-7846 (1986).
Koszelewski, D., et al., "Asymmetric Synthesis of Optically Pure Pharmacologically Relevant Amines Employing ω-Transaminases", Adv. Synth. Catal., 350:2761-2766 (2008).
Koszelewski, D., et al., "Deracemization of mexiletine biocatalyzed by omega-transaminases," Org. Lett., 11(21):4810-2 (2009).
Koszelewski, D., et al., "Immobilization of omega-transaminases by encapsulation in a sol-gel/celite matrix," Journal of Molecular Catalysis B: Enzymatic, 63: 39-44 (2010).
Kramer, B., et al., "Different base/base mismatches are corrected with different efficiencies by the methyl-directed DNA mismatch-repair system of *E. coli*," Cell, 38(3):879-887, 1984.
Kumar, D., et al., "Synthesis of new indole congeners as promising anti-inflammatory agents," Oriental J Chem., 26 (2):455-466 [2010].
Ling, M., et al., "Approaches to DNA Mutagenesis: An Overview," Anal. Biochem., 254:157-78 (1997).
Martin, A.R., et al., "Characterization of free and immobilized (S)-aminotransferase for acetophenone production," Applied Microbiology and Biotechnology, 76(4):843-851 (2007).
Mateo, C., et al., "Epoxy sepabeads: a novel epoxy support for stabilization of industrial enzymes via very intense multipoint covalent attachment," Biotechnology Progress 18(3):629-634 (2002).
Matthes, H.W.D., et al., "Simultaneous rapid chemical synthesis of over one hundred oligonucleotides on a microscale," EMBO J., 3(4):801-805 (1984).
McInerney, J.O., "GCAU: general codon usage analysis," Bioinformatics, 14(4):372-73, 1998.
Midelfort, K.S., et al., "Redesigning and characterizing the substrate specificity and activity of Vibrio fluvialis aminotransferase for the synthesis of imagabalin," Prot. Eng. Des. Sel., 26:25-33 [2013].
Minshull, J., et al., "Protein evolution by molecular breeding," Curr. Op. Chem. Biol., 3(3):284-290 (1999).
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Pradhan, P.K., et al., "Fe—HCl: An Efficient Reagent for Deprotection of Oximes as well as Selective Oxidative Hydrolysis of Nitroalkenes and Nitroalkanes to Ketones," Synthetic Comm., 35:913-922 [2005].
Romanos, M.A., et al., "Foreign gene expression in yeast: a review," Yeast 8:423-488 [1992].
Rychlik, W., et al., "Optimization of the annealing temperature for DNA amplification in vitro," Nucleic Acids Res, 18(21):6409-6412 (1990).
Seo, J.H., et al., "Necessary and sufficient conditions for the asymmetric synthesis of chiral amines using omega-aminotransferases," Biotech. Bioengin., 108(2):253-263 [2011].
Shin, J.S., et al., "Asymmetric synthesis of chiral amines with omega-transaminase," Biotechnol. Bioeng. 65(2):206-211 [1999].
Shin, J.S., et al., "Comparison of the omega-transaminases from different microorganisms and application to production of chiral amines," Biosci. Biotechnol. Biochem. 65:1782-1788 (2001).
Shin, J.S., et al., "Exploring the active site of amine:pyruvate aminotransferase on the basis of the substrate structure-ractivity relationship: how the enzyme controls substrate specificity and stereoselectivity," J. Org. Chem., 67(9):2848-2853 [2002].
Shin, J.S., et al., "Kinetic resolution of alpha-methylbenzylamine with omicron-transaminase screened from soil microorganisms: application of a biphasic system to overcome product inhibition," Biotechnol. Bioeng. 55(2):348-358 [1997].
Shin, J.S., et al., "Kinetic resolution of chiral amines with omega-transaminase using an enzyme-membrane reactor," Biotechnol Bioeng, 73(3):179-187 [2001].
Shin, J.S., et al., "Purification, characterization, and molecular cloning of a novel amine:pyruvate transaminase from Vibrio fluvialis JS17," Appl. Microbiol. Biotechnol., 61(5-6):463-471 [2003].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Stenico, M., et al., "Codon usage in Caenorhabditis elegans: delineation of translational selection and mutational biases," Nucl. Acids Res. 22(13):2437-46 [1994].
Streitwieser, Jr., A., et al., Introduction to Organic Chemistry, 2nd ed., pp. 169-171 (1981).
Suggs, S.V., et al., "Use of synthetic oligodeoxyribonucleotides for the isolation of specific cloned DNA sequenes," In Developmental Biology Using Purified Genes (Brown et al., eds.), pp. 683-693, Academic Press (1981).
Tiwari, S., et al., "Prediction of probable genes by Fourier analysis of genomic sequences," Comput. Appl. Biosci. 13(3):263-270 [1997].
Truppo, M.D., et al., "Development of an Improved Immobilized CAL-B for the Enzymatic Resolution of a Key Intermediate to Odanacatib," Organic Process Research & Development, 15:1033-1035 (2011).

(56) References Cited

OTHER PUBLICATIONS

Uberbacher, E.C., et al., "Discovering and Understanding Genes in Human DNA Sequence Using GRAIL," Methods Enzymol., 266:259-281 [1996].
Van Ophem, P.W., et al., "Substrate inhibition of D-amino acid transaminase and protection by salts and by reduced nicotinamide adenine dinucleotide: isolation and initial characterization of a pyridoxo intermediate related to inactivation.," Biochemistry 37(9):2879-88 (1998).
Villa-Komaroff, L., et al., "A bacterial clone synthesizing proinsulin," Proc. Natl Acad. Sci. USA, 75:3727-3731 (1978).
Wada, K., et al., "Codon usage tabulated from the GenBank genetic sequence data," Nucl. Acids Res., 20:2111-2118 [1992].
Wells, J.A., et al., "Cassette mutagenesis: an efficient method for generation of multiple mutations at defined sites," Gene, 34:315-323 (1985).
Wetmur, J. G., "DNA Probes: Applications of the Principles of Nucleic Acid Hybridization," Crit Rev Biochem Mol Biol, 26(3/4):227-259 (1991).
Wright, F., "The 'effective number of codons' used in a gene," Gene 87:23-29 [1990].
Yeung, B.K., et al., "Spirotetrahydro beta-carbolines (*spiroindolones*): a new class of potent and orally efficacious compounds for the treatment of malaria," J Med Chem., 53(14):5155-5164 [2010].
Yi, S., et al., "Covalent immobilization of omega-transaminase from Vibrio fluvialis JS17 on chitosan beads," Process Biochemistry 42(5):895-898 (2007).
Yun, H., et al., "Asymmetric synthesis of (S)-alpha-methylbenzylamine by recombinant *Escherichia coli* co-expressing omega-transaminase and acetolactate synthase," Biosci. Biotechnol. Biochem., 72(11):3030-3033 [2008].
Yun, H., et al., "Kinetic resolution of (R,S)-sec-butylamine using omega-transaminase from Vibrio fluvialis JS17 under reduced pressure," Biotechnol. Bioeng., 87:772-778 [2004].
Yun, H., et al., "Use of Enrichment Culture for Directed Evolution of the Vibrio fluvialis JS17 omega-Transaminase, Which Is Resistant to Product Inhibition by Aliphatic Ketones," Appl Environ Micriobiol., 71(8):4220-4224 [2005].
Zhang, J-H., et al., "Directed evolution of a fucosidase from a galactosidase by DNA shuffling and screening ,"Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Zhong, S., et al., "5-Chloro-7-iodo-8-quinolinolatomanganese(III) with the Feature of pH-Regulated Molecular Switches as a Highly Efficient Catalyst for Epoxidation of Olefins with Hydrogen Peroxide," Adv. Synth. Catal., 350:802-807 [2008].
Zhu, D., et al., "Biocatalytic asymmetric amination of carbonyl functional groups—a synthetic biology approach to organic chemistry," Biotechnol J., 4(10):1420-1431 (2009).

BIOCATALYSTS AND METHODS FOR SYNTHESIZING DERIVATIVES OF TRYPTAMINE AND TRYPTAMINE ANALOGS

The present application is a Continuation of co-pending U.S. patent application Ser. No. 15/180,355, filed Jun. 13, 2016, now U.S. Pat. No. 9,708,588 which is a Divisional of U.S. patent application Ser. No. 14/828,839, filed Aug. 18, 2015, now U.S. Pat. No. 9,388,395, which is a Divisional of U.S. patent application Ser. No. 14/386,082, filed Sep. 18, 2014, now U.S. Pat. No. 9,139,821, which is a national stage application filed under 35 USC § 371, and claims priority to international application to PCT International Application No. PCT/US2013/033456, filed Mar. 22, 2013, and U.S. Prov. Appln. Ser. No. 61/614,666, filed on Mar. 23, 2012. The present application hereby incorporates each of these priority applications by reference, in their entireties and for all purposes.

1. TECHNICAL FIELD

The disclosure relates to transaminase biocatalysts and processes using the biocatalysts for the preparation of derivatives of tryptamine and tryptamine analogs.

2. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-105USP1_ST25.txt", a creation date of Mar. 23, 2012, and a size of 457,542 kilobytes. The Sequence Listing filed via EFS-Web is part of the specification and is incorporated in its entirety by reference herein.

3. BACKGROUND

Tryptamine class of compounds have the general core structure

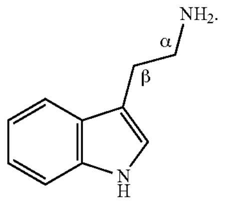 [SMILES: NCCc1c[nH]c2ccccc12]

Derivatives of tryptamine and tryptamine analogs, such as homotryptamine, can have substitutions on the amine, the α-carbon, the β-carbon and the indole ring. Because such derivatives are structurally similar to neurotransmitters serotonin and melatonin, many have psychoactive properties. For example, 5-hydroxy-N,N-dimethyltryptamine, N,N-dimethyltryptamine, 4-hydroxy-N,N-dimethyltryptamine, 5-methoxy-α-methyltryptamine, α-methyltryptamine, and α-ethyltryptamine have psychedelic properties and are regulated in the United States as Schedule 1 Controlled Substances. Tryptamine, tryptamine analogs and their derivatives also form the backbone of many drug compounds, for example hallucinogen lysergic acid diethylamide (LSD), antiplasmodial spiroindolones (Yeung et al., 2010, J Med Chem. 53:5155-5164), noniceptive spirocyclic cyclohexane derivatives (US patent publication No. 20100240897), and farnesoid X receptor antagonist azepinoindole derivatives (US patent publication No. 20100173824).

Tryptamine derivatives with substitutions at the α-carbon, for example α-methyltryptamine or and α-ethyltryptamine, result in a chiral center, and these enantiomers have been shown to display different bioactivity. For example, S-isomer of α-methyltryptamine shows greater potency than the R-isomer (see, e.g., D. B. Repke et al., 1976, J Heterocycl Chem. 13:775). Different isomers of the antiplasmodial spiroindolones, which have chiral α-methyltryptamine or α-methylhomotryptamine components, also show differing potencies, e.g., the (1R, 3S) isomers display higher antiplasmodial activity than the (1R, 3R) isomers (see Yeung, supra; WO2009/132921):

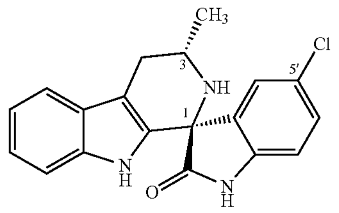

(1R,3S)

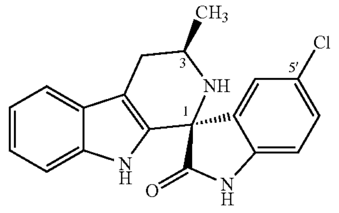

(1R, 3R)

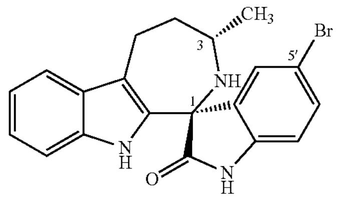

(1R, 3S)

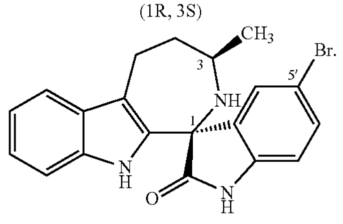

(1R, 3R)

Preparing chiral α-carbon substituted tryptamine and tryptamine analogs, such as α-methyltryptamine and α-methylhomotryptamine, can employ separation/isolation of the desired isomer or use chemical synthetic routes that employ chiral starting compounds for asymmetric synthesis. An illustration of the latter is synthesis of the antimalarial spiroindolines, which can use D-tryptophanol as the starting compound for synthesis of chiral intermediate S-α-methyltryptamine (Yeung et al., supra).

Other general approaches for preparing chiral compounds include reactions with successive achiral reagents that retain chirality, using reagents or the catalyst incorporated with an enantiopure chiral center to convert the enantiomers into diastereomers having different reactivity, use of chemical chiral catalysts, and chiral auxiliary compounds.

Separating and isolating enantiomers can be time consuming while chemical asymmetric synthetic strategies can be restricted by the possible reactions the molecule can undergo, the need for harsh reaction conditions and/or complex synthetic routes. An example is the availability of D-tryptophanol in the synthesis of spiroindolines, which is limiting due the complex synthetic steps required for its synthesis. Thus, it is desirable to develop synthetic methods for preparing α-substituted tryptamines and structurally related analogs that use mild conditions, result in high enantiomeric excess of the desired chiral compound, have high conversion of starting material to desired product, and are cost effective.

4. SUMMARY

The present disclosure provides engineered polypeptides having transaminase activity, polynucleotides encoding the polypeptides, methods of the making the polypeptides, and methods of using the polypeptides for the biocatalytic conversion of ketone substrates to amine products. The present enzymes have been engineered to have one or more residue differences as compared to the amino acid sequence of the naturally occurring transaminase of *Vibrio fluvialis* (SEQ ID NO:2) and a reference engineered transaminase with enhanced solvent and thermal stability (SEQ ID NO:4), where the residue differences occur at residue positions affecting various enzyme properties, including among others, activity, stereoselectivity, stability, expression, and product tolerance. In particular, the transaminases of the present disclosure have been engineered for efficient formation of chiral tryptamine derivatives from its corresponding prochiral ketone substrates. Thus, the engineered polypeptides disclosed herein display, among others, increased activity, solvent and thermal stability, increased product tolerance, and high stereoselectivity in the formation of tryptamine derivatives from the corresponding prochiral ketone substrates, particularly in the conversion of substrate compound (2), 1-(1H-5-fluoro-6-chloro-indol-3-yl)propan-2-one, to product compound (1), (S)-1-(1H-5-fluoro-6-chloro-indol-3-yl)propan-2-amine,

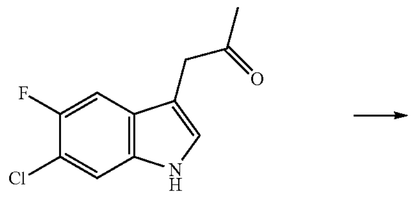

(2)

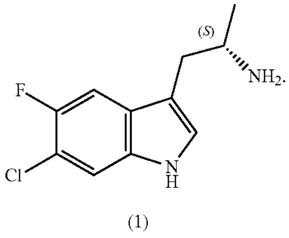

(1)

Accordingly, in one aspect, the present disclosure provides engineered polypeptides having transaminase activity, where the engineered polypeptide comprises an amino acid sequence having at least 80% identity to SEQ ID NO: 2 or 4 and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M.

In some embodiments, the residue differences at the residue positions X14; X26; X33; X41; X47; X70; X88; X107; X132; X148; X173; X203; X250; X284; X31S; X346; X395; X400; X419; X423; X448; and X451 are selected from X14V; X26R; X33T; X41L; X47N; X70A; X88A; X88L; X107P; X132F; X148Q; X148R; X173A; X203S; X250A; X284A; X315G; X346L; X395P; X400G; X419S; X423I; X448E; and X451D.

As provided herein, in some embodiments, the disclosed residue differences can be used singly or in various combinations to generate the engineered polypeptides having the improved enzyme properties. Guidance on the choice of residue differences and effects on enzyme properties are provided in the detailed description herein. In some embodiments, the engineered transaminase polypeptide comprises an amino acid sequence having at least 80% sequence identity to reference sequence SEQ ID NO:4 and at least a residue difference as compared to SEQ ID NO:4 at residue positions selected from X14, X86, X163, or X400. In some embodiments, the amino acid sequence has at least a residue difference at position X163, where the amino acid residues are selected from I, L, R and V.

In some embodiments, the engineered transaminase polypeptide comprises an amino acid sequence having a combination of residue differences as compared to SEQ ID NO:4 selected from: (a) X14V and X163I/L/R/V; (b) X86D and X400G; (c) X57F/Y and X163I/L/R/V; (d) X57F/Y and X398L/V/W; (e) X14V, X113L/V, X163I/L/R/V, X284A, and X424V; and (f) X31S, X57F/Y, X163I/L/R/V, X315G, X346L, and X398L/V/W.

In some embodiments, the engineered transaminase polypeptide comprises an amino acid sequence having a combination of residue differences as compared to SEQ ID NO:4 selected from: (a) X14V, X113L, X163L, X284A, and X424V; (b) X14V, X26R, X163L, X284A, and X400G; (c) X14V, X26R, X88L, and X113L; (d) X57F, X163L, X168K, X314N, X315G, X346L, and X398V; (e) X14V, X163L, X173A, X400G, and X420N; (f) X14V, X113L, X163L, and X284A; (g) X14V, X26R, X163L, X284A, and X400G; and (h) X14V, X33T, X57F, X113L, and X163L.

In some embodiments, the engineered transaminase polypeptide is capable of converting substrate compound (2), 1-(1H-5-fluoro-6-chloro-indol-3-yl)propan-2-one, to product compound (1), (S)-1-(1H-5-fluoro-6-chloro-indol-3-yl)propan-2-amine, in at least 90% enantiomeric excess under suitable reaction conditions.

In some embodiments, the engineered transaminase polypeptide has at least 1.2 fold the activity of SEQ ID NO:4 in converting substrate compound (2) to product compound (1), wherein the amino acid sequence comprises one or more residue differences selected from: X14V, X26R; X31S; X33T; X41L; X70A; X86D; X88A/L; X163I/L; X284A; and X419S. In some embodiments, the engineered transaminase polypeptide has at least 5 fold the activity of SEQ ID NO:4 in converting substrate compound (2) to product compound (1), wherein the amino acid sequence comprises one or more residue differences selected from: X14V, X26R; X33T; X88A/L; X163I/L; and X284A.

In some embodiments, the engineered transaminase polypeptide has at least 1.2 fold increased refractoriness to product compound (1) inhibition as compared to SEQ ID NO:4 in the conversion of substrate compound (2) to product compound (1), under suitable reaction conditions, wherein the amino acid sequence comprises one or more residue differences selected from: X26R; X70A; X86D; X88A/L; X132F; X163L; X315G; X395P; X398L; and X419S. In some embodiments, the engineered transaminase polypeptide has at least 5 fold increased refractoriness to product compound (1) inhibition as compared to SEQ ID NO:4 in the conversion of substrate compound (2) to product compound (1), under suitable reaction conditions, wherein the amino acid sequence comprises one or more residue differences selected from: X26R; X88L; and X163L.

In some embodiments, the engineered transaminase polypeptides can have additional residue differences at other residue positions. In some embodiments, the engineered transaminases can have 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 additional residue differences as compared to SEQ ID NO:2 or 4. In some embodiments, the engineered transaminases can have 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 additional residue differences. In some embodiments, the amino acid sequence has additionally 1, 2, 3, 4, 5, 6, 7, 8, 9, 10, 11, 12, 13, 14, 15, 16, 18, 20, 21, 22, 23, 24, or 25 residue differences as compared to SEQ ID NO: 2 or 4.

Exemplary engineered polypeptides incorporating the residue differences, including various combinations thereof, and having improved properties (e.g., capable of converting compound (2) to compound (1) in at least 90% enantiomeric excess under suitable reaction conditions) are disclosed in Tables 2A and 2B, and the Examples. The amino acid sequences are provided in the Sequence Listing and include SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154.

In another aspect, the present disclosure provides polynucleotides encoding the engineered polypeptides having transaminase activity, as well as expression vectors comprising the polynucleotides, and host cells capable of expressing the polynucleotides encoding the engineered polypeptides. Exemplary polynucleotide sequences are provided in the Sequence Listing incorporated by reference herein and include SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, and 153.

In some embodiments, the present disclosure also provides methods of manufacturing the engineered transaminase polypeptides, where the method can comprise culturing a host cell capable of expressing a polynucleotide encoding the engineered transaminase polypeptide under conditions suitable for expression of the polypeptide. In some embodiments, the method for manufacturing the engineered transaminase polypeptide can also include: (a) synthesizing a polynucleotide encoding a polypeptide comprising an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154 and having one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M; and (b) expressing the transaminase polypeptide encoded by the polynucleotide. As noted above, the residue differences at residue positions X14; X26; X33; X41; X47; X70; X88; X107; X132; X148; X173; X203; X250; X284; X31S; X346; X395; X400; X419; X423; X448; and X451 can be selected from X14V; X26R; X33T; X41L; X47N; X70A; X88A; X88L; X107P; X132F; X148Q; X148R; X173A; X203S; X250A; X284A; X315G; X346L; X395P; X400G; X419S; X423I; X448E; and X451D. As further provided in the detailed description, additional variations can be incorporated during the synthesis of the polynucleotide to prepare engineered transaminases with corresponding differences in the expressed amino acid sequences.

In another aspect, the engineered transaminase polypeptides can be used in a process for preparing various derivatives of tryptamine and tryptamine analogs, such as substituted homotryptamine, from their corresponding ketone substrates. Accordingly, in some embodiments, the engineered transaminase polypeptides can be used in a process for the conversion of substrate compound of formula (II) to product compound of formula (I), as shown below:

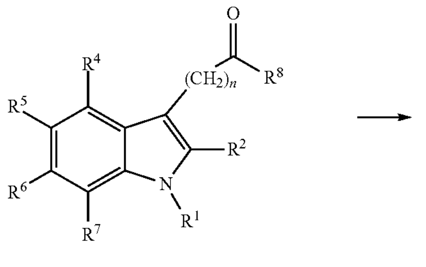

(II)

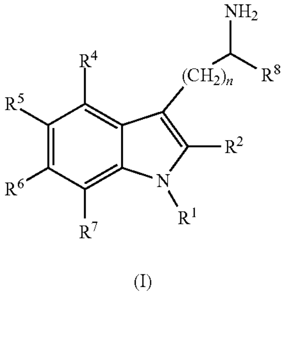

(I)

wherein $R^1$ is selected from the group consisting of hydrogen, carboxy, carboxy($C_1$-$C_6$)alkyl, optionally substituted ($C_1$-$C_6$)alkyl, optionally substituted ($C_2$-$C_6$)alkenyl, optionally substituted alkyloxycarbonyl, optionally substituted arylcarbonyl, optionally substituted arylsulfonyl, and a protecting group;

$R^2$ is selected from the group consisting of hydrogen, oxo, halo, hydroxy, amino, thio, optionally substituted ($C_1$-$C_6$) alkyl, ($C_1$-$C_6$)alkylamino, ($C_1$-$C_6$)dialkylamino, ($C_1$-$C_6$) alkylthio, ($C_1$-$C_6$)alkylsulfonyl, ($C_1$-$C_6$)alkylsulfinyl, and optionally substituted ($C_1$-$C_6$)alkyloxy;

$R^4$, $R^6$ and $R^7$ are each, independently of the others, selected from the group consisting of hydrogen, halo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$) alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl;

$R^5$ is selected from the group consisting of hydrogen, halo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$) alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$) alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl, or together with $R^4$ forms a 5 to 8 membered optionally substituted cycloalkyl or optionally substituted heterocyclic ring;

$R^8$ is selected from the group consisting of optionally substituted ($C_1$-$C_6$) alkyl, optionally substituted ($C_1$-$C_6$) alkyloxy, optionally substituted cycloalkyl, optionally substituted heterocycloalkyl, optionally substituted aryl, and optionally substituted heteroaryl, or together with $R^2$ forms an optionally substituted 5 to 8 membered cycloalkyl or heterocyclic ring; and n is 1 or 2;

with the provisos that (a) when $R^2$ is hydrogen, then at least one of the following applies:

(i) $R^1$ is not hydrogen, methyl, 4-(methyloxy)phenylcarbonyl-, 4-(trifluoromethyloxy)phenylsulfonyl-, 3-bromophenylcarbonyl-, 3-aminopropyl-, or 3-(methylcarbonylamino)propyl-;

(ii) $R^4$ and $R^7$ are each, independently of the other, not hydrogen or chloro;

(iii) $R^5$ is not hydrogen, hydroxy, methyl, methyloxy, fluoro, chloro, trifluoromethyl, or cyano;

(iv) $R^6$ is not hydrogen, hydroxy, methyloxy, fluoro or chloro; or (v) $R^8$ is not methyl, ethyl, hydroxymethyl, or trifluoromethyl-; and (b) when n is 1, $R^2$ and $R^8$ together form a cyclohexyl ring, and $R^1$, $R^4$, $R^6$, and $R^7$ are hydrogen, then $R^5$ is not fluoro.

Accordingly, in some embodiments, a process for preparing the compound of structural formula (I) can comprise contacting the compound of structural formula (II) with any of the engineered transaminases of the present disclosure in presence of an amine donor under suitable reaction conditions.

In some embodiments, the stereoselectivity of the transaminases can be used to prepare the chiral compound of formula (IS), (IS)

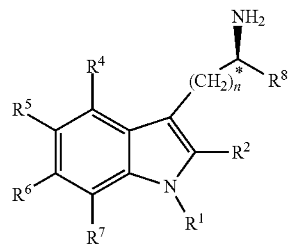

wherein $R^1$, $R^2$, $R^4$, $R^5$, $R^6$, $R^7$, $R^8$ and n are as defined above, and having the indicated stereochemistry at the carbon atom marked with an *, wherein compound of formula (IS) is formed in enantiomeric excess. In some embodiments of the process, the compound of formula (IS) can be formed in at least 90%, 91%, 92%, 93%, 94%, 95%, 96%, 97%, 98%, 99% or greater enantiomeric excess.

In some embodiments, the engineered transaminase polypeptides can be used in a process for the conversion of substrate compounds of formula (IIb) to product compounds of structural formula (Ib), as shown below:

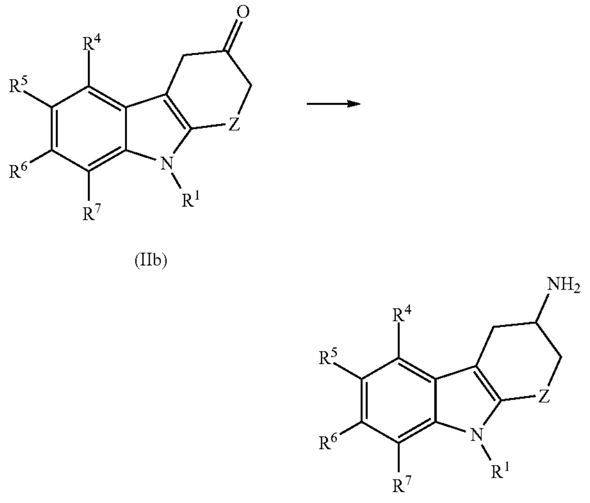

(IIb)

(Ib)

wherein,

Z is selected from the group consisting of O, S, NH, or $—(CH_2)_m—$, wherein m is 0, 1, 2 or 3;

$R^1$ is selected from the group consisting of hydrogen, carboxy, carboxy($C_1$-$C_6$)alkyl, optionally substituted ($C_1$-$C_6$)alkyl, optionally substituted ($C_2$-$C_6$)alkenyl, optionally substituted alkyloxycarbonyl, optionally substituted arylcarbonyl, optionally substituted arylsulfonyl, and a protecting group;

$R^4$, $R^5$, $R^6$ and $R^7$ are each, independently of the others, selected from the group consisting of hydrogen, halo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$) alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted arylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl;

with the proviso that when Z is $—(CH_2)_m—$, m is 1, and $R^1$, $R^4$, $R^6$ and $R^7$ are hydrogen, then $R^5$ is not fluoro.

Accordingly, in some embodiments, a process for preparing the compound of structural formula (Ib) can comprise contacting the compound of structural formula (IIb) with any of the engineered transaminases of the present disclosure in presence of an amine donor under suitable reaction conditions.

In some embodiments, the stereoselectivity of the transaminases can be used to prepare the chiral compound of formula (IbS), (IbS)

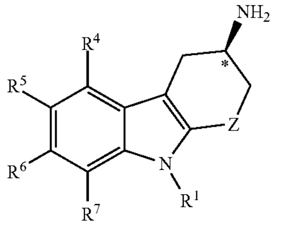

wherein Z, $R^1$, $R^4$, $R^5$, $R^6$, and $R^7$ are as defined above and having the indicated stereochemistry at the carbon atom marked with an *, wherein the compound of formula (IbS) is formed in enantiomeric excess. In some embodiments of the process, the compound of formula (IbS) can be formed in at least 90%, 91%, 92%, 93%, 94%, 95%, 96%, 97%, 98%, 99% or greater enantiomeric excess.

As provided herein, the processes using the engineered transaminases can be done under a range of suitable reaction conditions, including, among others, ranges of amine donor, pH, temperature, buffer, solvent system, substrate loading, polypeptide loading, cofactor loading, pressure, and reaction time.

In some embodiments, the suitable reaction conditions for the transamination process can comprise: (a) substrate loading at about 5 g/L to 200 g/L; (b) about 0.1 to 50 g/L of engineered transaminase polypeptide; (c) about 0.1 to 4 M of isopropylamine (IPM); (d) about 0.1 to 10 g/L of pyridoxal phosphate (PLP) cofactor; (e) pH of about 6 to 9; and (f) temperature of about 30 to 60° C.

In some embodiments, the suitable reaction conditions for the transamination process can comprise: (a) substrate loading at about 5 to about 20 g/L; (b) about 0.05 to 2 g/L of engineered transaminase polypeptide; (c) about 1 to 10% v/v of PEG200; (d) about 1 to 2 M of isopropylamine (IPM); (e) about 0.1 to 1 g/L of pyridoxal phosphate (PLP) cofactor; (f) about 0.1 to about 0.5 M of triethanolamine (TEA); (g) pH of about 6 to 8; and (h) temperature of about 45 to 55° C.

In some embodiments, the suitable reaction conditions for the transamination process can comprise: (a) substrate loading of about 25 to about 100 g/L; (b) about 0.5 to 10 g/L of transaminase polypeptide; (c) about 1 to 10% v/v of PEG200; (d) about 1 to 2 M of isopropylamine (IPM); (e) about 0.1 to 1 g/L of pyridoxal phosphate (PLP) cofactor; (f) about 0.1 to about 0.5 M of triethanolamine; (g) pH of about 6 to 8; and (h) temperature of about 45 to 55° C.

Guidance on the choice of engineered transaminases, preparation of the biocatalysts, the choice of enzyme substrates, and parameters for carrying out the processes are further described in the detailed description that follow.

5. DETAILED DESCRIPTION

As used in this specification and the appended claims, the singular forms "a", "an" and "the" include plural referents unless the context clearly indicates otherwise. Thus, for example, reference to "a polypeptide" includes more than one polypeptide.

Similarly, "comprise," "comprises," "comprising" "include," "includes," and "including" are interchangeable and not intended to be limiting.

It is to be further understood that where descriptions of various embodiments use the term “comprising,” those skilled in the art would understand that in some specific instances, an embodiment can be alternatively described using language “consisting essentially of” or “consisting of.”

It is to be understood that both the foregoing general description, including the drawings, and the following detailed description are exemplary and explanatory only and are not restrictive of this disclosure.

The section headings used herein are for organizational purposes only and not to be construed as limiting the subject matter described.

5.1 Abbreviations

The abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an “L” or a “D” or clear from the context in which the abbreviation is used, the amino acid may be in either the L- or D-configuration about α-carbon ($C_\alpha$). For example, whereas “Ala” designates alanine without specifying the configuration about the α-carbon, “D-Ala” and “L-Ala” designate D-alanine and L-alanine, respectively. When the one-letter abbreviations are used, upper case letters designate amino acids in the L-configuration about the α-carbon and lower case letters designate amino acids in the D-configuration about the α-carbon. For example, “A” designates L-alanine and “a” designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

5.2 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

“Protein”, “polypeptide,” and “peptide” are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

“Polynucleotide” or “nucleic acid” refers to two or more nucleosides that are covalently linked together. The polynucleotide may be wholly comprised ribonucleosides (i.e., an RNA), wholly comprised of 2'-deoxyribonucleotides (i.e., a DNA) or mixtures of ribo- and 2'-deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

“Aminotransferase” and “transaminase” are used interchangeably herein to refer to a polypeptide having an enzymatic capability of transferring an amino group ($NH_2$) from a primary amine to a carbonyl group (C═O) of an acceptor molecule. Transaminases as used herein include naturally occurring (wild-type) transaminases as well as non-naturally occurring engineered polypeptides generated by human manipulation.

“Amino acceptor” and “amine acceptor,” “keto substrate,” “keto,” and “ketone” are used interchangeably herein to refer to a carbonyl (keto, or ketone) compound which accepts an amino group from a donor amine. In some embodiments, amino acceptors are molecules of the following general formula,

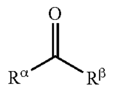

amino acceptor in which each of $R^\alpha$ and $R^\beta$, when taken independently, is an alkyl, cycloalkyl, heterocycloalkyl, aryl, or heteroaryl, which can be unsubstituted or substituted with one or more enzymatically acceptable groups. $R^\alpha$ may be the same or different from $R^\beta$ in structure or chirality. In some embodiments, $R^\alpha$ and $R^\beta$, taken together, may form a ring that is unsubstituted, substituted, or fused to other rings. Amino acceptors include keto carboxylic acids and alkanones (ketones). Typical keto carboxylic acids are α-keto carboxylic acids such as glyoxalic acid, pyruvic acid, oxaloacetic acid, and the like, as well as salts of these acids. Amino acceptors also include substances which are converted to an amino acceptor by other enzymes or whole cell processes, such as fumaric acid (which can be converted to oxaloacetic acid), glucose (which can be converted to pyruvate), lactate, maleic acid, and others. Amino acceptors that can be used include, by way of example and not limitation, 3,4-dihydronaphthalen-1(2H)-one, 1-phenylbutan-2-one, 3,3-dimethylbutan-2-one, octan-2-one, ethyl 3-oxobutanoate, 4-phenylbutan-2-one, 1-(4-bromophenyflethanone, 2-methylcyclohexamone, 7-methoxy-2-tetralone, 1-hydroxybutan-2-one, pyruvic acid, acetophenone, 3'-hydroxyacetophenone, 2-methoxy-5-fluoroacetophenone, levulinic acid, 1-phenylpropan-1-one, 1-(4-bromophenyl)propan-1-one, 1-(4-nitrophenyl)propan-1-one, 1-phenylpropan-2-one, 2-oxo-3-methylbutanoic acid, 1-(3-trifluoromethylphenyl)propan-1-one, hydroxypropanone, methoxyoxypropanone, 1-phenylbutan-1-one, 1-(2,5-dimethoxy-4-methylphenyl) butan-2-one, 1-(4-hydroxyphenyl)butan-3-one, 2-acetylnaphthalene, phenylpyruvic acid, 2-ketoglutaric acid, and 2-ketosuccinic acid, including both (R) and (S) single isomers where possible.

"Amino donor" or "amine donor" refers to an amino compound which donates an amino group to the amino acceptor, thereby becoming a carbonyl species. In some embodiments, amino donors are molecules of the following general formula,

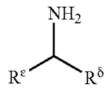

amino donor in which each of $R^{\varepsilon}$ and $R^{\delta}$, when taken independently, is an alkyl, cycloalkyl, heterocycloalkyl, aryl, or heteroaryl, which is unsubstituted or substituted with one or more enzymatically non-inhibiting groups. $R^{\varepsilon}$ can be the same or different from $R^{\delta}$ in structure or chirality. In some embodiments, $R^{\varepsilon}$ and $R^{\delta}$, taken together, may form a ring that is unsubstituted, substituted, or fused to other rings. Typical amino donors that can be used include chiral and achiral amino acids, and chiral and achiral amines. Amino donors that can be used include, by way of example and not limitation, isopropylamine (also referred to as 2-aminopropane), α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-alanine, D-alanine, D,L-alanine, L-aspartic acid, L-lysine, D,L-ornithine, β-alanine, taurine, n-octylamine, cyclohexylamine, 1,4-butanediamine (also referred to as putrescine), 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines.

"Chiral amine" refers to amines of general formula $R^{\alpha}—CH(NH_2)—R^{\beta}$ and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R^{\alpha}$ and $R^{\beta}$ above) also can vary widely and include alkyl, aralkyl, aryl, halo, hydroxy, lower alkyl, lower alkoxy, lower alkylthio, cycloalkyl, carboxy, carbalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Pyridoxal-phosphate," "PLP," "pyridoxal-5'-phosphate," "PYP," and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7]. Pyridoxal-5'-phosphate can be produced in vivo by phosphorylation and oxidation of pyridoxol (also known as Vitamin $B_6$). In transamination reactions using transaminase enzymes, the amine group of the amino donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces an amine and regenerates the coenzyme. In some embodiments, the pyridoxal-5'-phosphate can be replaced by other members of the vitamin $B_6$ family, including pyridoxine (PN), pyridoxal (PL), pyridoxamine (PM), and their phosphorylated counterparts; pyridoxine phosphate (PNP), and pyridoxamine phosphate (PMP).

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO:4 having at the residue corresponding to X14 a valine" or X14V refers to a reference sequence in which the corresponding residue at X14 in SEQ ID NO:4, which is a tyrosine, has been changed to valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered transaminase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X14 as compared to SEQ ID NO: 4" refers to a change of the amino acid residue at the polypeptide position corresponding to position 14 of SEQ ID NO:4. Thus, if the reference polypeptide of SEQ ID NO: 4 has a tyrosine at position 14, then a "residue difference at position X14 as compared to SEQ ID NO:4" an amino acid substitution of any residue other than tyrosine at the position of the polypeptide corresponding to position 14 of SEQ ID NO: 4. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some embodiments, where more than one amino acid can appear in a specified residue position, the alternative amino acids can be listed in the form XnY/Z, where Y and Z represent alternate amino acid residues. In some instances (e.g., in Table 2A and 2B), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. Furthermore, in some instances, a polypeptide of the present disclosure can include one or more amino acid residue differences relative to a reference sequence, which is indicated by a list of the specified positions where changes are made relative to the reference sequence.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below.

TABLE 1

| Residue | Possible Conservative Substitutions |
|---|---|
| A, L, V, I | Other aliphatic (A, L, V, I)<br>Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine), (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered transaminase enzymes comprise insertions of one or more amino acids to the naturally occurring transaminase polypeptide as well as insertions of one or more amino acids to other improved transaminase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the reference polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length transaminase polypeptide, for example the polypeptide of SEQ ID NO:2 or engineered transaminase of SEQ ID NO:34.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved transaminase enzymes may be present within a cell, present in the cellular medium, or prepared in various forms, such as lysates or isolated preparations. As such, in some embodiments, the improved transaminase enzyme can be an isolated polypeptide.

"Substantially pure polypeptide" refers to a composition in which the polypeptide species is the predominant species present (i.e., on a molar or weight basis, it is more abundant than any other individual macromolecular species in the composition), and is generally a substantially purified composition when the object species comprises at least about 50 percent of the macromolecular species present by mole or % weight. Generally, a substantially pure transaminase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved transaminase polypeptide is a substantially pure polypeptide composition.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate, e.g., compound (2), to its corresponding chiral amine product, e.g., compound (1), with at least about 85% stereomeric excess.

"Improved enzyme property" refers to a transaminase polypeptide that exhibits an improvement in any enzyme property as compared to a reference transaminase. For the engineered transaminase polypeptides described herein, the comparison is generally made to the wild-type transaminase enzyme, although in some embodiments, the reference transaminase can be another engineered transaminase. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), and stereoselectivity (including enantioselectivity).

"Increased enzymatic activity" refers to an improved property of the engineered transaminase polypeptides, which can be represented by an increased specific activity (e.g., product produced/time/weight protein) or an increased percent conversion of the substrate to the product (e.g., percent conversion of starting amount of substrate to product in a specified time period using a specified amount of transaminase) as compared to the reference transaminase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.2 fold the enzymatic activity of the corresponding wild-type transaminase enzyme, to as much as 2 fold, 5 fold, 10 fold, 20 fold, 25 fold, 50 fold, 75 fold, 100 fold, or more enzymatic activity than the naturally occurring transaminase or another engineered transaminase from which the transaminase polypeptides were derived. Transaminase activity can be measured by any one of standard assays, such as by monitoring changes in spectrophotometric properties of reactants or products. In some embodiments, the amount of products produced can be measured by High-Performance Liquid Chromatography (HPLC) separation combined with UV absorbance or fluorescent detection following derivatization, such as with o-phthaldialdehyde (OPA). Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a transaminase polypeptide can be expressed as "percent conversion" of the substrate to the product.

"Thermostable" refers to a transaminase polypeptide that maintains similar activity (more than 60% to 80% for example) after exposure to elevated temperatures (e.g., 40-80° C.) for a period of time (e.g., 0.5-24 hrs) compared to the wild-type enzyme.

"Solvent stable" refers to a transaminase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme.

"Thermo- and solvent stable" refers to a transaminase polypeptide that is both thermostable and solvent stable.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad Sci USA 83:8893-8897; Freier et al., 1986, Proc. Natl. Acad Sci USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporated herein by reference). In some embodiments, the polynucleotide encodes the polypeptide disclosed herein and hybridizes under defined conditions, such as moderately stringent or highly stringent conditions, to the complement of a sequence encoding an engineered transaminase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the transaminase enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and Salmonella," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refer to those conditions in the biocatalytic reaction solution (e.g., ranges of enzyme loading, substrate loading, cofactor loading, temperature, pH, buffers, co-solvents, etc.) under which a transaminase polypeptide of the present disclosure is capable of converting a substrate compound to a product compound (e.g., conversion of compound (2) to compound (1)). Exemplary "suitable reaction conditions" are provided in the detailed description and illustrated by the Examples.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an exemplary substrate for the transaminase biocatalyst in the process disclosed herein is compound (2).

"Product" in the context of a biocatalyst mediated process refers to the compound or molecule resulting from the action of the biocatalyst. For example, an exemplary product for the transaminase biocatalyst in the process disclosed herein is compound (1).

"Alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., $(C_1\text{-}C_6)$alkyl refers to an alkyl of 1 to 6 carbon atoms. A lower alkyl refers to $(C_1\text{-}C_6)$alkyl.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Heteroalkyl, "heteroalkenyl," and "heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —$NR^{\gamma}$—, —PH—, —S(O)—, —S(O)2-, —S(O) $NR^{\gamma}$—, —$S(O)_2NR^{\gamma}$—, and the like, including combinations thereof, where each $R^{\gamma}$ is independently selected from hydrogen, alkyl, heteroalkyl, cycloalkyl, heterocycloalkyl, aryl, heteroaryl, and other suitable substituents.

"Aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

"Arylalkyl" refers to an alkyl substituted with an aryl, i.e., aryl-alkyl-groups, preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

"Arylalkenyl" refers to an alkenyl substituted with an aryl, i.e., aryl-alkenyl-groups, preferably having from 2 to 6 carbon atoms inclusively in the alkenyl moiety and from 6 to 12 carbon atoms inclusively in the aryl moiety.

"Arylalkynyl" refers to an alkynyl substituted with an aryl, i.e., aryl-alkynyl-groups, preferably having from 2 to 6 carbon atoms inclusively in the alkynyl moiety and from 6 to 12 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

"Cycloalkylalkyl" refers to an alkyl substituted with a cycloalkyl, i.e., cycloalkyl-alkyl-groups, preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

"Cycloalkylalkenyl" refers to an alkenyl substituted with a cycloalkyl, i.e., cycloalkyl-alkenyl-groups, preferably having from 2 to 6 carbon atoms inclusively in the alkenyl moiety and from 3 to 12 carbon atoms inclusively in the cycloalkyl moiety.

"Cycloalkylalkynyl" refers to an alkynyl substituted with a cycloalkyl, i.e., cycloalkyl-alkynyl-groups, preferably having from 2 to 6 carbon atoms inclusively in the alkynyl moiety and from 3 to 12 carbon atoms inclusively in the cycloalkyl moiety.

"Amino" refers to the group —$NH_2$. Substituted amino refers to the group —$NHR^{\eta}$, $NR^{\eta}R^{\eta}$, and $NR^{\gamma}R^{\gamma}R^{\gamma}$, where each $R^{\gamma}$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylysulfonylamino, furanyl-oxy-sulfamino, and the like.

"Alkylamino" refers to a —$NHR^{\xi}$ group, where $R^{\xi}$ is an alkyl, an N-oxide derivative, or a protected derivative thereof, e.g., methylamino, ethylamino, n-propylamino, iso-propylamino, n-butylamino, iso-butylamino, tert-butylamino, or methylamino-N-oxide, and the like.

"Arylamino" refers to —$NHR^{\lambda}$, where $R^{\lambda}$ is an aryl group, which can be optionally substituted.

"Heteroarylamino" refers to —$NHR^{\sigma}$ where $R^{\sigma}$ is a heteroaryl group, which can be optionally substituted.

"Aminoalkyl" refers to an alkyl group in which one or more of the hydrogen atoms is replaced with an amino group, including a substituted amino group.

"Oxo" refers to =O

"Oxy" refers to a divalent group —O—, which may have various substituents to form different oxy groups, including ethers and esters.

"Alkoxy" or "alkyloxy" are used interchangeably herein to refer to the group —$OR^{\xi}$, wherein $R^{\xi}$ is an alkyl group, including optionally substituted alkyl groups as also defined herein.

"Aryloxy" refers to —$OR^{\lambda}$ groups, where $R^{\lambda}$ is an aryl group, which can be optionally substituted.

"Heteroaryloxy" refers to —$OR^{o}$, where $R^{o}$ is a heteroaryl group, which can be optionally substituted.

"Carboxy" refers to —COOH.

"Carboxyalkyl" refers to an alkyl substituted with a carboxy group.

"Carbonyl" refers to —C(O)—, which may have a variety of substituents to form different carbonyl groups including acids, acid halides, aldehydes, amides, esters, and ketones.

"Alkylcarbonyl" refers to —$C(O)R^{\xi}$, where $R^{\xi}$ is an alkyl group, which can be optionally substituted.

"Arylcarbonyl" refers to —$C(O)R^{\lambda}$, where $R^{\lambda}$ is an aryl group, which can be optionally substituted.

"Heteroarylcarbonyl" refers to —$C(O)R^{o}$ where $R^{o}$ is a heteroaryl group, which can be optionally substituted.

"Alkyloxycarbonyl" refers to —$C(O)OR^{\xi}$, where $R^{\xi}$ is an alkyl group, which can be optionally substituted.

"Aryloxycarbonyl" refers to —$C(O)OR^{\lambda}$, where $R^{\lambda}$ is an aryl group, which can be optionally substituted.

"Heteroaryloxycarbonyl" refers to —$C(O)OR^{o}$, where $R^{o}$ is a heteroaryl group, which can be optionally substituted.

"Arylalkyloxycarbonyl" refers to —$C(O)OR^{\rho}$, where $R^{\rho}$ is an aryl-alkyl-group, which can be optionally substituted.

"Alkylcarbonyloxy" refers to —OC(O)—$R^{\xi}$, where R is an alkyl group, which can be optionally substituted.

"Arylcarbonyloxy" refers to —$OC(O)R^{\lambda}$, where R is an aryl group, which can be optionally substituted.

"Heteroarylalkyloxycarbonyl" refers to —$C(O)OR^{\omega}$, where $R^{\omega}$ is a heteroarylalkyl group, which can be optionally substituted.

"Heteroarylcarbonyloxy" refers to —$OC(O)R^{o}$, where $R^{o}$ is an heteroaryl group, which can be optionally substituted.

"Aminocarbonyl" refers to —$C(O)NH_2$. Substituted aminocarbonyl refers to —$C(O)NR^{\eta}R^{\eta}$, where the amino group $NR^{\eta}R^{\eta}$ is as defined herein.

"Aminocarbonylalkyl" refers to an alkyl substituted with an aminocarbonyl group.

"Halogen" or "halo" refers to fluoro, chloro, bromo and iodo.

"Haloalkyl" refers to an alkyl group substituted with one or more halogen. Thus, the term "haloalkyl" is meant to include monohaloalkyls, dihaloalkyls, trihaloalkyls, etc. up to perhaloalkyls. For example, the expression "($C_1$ $C_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

"Hydroxy" refers to —OH.

"Hydroxyalkyl" refers to an alkyl substituted with one or more hydroxy group.

"Cyano" refers to —CN.

"Nitro" refers to —$NO_2$.

"Thio" or "sulfanyl" refers to —SH. Substituted thio or sulfanyl refers to —S—$R^{\eta}$, where $R^{\eta}$ is an alkyl, aryl or other suitable substituent.

"Alkylthio" refers to —$SR^{\xi}$, where $R^{\xi}$ is an alkyl, which can be optionally substituted. Typical alkylthio group include, but are not limited to, methylthio, ethylthio, n-propylthio, and the like.

"Arylthio" refers to —$SR^{\lambda}$, where $R^{\lambda}$ is an aryl, which can be optionally substituted. Typical arylthio groups include, but are not limited to, phenylthio, (4-methylphenyl) thio, pyridinylthio, and the like.

"Heteroarylthio" refers to —$SR^{o}$, where $R^{o}$ is a heteroaryl, which can be optionally substituted.

"Sulfonyl" refers to —$SO_2$—. Substituted sulfonyl refers to —$SO_2$—$R^{\eta}$, where $R^{\eta}$ is an alkyl, aryl or other suitable substituent.

"Alkylsulfonyl" refers to —$SO_2$—$R^{\xi}$, where $R^{\xi}$ is an alkyl, which can be optionally substituted. Typical alkylsulfonyl groups include, but are not limited to, methylsulfonyl, ethylsulfonyl, n-propylsulfonyl, and the like.

"Arysulfonyl" refers to —$SO_2$—$R^{\lambda}$, where $R^{\lambda}$ is an aryl, which can be optionally substituted. Typical arylsulfonyl groups include, but are not limited to, phenylsulfonyl, (4-methylphenyl)sulfonyl, pyridinylsulfonyl, and the like.

"Heteroarylsulfonyl" refers to —$SO_2$—$R^{o}$, where $R^{o}$ is a heteroaryl group, which can be optionally substituted.

"Sulfinyl" refers to —SO—. Substituted sulfinyl refers to —SO—$R^{\eta}$, where $R^{\eta}$ is an alkyl, aryl or other suitable substituent.

"Alkylsulfinyl" refers to —SO—$R^{\xi}$, where $R^{\xi}$ is an alkyl, which can be optionally substituted. Typical alkylsulfinyl groups include, but are not limited to, methylsulfinyl, ethylsulfinyl, n-propylsulfinyl, and the like.

"Arysulfinyl" refers to —SO—$R^{\lambda}$, where $R^{\lambda}$ is an aryl, which can be optionally substituted. Typical arylsulfinyl groups include, but are not limited to, phenylsulfinyl, (4-methylphenyl)sulfinyl, pyridinylsulfinyl, and the like.

"Heteroarylsulfinyl" refers to —SO—$R^{o}$, where $R^{o}$ is a heteroaryl group, which can be optionally substituted.

"Alkylaminosulfonylalkyl" refers to an alkyl substituted with an alkyl-NH—$SO_2$— group.

"Arylsulfonylalkyl" refers to an alkyl substituted with an aryl-$SO_2$— group.

"Heteroarylsulfonylalkyl" refers to an alkyl substituted with a heteroaryl-$SO_2$— group.

"Aminosulfonyl" refers to —$SO_2NH_2$. Substituted aminosulfonyl refers to —$SO_2NR^{\delta}R^{\delta}$, where the amino group —$NR^{\eta}R^{\eta}$ is as defined herein.

"Heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to an alkyl substituted with a heteroaryl, i.e., heteroaryl-alkyl-groups, preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

"Heteroarylalkenyl" refers to an alkenyl substituted with a heteroaryl, i.e., heteroaryl-alkenyl-groups, preferably having from 2 to 6 carbon atoms inclusively in the alkenyl moiety and from 5 to 12 ring atoms inclusively in the heteroaryl moiety.

"Heteroarylalkynyl" refers to an alkynyl substituted with a heteroaryl, i.e., heteroaryl-alkynyl-groups, preferably having from 2 to 6 carbon atoms inclusively in the alkynyl moiety and from 5 to 12 ring atoms inclusively in the heteroaryl moiety.

"Heterocycle", "heterocyclic" and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Heterocycloalkylalkyl" refers to an alkyl substituted with a heterocycloalkyl, i.e., heterocycloalkyl-alkyl-groups, preferably having from 1 to 6 carbon atoms inclusively in the alkyl moiety and from 3 to 12 ring atoms inclusively in the heterocycloalkyl moiety.

"Heterocycloalkylalkenyl" refers to an alkenyl substituted with a heterocycloalkyl, i.e., heterocycloalkyl-alkenyl-groups, preferably having from 2 to 6 carbon atoms inclusively in the alkenyl moiety and from 3 to 12 ring atoms inclusively in the heterocycloalkyl moiety.

"Heterocycloalkylalkynyl" refers to an alkynyl substituted with a heterocycloalkyl, i.e., heterocycloalkyl-alkynyl-groups, preferably having from 2 to 6 carbon atoms inclusively in the alkynyl moiety and from 3 to 12 ring atoms inclusively in the heterocycloalkyl moiety.

"Membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

"Leaving group" generally refers to any atom or moiety that is capable of being displaced by another atom or moiety in a chemical reaction. More specifically, a leaving group refers to an atom or moiety that is readily displaced and substituted by a nucleophile (e.g., an amine, a thiol, an alcohol, or cyanide). Such leaving groups are well known and include carboxylates, N-hydroxysuccinimide ("NHS"), N-hydroxybenzotriazole, a halogen (fluorine, chlorine, bromine, or iodine), and alkyloxy groups. Non-limiting characteristics and examples of leaving groups can be found, for example in Organic Chemistry, 2d ed., Francis Carey (1992), pages 328-331; Introduction to Organic Chemistry, 2d ed., Andrew Streitwieser and Clayton Heathcock (1981), pages 169-171; and Organic Chemistry, 5th Ed., John McMurry, Brooks/Cole Publishing (2000), pages 398 and 408; all of which are incorporated herein by reference.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present disclosure, and is otherwise chemically reasonable.

"Optional" or "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," 4th Ed., Wiley Interscience (2006), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like.

"Polyol" as used herein refers to compounds containing multiple hydroxy groups. In reference to polymers, polyol includes polymers with hydroxyl functional groups. Exemplary polymeric polyols include, by way of example and not limitation, polyethers and polyesters, e.g., polyethylene glycol, polypropylene glycol, poly(tetramethylene) glycol and polytetrahydrofuran.

5.3 Engineered Transaminase Polypeptides

The present disclosure provides engineered polypeptides having transaminase activity, polynucleotides encoding the polypeptides, and methods for using the polypeptides. Where the foregoing description relates to polypeptides, it is to be understood that it also describes the polynucleotides encoding the polypeptides.

Aminotransferases, also known as transaminases, catalyze the transfer of an amino group from a primary amine of an amino donor substrate to the carbonyl group (e.g., a keto or aldehyde group) of an amino acceptor molecule. Aminotransferases have been identified from various organisms, such as *Alcaligenes denitrificans, Bordetella bronchiseptica, Bordetella parapertussis, Brucella melitensis, Burkholderia*

*malle, Burkholderia pseudomallei, Chromobacterium violaceum, Oceanicola granulosus* HTCC2516, *Oceanobacter* sp. RED65, *Oceanospirillum* sp. MED92, *Pseudomonas putida, Ralstonia solanacearum, Rhizobium meliloti, Rhizobium* sp. (strain NGR234), *Vibrio fluvialis, Bacillus thuringensis*, and *Klebsiella pneumoniae* (Shin et al., 2001, Biosci. Biotechnol, Biochem. 65:1782-1788).

Transaminases are useful for the chiral resolution of racemic amines by exploiting the ability of the transaminases to carry out the reaction in a stereospecific manner, i.e., preferential conversion of one enantiomer to the corresponding ketone, thereby resulting in a mixture enriched in the other enantiomer (see, e.g., Koselewski et al., 2009, Org Lett. 11(21):4810-2). The stereoselectivity of transaminases in the conversion of a ketone to the corresponding amine also make these enzymes useful in the asymmetric synthesis of optically pure amines from the corresponding keto compounds (see, e.g., Höhne et al., "Biocatalytic Routes to Optically Active Amines," Chem Cat Chem 1(1):42-51; Zua and Hua, 2009, Biotechnol J. 4(10):1420-31).

The ω-transaminase from *Vibrio fluvialis* (ω-VfT) displays high enantioselectivity for (S)-enantiomer of chiral amines and has distinctive substrate specificity for chiral aromatic amines (Shin and Kim, 2001, J. Org. Chem. 67:2848-2853). The high enantioselectivity of ω-VfT has been applied to chiral resolution of amines (H. Yun, et al., 2004, Biotechnol. Bioeng. 87:772-778; Shin and Kim, 1997, Biotechnol. Bioeng. 55:348-358; M. Hçhne, et al., 2008, Adv. Synth. Catal. 350:802-807). The enzyme has also been used in the asymmetric synthesis of optically pure amines using a prochiral ketone substrate. However, limitation in asymmetric synthesis is the unfavorable equilibrium of the reverse reaction (Shin and Kim, 1999, Biotechnol. Bioeng. 65, 206-211); inhibition of ω-VfT enzyme by the amine product (Shin et al., 2001, Biotechnol Bioeng 73:179-187; Yun and Kim, 2008, Biosci. Biotechnol. Biochem. 72(11): 3030-3033); low activity on amino acceptors having bulky side chains, such as aromatic groups (Shin and Kim, 2002, J. Org. Chem. 67:2848-2853); and low enzyme stability (Yun and Kim, supra).

Engineered transaminases derived from the transaminase of *Vibrio fluvialis* having increased resistance to aliphatic ketones are described in Yun et al., 2005, Appl Environ Micriobiol. 71(8):4220-4224) while ω-VfTs with broadened amino donor substrate specificity are described in Cho et al., 2008, Biotechnol Bioeng. 99(2):275-84. Patent publications WO2010081053 and US20100209981, incorporated by reference herein, describe engineered ω-VfTs having increased stability to temperature and/or organic solvent, and enzymatic activity towards structurally different amino acceptor molecules. Patent publication WO2011159910, incorporated by reference herein, describes engineered ω-VfTs optimized for the conversion of substrate 3'-hydroxyacetophenone to the product (S)-3-(1-aminoethyl)-phenol in enantiomeric excess.

The present disclosure relates to engineered transaminase polypeptides derived from *V. fluvialis* that efficiently mediate conversion of an alkylcarbonylalkyl or carbonylalkyl group on indoles to the corresponding amine. Significantly, the disclosure identifies amino acid residue positions and corresponding mutations in the transaminase polypeptide that increase the enzymatic activity, enantioselectivity, stability and refractoriness to product inhibition. In some embodiments, the engineered transaminases are capable of efficiently converting substrate compound (2), 1-(1H-5-fluoro-6-chloro-indol-3-yl)propan-2-one, to product compound (1), (S)-1-(1H-5-fluoro-6-chloro-indol-3-yl)propan-2-amine, in the presence of an amino donor under suitable reaction conditions, where the (S)-1-(1H-5-fluoro-6-chloro-indol-3-yl)propan-2-amine is produced in enantiomeric excess of compound (1b), (R)-1-(1H-5-fluoro-6-chloro-indol-3-yl) propan-2-amine (as shown in Scheme 1).

Scheme 1

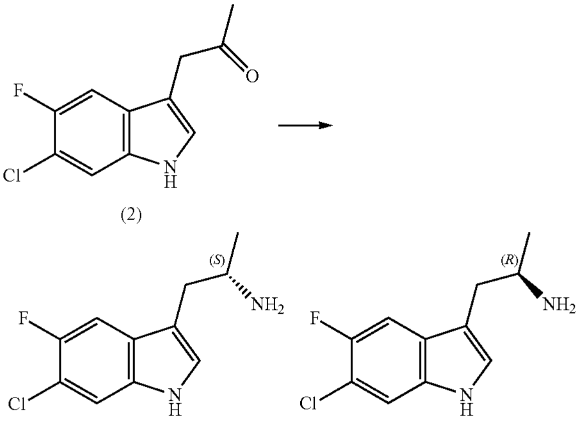

(2)

(1)

(1b)

In some embodiments, the polypeptides are non-naturally occurring transaminases engineered for improved properties as compared to the wild-type *V. fluvialis* polypeptide of SEQ ID NO:2, or another engineered polypeptide, for example SEQ ID NO:4. These engineered transaminase polypeptides adapted for efficient conversion of 1-(1H-5-fluoro-6-chloro-indol-3-yl)propan-2-one to (S)-1-(1H-5-fluoro-6-chloro-indol-3-yl)propan-2-amine have one or more residue differences as compared to the amino acid sequence of SEQ ID NO:2 or a reference engineered transaminase polypeptide, such as the reference polypeptide of SEQ ID NO:4. The residue differences are associated with enhancements in enzyme properties, including enzymatic activity, enzyme stability, and resistance to inhibition by the product amine.

In some embodiments, the engineered transaminase polypeptides show increased activity in the conversion of the substrate 1-(1H-5-fluoro-6-chloro-indol-3-yl)propan-2-one to product (S)-1-(1H-5-fluoro-6-chloro-indol-3-yl)propan-2-amine product in enantiomeric excess in a defined time with the same amount of enzyme as compared to the wild-type or a reference engineered enzyme. In some embodiments, the engineered transaminase polypeptide has at least about 1.2 fold, 1.5 fold, 2 fold, 3 fold, 4 fold, 5 fold, 10 fold, 20 fold, 30 fold, 40 fold, or 50 fold or more the activity as compared to the polypeptide represented by SEQ ID NO:4 under suitable reaction conditions.

In some embodiments, the engineered transaminase polypeptides have increased stability to temperature and/or solvents used in the conversion reaction as compared to the wild-type or a reference engineered enzyme. In some embodiments, the engineered transaminase polypeptide has at least 1.2 fold, 1.5 fold, 2 fold, 3 fold, 4 fold, 5 fold, 10 fold or more the stability as compared to the polypeptide of SEQ ID NO:4 under suitable reaction conditions.

In some embodiments, the engineered transaminase polypeptides have increased refractoriness or resistance to inhibition by product amine (S)-1-(1H-5-fluoro-6-chloro-indol-3-yl)propan-2-amine as compared to the wild-type or a reference engineered enzyme. In some embodiments, the engineered transaminase polypeptide has at least 1.2 fold, 1.5 fold, 2 fold, 3 fold, 4 fold, 5 fold, or more increased resistance to inhibition by 1-(1H-5-fluoro-6-chloro-indol-3-yl)propan-2-amine, in particular (S)-1-(1H-5-fluoro-6-chloro-indol-3-yl)propan-2-amine, as compared to the polypeptide represented by SEQ ID NO:4 under suitable reaction conditions, as further described below.

In some embodiments, the engineered transaminase polypeptides are capable of converting the substrate 1-(1H-5-fluoro-6-chloro-indol-3-yl)propan-2-one to product (S)-1-(1H-5-fluoro-6-chloro-indol-3-yl)propan-2-amine in enantiomeric excess of greater than 90%, 91%, 92%, 93%, 94%, 95%, 96%, 97%, 98%, 99%, 99.5 or greater over (R)-1-(1H-5-fluoro-6-chloro-indol-3-yl)propan-2-amine under suitable reaction conditions.

In some embodiments, the engineered transaminase polypeptides are capable of converting substrate compound (2) to product compound (1) with increased tolerance for the presence of substrate relative to the reference polypeptide of SEQ ID NO: 4 under suitable reaction conditions. Thus, in some embodiments the engineered transaminase polypeptides are capable of converting the substrate compound (2) to product compound (1) under a substrate loading concentration of at least about 1 g/L, about 5 g/L, about 10 g/L, about 20 g/L, about 30 g/L, about 40 g/L, about 50 g/L, about 70 g/L, about 100 g/L, about 125 g/L, about 150 g/L. about 175 g/L or about 200 g/L or more with a percent conversion of at least about at least about 50%, at least about 60%, at least about 70%, at least about 80%, at least about 90%, at least about 95%, at least about 98%, or at least about 99%, in a reaction time of about 72 h or less, about 48 h or less, about 36 h or less, or about 24 h less, under suitable reaction conditions.

The suitable reaction conditions under which the above-described improved properties of the engineered polypeptides carry out the conversion can be determined with respect to concentrations or amounts of polypeptide, substrate, cofactor, buffer, co-solvent, pH, and/or conditions including temperature and reaction time, as further described below and in the Examples.

The exemplary engineered polypeptides associated with their improved properties include one or more residue differences as compared to SEQ ID NO:2 at the following residue positions: X9; X14; X18; X21; X26; X31; X33; X41; X45; X47; X57; X70; X86; X88; X107; X113; X132; X133; X146; X147; X148; X153; X163; X168; X173; X177; X203; X211; X233T; X235; X244; X250; X284; X294; X314; X315; X318; X323; X324; X324; X346; X383; X391; X395; X398; X400; X417; X419; X420; X423; X424; X427; X448; and X451. The specific amino acid differences at each of these positions that are associated with the improved properties include: X9T; X14V; X18A; X21H; X26R; X31M; X31S; X33T; X41L; X45H; X47N; X57F; X57Y; X70A; X86D; X86Y; X88A; X88L; X107P; X113L; X113V; X132F; X133R; X146L; X147K; X148Q; X148R; X153S; X163F; X163I; X163L; X163R; X163V; X168K; X168S; X173A; X177L; X203S; X211K; X233T; X235P; X244T; X250A; X284A; X294V; X314N; X315G; X318D; X323T; X324G; X324H; X346L; X383V; X391A; X395P; X398L; X398V; X398W; X400G; X417M; X419S; X420N; X423I; X424V; X424A; X427Y; X448E; and X451D.

The residue differences as compared to the engineered transaminase represented by SEQ ID NO:4 includes those at residue positions: X14; X26; X31; X33; X41; X47; X57; X70; X86; X88; X107; X113; X132; X148; X163; X168; X173; X203; X250; X284; X314; X315; X324; X346; X395; X398; X400; X417; X419; X420; X423; X424; X448; and X451. The specific amino acid differences at these positions include: X14V; X26R; X31S; X33T; X41L; X47N; X57F; X57Y; X70A; X86D; X88A; X88L; X107P; X113L; X113V; X132F; X148Q; X148R; X163I; X163L; X163R; X163V; X168K; X168S; X173A; X203S; X250A; X284A; X314N; X315G; X324H; X346L; X395P; X398L; X398V; X398W; X400G; X417M; X419S; X420N; X423I; X424V; X448E; and X451D. Although residue differences compared to SEQ ID NO:4 also occur at residue positions X153 and X383, these differences represent reversions to the amino acid residue present on the wild-type sequence of SEQ ID NO:2, indicating that interconversions between amino acids S and V at residue position X153 and between amino acids A and V at residue position X383 have no significant deleterious effects on the engineered enzyme properties.

The structure and function information for exemplary non-naturally occurring (or engineered) transaminase polypeptides of the present disclosure are shown below in Tables 2A and 2B. The odd numbered sequence identifiers (i.e., SEQ ID NOs) refer to the nucleotide sequence encoding the amino acid sequence provided by the even numbered SEQ ID NOs, and the sequences are provided in the electronic sequence listing file accompanying this disclosure, which is hereby incorporated by reference herein. The amino acid residue differences are based on comparison to the reference sequence of SEQ ID NO: 4, which is an engineered transaminase derived from the wild-type ω-VfT polypeptide having the following 24 amino acid residue differences relative to SEQ ID NO:2: A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; and F427Y. The activity of each engineered polypeptide relative to the reference polypeptide of SEQ ID NO: 4 was determined as conversion of the ketone substrate 1-(1H-5-fluoro-6-chloro-indol-3-yl)propan-2-one, to product amine compound (S)-1-(1H-5-fluoro-6-chloro-indol-3-yl)propan-2-amine over a set time period and temperature in a high-throughput (HTP) assay, which was used as the primary screen. The HTP assay values in Table 2A were determined using *E. coli*. clear cell lysates in 96 well-plate format of ~200 μL volume per well following assay reaction conditions as noted in the table and the Examples. In some instances, a shake-flask powder (SFP) and/or downstream processed (DSP) powder assay were used as a secondary screen to assess the properties of the engineered transaminases, the results of which are provided in Table 2B. The SFP and DSP forms provide a more purified powder preparation of the engineered polypeptides. For example, the engineered transaminase in the SFP preparations is approximately 30% of the total protein while the DSP preparations can contain the engineered transaminases that are approximately 80% of total protein.

The activity levels (i.e., "+" "++", etc.) are defined as follows: "+" indicates 1.2 fold or greater activity as compared to that of SEQ ID NO: 4 for engineered transaminase polypeptides SEQ ID NO: 6 to 14, and 1.2 fold or greater activity as compared to that of SEQ ID NO: 8 for engineered transaminase polypeptides SEQ ID NO: 16 to 154. An activity level of "++" indicates 5 fold or greater activity as compared to that of SEQ ID NO:4 for engineered transaminase polypeptides SEQ ID NO: 6-14, and 5 fold or greater activity as compared that of SEQ ID NO:8 for engineered transaminase polypeptides SEQ ID NO: 16 to 154. The tolerance to product inhibition data (i.e., Product Tolerance) is obtained by including the following amounts of product (S)-1-(1H-5-fluoro-6-chloro-indol-3-yl)propan-2-amine in the assay and comparing the activity to that of a reference enzyme under the same conditions: 14 g/L for analysis of the engineered transaminase polypeptides of SEQ ID NO. 6 to 14, and 16 g/L for analysis of the engineered transaminase polypeptides SEQ ID NO. 16 to 154. Assessment of stability was made by comparing activities at two different temperatures, 55° C. and 50° C.

TABLE 2A

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a,b] | Stability[c] | Product Tolerance[d,e] |
|---|---|---|---|---|---|
| 1/2 | n/a | | nd | nd | nd |
| 3/4 | A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; F427Y | | "Control" | "Control" | "Control" |
| 5/6 | A9T; G18A; D21H; V31M; N45H; F86Y; A133R; R146L; W147K; V153S; K163L; V177L; R211K; P233T; A235P; P244T; M294V; P318D; A323T; S324G; A383V; T391A; C424A; F427Y | F163L | + | + | + |
| 7/8 | A9T; G18A; D21H; V31M; N45H; F86Y; A133R; R146L; W147K; V153S; K163I; V177L; R211K; P233T; A235P; P244T; M294V; P318D; A323T; S324G; A383V; T391A; C424A; F427Y | F163I | + | + | nd |
| 9/10 | A9T; G18A; D21H; V31M; N45H; F86Y; A133R; R146L; W147K; V153S; K163R; V177L; R211K; P233T; A235P; P244T; M294V; P318D; A323T; S324G; A383V; T391A; C424A; F427Y | F163R | + | nd | nd |
| 11/12 | A9T; G18A; D21H; V31M; N45H; F86D; A133R; R146L; W147K; V153S; K163F; V177L; R211K; P233T; A235P; P244T; M294V; P318D; A323T; S324G; A383V; T391A; C424A; F427Y | Y86D | + | + | + |
| 13/14 | A9T; G18A; D21H; V31M; N45H; F86Y; A133R; R146L; W147K; V153S; K163V; V177L; R211K; P233T; A235P; P244T; M294V; P318D; A323T; S324G; A383V; T391A; C424A; F427Y | F163V | + | nd | nd |
| 15/16 | A9T; Y14V; G18A; D21H; H26R; V31M; N45H; F86Y; R88L; Y113L; A133R; R146L; W147K; V153S; K163L; V177L; R211K; P233T; A235P; P244T; M294V; P318D; A323T; S324G; A383V; T391A; C424A; F427Y | Y14V; H26R; R88L; Y113L; F163L | + | + | ++ |
| 17/18 | A9T; Y14V; G18A; D21H; H26R; V31M; N45H; W57F; F86Y; A133R; R146L; W147K; V153S; K163L; V177L; R211K; P233T; A235P; P244T; M294V; P318D; A323T; S324G; A383V; T391A; C424A; F427Y | Y14V; H26R; W57F; F163L | nd | + | + |
| 19/20 | A9T; Y14V; G18A; D21H; V31M; V33T; N45H; W57F; F86Y; R88L; Y113L; A133R; R146L; W147K; V153S; K163L; V177L; R211K; P233T; A235P; P244T; M294V; P318D; A323T; S324G; A383V; T391A; C424A; F427Y; V448E | Y14V; V33T; W57F; R88L; Y113L; F163L; V448E | nd | + | nd |
| 21/22 | A9T; Y14V; G18A; D21H; H26R; V31M; N45H; F86Y; R88A; Y113L; A133R; R146L; W147K; N148Q; V153S; K163I; V177L; R203S; R211K; P233T; A235P; P244T; M294V; P318D; A323T; S324G; A383V; T391A; C424A; F427Y | Y14V; H26R; R88A; Y113L; N148Q; L163I; R203S | + | + | + |

TABLE 2A-continued

| Engineered Polypeptides and Relative Enzyme Improvements Using HTP Preparations | | | | | |
|---|---|---|---|---|---|
| SEQ ID NO: | Active Mutations (relative to SEQ ID NO: 2) | Active Mutations (relative to SEQ ID NO: 4) | Activity[a,b] | Stability[c] | Product Tolerance[d,e] |
| 23/24 | A9T; G18A; D21H; V31M; N45H; W57F; F86Y; R88L; Y113L; A133R; R146L; W147K; N148Q; V153S; K163I; V177L; R211K; P233T; A235P; P244T; M294V; P318D; A323T; S324G; A383V; T391A; C424A; F427Y; V448E | W57F; R88L; Y113L; N148Q; L163I; V448E | + | + | + |
| 25/26 | A9T; Y14V; G18A; D21H; V31M; N45H; F86Y; A133R; R146L; W147K; V153S; K163L; V177L; R211K; P233T; A235P; P244T; M294V; P318D; A323T; S324G; A383V; T391A; C424A; F427Y | Y14V; F163L | nd | nd | + |
| 27/28 | A9T; Y14V; G18A; D21H; H26R; V31M; N45H; F86Y; R88A; A133R; R146L; W147K; N148Q; V153S; K163I; V177L; R211K; P233T; A235P; P244T; M294V; P318D; A323T; S324G; A383V; T391A; C424A; F427Y | Y14V; H26R; R88A; N148Q; L163I | + | + | + |
| 29/30 | A9T; Y14V; G18A; D21H; H26R; V31M; N45H; F86Y; R88L; Y113V; A133R; R146L; W147K; V153S; K163L; V177L; R211K; P233T; A235P; P244T; M294V; P318D; A323T; S324G; A383V; T391A; C424A; F427Y | Y14V; H26R; R88L; Y113V; F163L | + | + | + |
| 31/32 | A9T; Y14V; G18A; D21H; V31M; N45H; W57F; F86Y; Y113V; A133R; R146L; W147K; N148Q; V153S; K163L; V177L; R211K; P233T; A235P; P244T; M294V; P318D; A323T; S324G; A383V; T391A; C424A; F427Y | Y14V; W57F; Y113V; N148Q; F163L | + | + | nd |
| 33/34 | A9T; Y14V; G18A; D21H; H26R; V31M; N45H; W57F; F86Y; A133R; R146L; W147K; N148Q; V153S; K163I; V177L; R211K; P233T; A235P; P244T; M294V; P318D; A323T; S324G; A383V; T391A; C424A; F427Y | Y14V; H26R; W57F; N148Q; L163I | nd | + | + |
| 35/36 | A9T; Y14V; G18A; D21H; H26R; V31M; N45H; F86Y; A133R; R146L; W147K; V153S; K163L; V177L; R211K; P233T; A235P; P244T; M294V; P318D; A323T; S324G; A383V; T391A; C424A; F427Y | Y14V; H26R; F163L | nd | + | + |
| 37/38 | A9T; Y14V; G18A; D21H; H26R; V31M; N45H; W57F; F86Y; Y113L; A133R; R146L; W147K; V153S; K163L; V177L; R211K; P233T; A235P; P244T; M294V; P318D; A323T; S324G; A383V; T391A; C424A; F427Y | Y14V; H26R; W57F; Y113L; F163L | nd | + | + |
| 39/40 | A9T; Y14V; G18A; D21H; H26R; V31M; N45H; F86Y; A133R; R146L; W147K; V153S; K163I; V177L; R211K; P233T; A235P; P244T; M294V; P318D; A323T; S324G; A383V; T391A; C424A; F427Y | Y14V; H26R; L163I | nd | + | + |
| 41/42 | A9T; Y14V; G18A; D21H; H26R; V31M; N45H; W57F; F86Y; R88L; A133R; R146L; W147K; V153S; K163I; V177L; R211K; P233T; A235P; P244T; M294V; P318D; A323T; S324G; A383V; T391A; C424A; F427Y | Y14V; H26R; W57F; R88L; L163I | nd | + | + |
| 43/44 | A9T; Y14V; G18A; D21H; H26R; V31M; N45H; F86Y; Y113V; A133R; R146L; W147K; | Y14V; H26R; Y113V; L163I | nd | + | nd |

TABLE 2A-continued

Engineered Polypeptides and Relative Enzyme Improvements Using HTP Preparations

| SEQ ID NO: | Active Mutations (relative to SEQ ID NO: 2) | Active Mutations (relative to SEQ ID NO: 4) | Activity[a,b] | Stability[c] | Product Tolerance[d,e] |
|---|---|---|---|---|---|
| | V153S; K163I; V177L; R211K; P233T; A235P; P244T; M294V; P318D; A323T; S324G; A383V; T391A; C424A; F427Y | | | | |
| 45/46 | A9T; Y14V; G18A; D21H; H26R; V31M; N45H; W57F; F86Y; R88L; Y113L; A133R; R146L; W147K; N148Q; V153S; K163I; V177L; R211K; P233T; A235P; P244T; M294V; P318D; A323T; S324G; A383V; T391A; C424A; F427Y | Y14V; H26R; W57F; R88L; Y113L; N148Q; L163I | nd | + | + |
| 47/48 | A9T; Y14V; G18A; D21H; V31M; N45H; W57F; F86Y; R88L; A133R; R146L; W147K; N148Q; V153S; K163I; V177L; R211K; P233T; A235P; P244T; M294V; P318D; A323T; S324G; A383V; T391A; C424A; F427Y | Y14V; W57F; R88L; N148Q; L163I | + | + | + |
| 49/50 | A9T; Y14V; G18A; D21H; H26R; V31M; N45H; W57F; F86Y; R88L; Y113V; A133R; R146L; W147K; N148R; V153S; K163L; V177L; R211K; P233T; A235P; P244T; M294V; P318D; A323T; S324G; A383V; T391A; C424A; F427Y | Y14V; H26R; W57F; R88L; Y113V; N148R; F163L | nd | + | nd |
| 51/52 | A9T; Y14V; G18A; D21H; V31M; N45H; F86Y; R88A; Y113V; A133R; R146L; W147K; V153S; K163I; V177L; R211K; P233T; A235P; P244T; M294V; P318D; A323T; S324G; A383V; T391A; C424A; F427Y | Y14V; R88A; Y113V; L163I | + | + | + |
| 53/54 | A9T; Y14V; G18A; D21H; H26R; V31M; N45H; F86Y; A133R; R146L; W147K; V153S; K163L; V177L; R211K; P233T; A235P; P244T; D250A; M294V; P318D; A323T; S324G; A383V; T391A; C424A; F427Y | Y14V; H26R; F163L; D250A | nd | nd | + |
| 55/56 | A9T; Y14V; G18A; D21H; H26R; V31M; N45H; F86Y; R88L; Y113L; A133R; R146L; W147K; V153S; K163I; V177L; R211K; P233T; A235P; P244T; M294V; P318D; A323T; S324G; A383V; T391A; C424A; F427Y | Y14V; H26R; R88L; Y113L; L163I | + | + | + |
| 57/58 | A9T; Y14V; G18A; D21H; V31M; N45H; W57F; F86Y; R88A; Y113L; A133R; R146L; W147K; V153S; K163L; V177L; R211K; P233T; A235P; P244T; M294V; P318D; A323T; S324G; A383V; T391A; C424A; F427Y | Y14V; W57F; R88A; Y113L; F163L | nd | nd | + |
| 59/60 | A9T; Y14V; G18A; D21H; H26R; V31M; N45H; W57F; F86Y; Y113L; A133R; R146L; W147K; N148R; V153S; K163L; V177L; R211K; P233T; A235P; P244T; M294V; P318D; A323T; S324G; A383V; T391A; C424A; F427Y | Y14V; H26R; W57F; Y113L; N148R; F163L | nd | + | + |
| 61/62 | A9T; Y14V; G18A; D21H; V31M; N45H; W57F; F86Y; Y113L; A133R; R146L; W147K; V153S; K163I; V177L; R211K; P233T; A235P; P244T; M294V; P318D; A323T; S324G; A383V; T391A; C424A; F427Y | Y14V; W57F; Y113L; L163I | + | + | + |
| 63/64 | A9T; G18A; D21H; V31M; N45H; F86Y; R88L; A133R; R146L; W147K; V153S; K163I; L173A; V177L; R211K; P233T; | D86Y; R88L; F163I; L173A; S400G; A424V | + | + | nd |

TABLE 2A-continued

| Engineered Polypeptides and Relative Enzyme Improvements Using HTP Preparations | | | | | |
|---|---|---|---|---|---|
| SEQ ID NO: | Active Mutations (relative to SEQ ID NO: 2) | Active Mutations (relative to SEQ ID NO: 4) | Activity[a,b] | Stability[c] | Product Tolerance[d,e] |
| | A235P; P244T; S284A; M294V; P318D; A323T; S324G; A383V; T391A; S400G; L417M; C424V; F427Y | | | | |
| 65/66 | A9T; G18A; D21H; V31M; V33T; N45H; F86Y; R88L; A133R; R146L; W147K; V153S; K163F; L173A; V177L; R211K; P233T; A235P; P244T; S284A; M294V; P318D; A323T; S324G; T391A; S400G; C424A; F427Y | V33T; D86Y; R88L; L173A; V383A; S400G | + | + | nd |
| 67/68 | A9T; G18A; D21H; V31M; N45H; F86D; A133R; R146L; W147K; V153S; K163F; V177L; R211K; P233T; A235P; P244T; M294V; P318D; A323T; S324H; A383V; T391A; S400G; C424A; F427Y | Y86D; G324H; S400G | + | + | nd |
| 69/70 | A9T; G18A; D21H; V31M; N45H; F86D; A133R; R146L; W147K; V153S; K163F; V168K; V177L; R211K; P233T; A235P; P244T; S284A; M294V; P318D; A323T; S324H; T391A; S400G; C424A; F427Y | Y86D; V168K; G324H; V383A; S400G | nd | + | nd |
| 71/72 | A9T; G18A; D21H; V31M; N45H; F86D; A133R; R146L; W147K; V153S; K163F; L173A; V177L; R211K; P233T; A235P; P244T; S284A; M294V; P318D; A323T; S324H; A383V; T391A; C424A; F427Y | Y86D; L173A; G324H | nd | + | nd |
| 73/74 | A9T; G18A; D21H; V31M; N45H; F86D; A133R; R146L; W147K; V153S; K163F; V177L; R211K; P233T; A235P; P244T; M294V; P318D; A323T; S324G; T391A; S400G; C424A; F427Y | Y86D; V383A; S400G | nd | + | + |
| 75/76 | A9T; G18A; D21H; V31M; N45H; F86D; A133R; R146L; W147K; V153S; K163F; L173A; V177L; R211K; P233T; A235P; P244T; M294V; P318D; A323T; S324G; A383V; T391A; S400G; C424A; F427Y; V448E | Y86D; L173A; S400G; V448E | nd | + | + |
| 77/78 | A9T; G18A; D21H; V31M; N45H; F86D; A133R; R146L; W147K; V153S; K163F; V177L; R211K; P233T; A235P; P244T; S284A; M294V; P318D; A323T; S324H; A383V; T391A; S400G; C424A; F427Y | Y86D; G324H; S400G | nd | + | nd |
| 79/80 | A9T; G18A; D21H; V31M; N45H; F86D; A133R; R146L; W147K; V153S; K163F; L173A; V177L; R211K; P233T; A235P; P244T; S284A; M294V; P318D; A323T; S324H; A383V; T391A; S400G; C424A; F427Y | Y86D; L173A; G324H; S400G | nd | + | nd |
| 81/82 | A9T; G18A; D21H; V31M; I41L; N45H; W57Y; D70A; F86Y; D107P; H132F; A133R; R146L; W147K; V153S; K163L; V177L; R211K; P233T; A235P; P244T; M294V; I314N; P318D; A323T; S324G; A383V; T391A; S398V; C424A; F427Y; E451D | I41L; W57Y; D70A; D107P; H132F; F163L; I314N; S398V; E451D | nd | + | nd |

TABLE 2A-continued

| SEQ ID NO: | Active Mutations (relative to SEQ ID NO: 2) | Active Mutations (relative to SEQ ID NO: 4) | Activity[a,b] | Stability[c] | Product Tolerance[d,e] |
|---|---|---|---|---|---|
| Engineered Polypeptides and Relative Enzyme Improvements Using HTP Preparations | | | | | |
| 83/84 | A9T; G18A; D21H; V31M; I41L; N45H; R47N; W57Y; F86Y; A133R; R146L; W147K; V153S; K163L; V177L; R211K; P233T; A235P; P244T; M294V; E315G; P318D; A323T; S324G; A383V; T391A; S398V; L423I; C424A; F427Y | I41L; R47N; W57Y; F163L; E315G; S398V; L423I | nd | + | nd |
| 85/86 | A9T; G18A; D21H; V31M; I41L; N45H; W57Y; F86Y; A133R; R146L; W147K; V153S; K163L; V177L; R211K; P233T; A235P; P244T; M294V; E315G; P318D; A323T; S324G; A383V; T391A; S398V; C424A; F427Y | I41L; W57Y; F163L; E315G; S398V | + | + | nd |
| 87/88 | A9T; G18A; D21H; V31M; I41L; N45H; W57Y; F86Y; D107P; H132F; A133R; R146L; W147K; V153S; K163L; V177L; R211K; P233T; A235P; P244T; M294V; E315G; P318D; A323T; S324G; A383V; T391A; G395P; S398W; C424A; F427Y | I41L; W57Y; D107P; H132F; F163L; E315G; G395P; S398W | + | + | nd |
| 89/90 | A9T; G18A; D21H; V31M; I41L; N45H; F86Y; D107P; H132F; A133R; R146L; W147K; V153S; K163L; V177L; R211K; P233T; A235P; P244T; M294V; P318D; A323T; S324G; A383V; T391A; S398V; C424A; F427Y; E451D | I41L; D107P; H132F; F163L; S398V; E451D | + | + | nd |
| 91/92 | A9T; G18A; D21H; V31M; I41L; N45H; W57Y; F86Y; D107P; H132F; A133R; R146L; W147K; V153S; K163L; V177L; R211K; P233T; A235P; P244T; M294V; I314N; E315G; P318D; A323T; S324G; A383V; T391A; S398V; L423I; C424A; F427Y; E451D | I41L; W57Y; D107P; H132F; F163L; I314N; E315G; S398V; L423I; E451D | + | + | nd |
| 93/94 | A9T; G18A; D21H; V31M; I41L; N45H; W57Y; F86Y; D107P; H132F; A133R; R146L; W147K; V153S; K163L; V177L; R211K; P233T; A235P; P244T; M294V; E315G; P318D; A323T; S324G; A383V; T391A; S398V; L423I; C424A; F427Y | I41L; W57Y; D107P; H132F; F163L; E315G; S398V; L423I | nd | + | nd |
| 95/96 | A9T; G18A; D21H; V31M; I41L; N45H; W57Y; D70A; F86Y; D107P; H132F; A133R; R146L; W147K; V153S; K163L; V177L; R211K; P233T; A235P; P244T; M294V; I314N; P318D; A323T; S324G; A383V; T391A; S398W; Q419S; C424A; F427Y | I41L; W57Y; D70A; D107P; H132F; F163L; I314N; S398W; Q419S | nd | + | nd |
| 97/98 | A9T; G18A; D21H; V31S; N45H; W57F; F86Y; A133R; R146L; W147K; V153S; K163I; V177L; R211K; P233T; A235P; P244T; M294V; I314N; P318D; A323T; S324G; A346L; A383V; T391A; G395P; S398W; C424A; F427Y; E451D | M31S; W57F; L163I; I314N; A346L; G395P; S398W; E451D | + | + | + |
| 99/100 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398L; Q419S; C424A; F427Y | M31S; W57F; L163I; E315G; A346L; S398L; Q419S | + | + | nd |
| 101/102 | A9T; G18A; D21H; V31S; I41L; N45H; W57F; F86Y; R88A; A133R; R146L; W147K; V153S; K163I; V168S; V177L; R211K; | M31S; I41L; W57F; R88A; L163I; V168S; A346L; S398V; | nd | + | nd |

TABLE 2A-continued

| Engineered Polypeptides and Relative Enzyme Improvements Using HTP Preparations | | | | | |
|---|---|---|---|---|---|
| SEQ ID NO: | Active Mutations (relative to SEQ ID NO: 2) | Active Mutations (relative to SEQ ID NO: 4) | Activity[a,b] | Stability[c] | Product Tolerance[d,e] |
| | P233T; A235P; P244T; M294V; P318D; A323T; S324G; A346L; A383V; T391A; S398V; C424A; F427Y; E451D | E451D | | | |
| 103/104 | A9T; G18A; D21H; V31S; N45H; W57F; F86Y; A133R; R146L; W147K; V153S; K163L; V168S; V177L; R211K; P233T; A235P; P244T; M294V; E315G; P318D; A323T; S324G; A346L; A383V; T391A; S398V; Q419S; C424A; F427Y | M31S; W57F; F163L; V168S; E315G; A346L; S398V; Q419S | + | + | nd |
| 105/106 | A9T; G18A; D21H; V31S; N45H; W57F; F86Y; A133R; R146L; W147K; V153S; K163L; V177L; R211K; P233T; A235P; P244T; M294V; I314N; P318D; A323T; S324G; A383V; T391A; S398W; C424A; F427Y | M31S; W57F; F163L; I314N; S398W | + | + | nd |
| 107/108 | A9T; G18A; D21H; V31S; N45H; W57F; F86Y; A133R; R146L; W147K; V153S; K163L; V177L; R211K; P233T; A235P; P244T; M294V; P318D; A323T; S324G; A383V; T391A; C424A; F427Y | M31S; W57F; F163L | + | + | nd |
| 109/110 | A9T; G18A; D21H; V31S; N45H; W57F; F86Y; A133R; R146L; W147K; V153S; K163I; V168K; V177L; R211K; P233T; A235P; P244T; M294V; E315G; P318D; A323T; S324G; A346L; A383V; T391A; S398W; C424A; F427Y; E451D | M31S; W57F; L163I; V168K; E315G; A346L; S398W; E451D | + | + | nd |
| 111/112 | A9T; Y14V; G18A; D21H; V31S; N45H; W57F; F86Y; A133R; R146L; W147K; V153S; K163L; V177L; R211K; P233T; A235P; P244T; M294V; I314N; P318D; A323T; S324G; A346L; A383V; T391A; S398V; C424A; F427Y | Y14V; M31S; W57F; F163L; I314N; A346L; S398V | + | + | nd |
| 113/114 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398L; C424A; F427Y | M31S; W57F; L163I; E315G; A346L; S398L | + | + | nd |
| 115/116 | A9T; G18A; D21H; V31S; N45H; F86Y; A133R; R146L; W147K; V153S; K163I; V177L; R211K; P233T; A235P; P244T; M294V; E315G; P318D; A323T; S324G; A346L; A383V; T391A; S398V; C424A; F427Y; E451D | M31S; L163I; E315G; A346L; S398V; E451D | + | + | nd |
| 117/118 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398W; C424A; F427Y; E451D | M31S; W57F; L163I; E315G; A346L; S398W; E451D | + | + | nd |
| 119/120 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398V; C424A; F427Y | M31S; W57F; L163I; E315G; A346L; S398V | + | + | nd |
| 121/122 | A9T; G18A; D21H; V31M; N45H; W57F; F86Y; A133R; R146L; W147K; V153S; K163L; | W57F; F163L; A346L; S398L | nd | + | + |

TABLE 2A-continued

| SEQ ID NO: | Active Mutations (relative to SEQ ID NO: 2) | Active Mutations (relative to SEQ ID NO: 4) | Activity[a,b] | Stability[c] | Product Tolerance[d,e] |
|---|---|---|---|---|---|
| Engineered Polypeptides and Relative Enzyme Improvements Using HTP Preparations | | | | | |
| | V177L; R211K; P233T; A235P; P244T; M294V; P318D; A323T; S324G; A346L; A383V; T391A; S398L; C424A; F427Y | | | | |
| 123/124 | A9T; G18A; D21H; V31M; N45H; W57F; F86Y; A133R; R146L; W147K; V153S; K163L; V168K; V177L; R211K; P233T; A235P; P244T; M294V; I314N; E315G; P318D; A323T; S324G; A346L; A383V; T391A; S398V; C424A; F427Y | W57F; F163L; V168K; I314N; E315G; A346L; S398V | + | + | ++ |
| 125/126 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398V; L423I; C424A; F427Y | M31S; W57F; L163I; E315G; A346L; S398V; L423I | + | + | nd |
| 127/128 | A9T; G18A; D21H; V31S; N45H; W57F; F86Y; A133R; R146L; W147K; V153S; K163L; V177L; R211K; P233T; A235P; P244T; M294V; I314N; E315G; P318D; A323T; S324G; A346L; A383V; T391A; S398V; Q419S; C424A; F427Y | M31S; W57F; F163L; I314N; E315G; A346L; S398V; Q419S | + | + | nd |
| 129/130 | A9T; Y14V; G18A; D21H; H26R; V31M; N45H; F86Y; A133R; R146L; W147K; V153S; K163I; V177L; R211K; P233T; A235P; P244T; S284A; M294V; P318D; A323T; S324G; A383V; T391A; S400G; L417M; S420N; C424A; F427Y | Y14V; H26R; L163I; S284A; S400G; L417M; S420N | nd | nd | + |
| 131/132 | A9T; Y14V; G18A; D21H; V31M; N45H; F86Y; A133R; R146L; W147K; V153S; K163L; L173A; V177L; R211K; P233T; A235P; P244T; M294V; P318D; A323T; S324G; A383V; T391A; S400G; S420N; C424A; F427Y | Y14V; F163L; L173A; S400G; S420N | + | + | ++ |
| 133/134 | A9T; Y14V; G18A; D21H; V31M; N45H; F86Y; Y113L; A133R; R146L; W147K; V153S; K163L; V177L; R211K; P233T; A235P; P244T; S284A; M294V; P318D; A323T; S324G; A383V; T391A; C424V; F427Y | Y14V; Y113L; F163L; S284A; A424V | + | + | ++ |
| 135/136 | A9T; Y14V; G18A; D21H; V31M; N45H; F86Y; R88L; A133R; R146L; W147K; V153S; K163L; V177L; R211K; P233T; A235P; P244T; M294V; P318D; A323T; S324H; A383V; T391A; S400G; L417M; C424A; F427Y | Y14V; R88L; F163L; G324H; S400G; L417M | + | + | nd |
| 137/138 | A9T; Y14V; G18A; D21H; H26R; V31M; N45H; W57F; F86Y; Y113L; A133R; R146L; W147K; V153S; K163L; V177L; R211K; P233T; A235P; P244T; S284A; M294V; P318D; A323T; S324G; A383V; T391A; C424A; F427Y | Y14V; H26R; W57F; Y113L; F163L; S284A | nd | nd | + |
| 139/140 | A9T; Y14V; G18A; D21H; H26R; V31M; N45H; F86Y; A133R; R146L; W147K; V153S; K163L; V177L; R211K; P233T; A235P; P244T; S284A; M294V; P318D; A323T; S324G; T391A; S400G; C424A; F427Y | Y14V; H26R; F163L; S284A; V383A; S400G | nd | nd | ++ |
| 141/142 | A9T; Y14V; G18A; D21H; H26R; V31M; N45H; F86Y; | Y14V; H26R; Y113L; F163L; | + | + | nd |

TABLE 2A-continued

| Engineered Polypeptides and Relative Enzyme Improvements Using HTP Preparations | | | | | |
|---|---|---|---|---|---|
| SEQ ID NO: | Active Mutations (relative to SEQ ID NO: 2) | Active Mutations (relative to SEQ ID NO: 4) | Activity[a,b] | Stability[c] | Product Tolerance[d,e] |
| | Y113L; A133R; R146L; W147K; V153S; K163L; V177L; R211K; P233T; A235P; P244T; M294V; P318D; A323T; S324G; T391A; C424V; F427Y | V383A; A424V | | | |
| 143/144 | A9T; G18A; D21H; V31M; N45H; F86Y; R88L; A133R; R146L; W147K; V153S; K163L; V177L; R211K; P233T; A235P; P244T; M294V; P318D; A323T; S324G; A383V; T391A; C424A; F427Y | R88L; F163L | + | + | + |
| 145/146 | A9T; Y14V; G18A; D21H; H26R; V31M; N45H; F86Y; A133R; R146L; W147K; N148Q; V153S; K163I; V177L; R211K; P233T; A235P; P244T; S284A; M294V; P318D; A323T; S324G; T391A; S400G; S420N; C424A; F427Y | Y14V; H26R; N148Q; L163I; S284A; V383A; S400G; S420N | nd | + | ++ |
| 147/148 | A9T; Y14V; G18A; D21H; V31M; V33T; N45H; W57F; F86Y; Y113L; A133R; R146L; W147K; V153S; K163L; V177L; R211K; P233T; A235P; P244T; M294V; P318D; A323T; S324G; A383V; T391A; C424A; F427Y | Y14V; V33T; W57F; Y113L; F163L | + | + | nd |
| 149/150 | A9T; Y14V; G18A; D21H; V31M; N45H; W57F; F86Y; R88L; Y113L; A133R; R146L; W147K; N148Q; V153S; K163I; L173A; V177L; R211K; P233T; A235P; P244T; M294V; P318D; A323T; S324G; T391A; S400G; C424A; F427Y | Y14V; W57F; R88L; Y113L; N148Q; L163I; L173A; V383A; S400G | nd | + | nd |
| 151/152 | A9T; G18A; D21H; V31M; N45H; W57F; F86Y; A133R; R146L; W147K; V153S; K163L; V177L; R211K; P233T; A235P; P244T; M294V; P318D; A323T; S324G; A383V; T391A; C424A; F427Y | W57F; F163L | nd | + | + |
| 153/154 | A9T; Y14V; G18A; D21H; H26R; V31M; N45H; F86Y; A133R; R146L; W147K; V153S; K163L; V177L; R211K; P233T; A235P; P244T; S284A; M294V; P318D; A323T; S324H; A383V; T391A; S400G; C424A; F427Y | Y14V; H26R; F163L; S284A; G324H; S400G | + | + | nd |

[a]HTP Assay Condition 1: Cells grown in 96 well plates were lysed with 200 μL of Lysis Buffer (1 mg/mL lysozyme, 0.5 mg/mL polymyxin B sulfate, 1 mM PLP, 0.1M triethanolamine (TEA), pH 7.0). The reaction conditions comprised: 10 g/L (44.4 mM) compound (2); 1 mM pyridoxal-5-phosphate (PLP); 2M isopropylamine (IPM), pH 7.0; 100 mM triethanolamine (TEA), pH 7.0; 5% PEG 200 v/v; 10 μL Lysate; and 50° C. for 24 h.

[b]HTP Assay Condition 2: Cells grown in 96 well plates were lysed with 400 μL of Lysis Buffer (1 mg/mL lysozyme, 0.5 mg/mL polymyxin B sulfate, 1 mM PLP, 0.1M triethanolamine (TEA), pH 7.0. The reaction conditions comprised: 10 g/L (44.4 mM) compound (2); 1 mM pyridoxal-5-phosphate (PLP); 2M isopropylamine (IPM), pH 7.0; 100 mM triethanolamine (TEA), pH 7.0; 5% PEG 200 v/v; 10 μL Lysate; and 50° C. for 24 h.

[c]Stability Assay conditions: 10 g/L (44.4 mM) compound (2); 1 mM pyridoxal-5-phosphate (PLP); 2M isopropylamine (IPM), pH 7.0; 100 mM triethanolamine (TEA), pH 7.0; 5% PEG 200 v/v; 10 μL Lysate (prepared according to HTP Assay Condition 1 or 2); and 55° C. for 24 h. Lysates were prepared according to HTP Assay Condition 1 (for SEQ ID NO: 4-14) or HTP Assay Condition 2 (for SEQ ID NO: 16-154).

[d]Product Inhibition (i.e., Product Tolerance) Assay Condition 1: 10 g/L (44.4 mM) compound (2); 14 g/L compound (1); 1 mM pyridoxal-5-phosphate (PLP); 2M isopropylamine (IPM), pH 7.0; 100 mM triethanolamine (TEA), pH 7.0; 5% PEG 200 v/v; 10 μL Lysate; and 50° C. Lysates were prepared according to HTP Assay Condition 1.

[e]Product Inhibition (i.e., Product Tolerance) Assay Condition 2: 10 g/L (44.4 mM) compound (2); 16 g/L compound (1); 1 mM pyridoxal-5-phosphate (PLP); 2M isopropylamine (IPM), pH 7.0; 100 mM triethanolamine (TEA), pH 7.0; 5% PEG 200 v/v; 10 μL Lysate; and 50° C. Lysates were prepared according to HTP Assay Condition 2.

nd: not determined

TABLE 2B

Engineered Polypeptides and Relative Enzyme Improvements Using Shake Flask and DSP Preparations

| SEQ ID NO: | Active Mutations (relative to Wild-type of SEQ ID NO: 2) | Active Mutations (relative to SEQ ID NO: 4) | Shake Flask | | DSP | |
|---|---|---|---|---|---|---|
| | | | % ee | Activity[a] | % ee | Activity[b] |
| 1/2 | n/a | | nd | nd | nd | nd |
| 3/4 | A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; F427Y | | "Control" | "Control" | "Control" | "Control" |
| 5/6 | A9T; G18A; D21H; V31M; N45H; F86Y; A133R; R146L; W147K; V153S; K163L; V177L; R211K; P233T; A235P; P244T; M294V; P318D; A323T; S324G; A383V; T391A; C424A; F427Y; | F163L | 99.7 | + | nd | nd |
| 7/8 | A9T; G18A; D21H; V31M; N45H; F86Y; A133R; R146L; W147K; V153S; K163I; V177L; R211K; P233T; A235P; P244T; M294V; P318D; A323T; S324G; A383V; T391A; C424A; F427Y | F163I | 99.5 | + | nd | nd |
| 45/46 | A9T; Y14V; G18A; D21H; H26R; V31M; N45H; W57F; F86Y; R88L; Y113L; A133R; R146L; W147K; N148Q; V153S; K163I; V177L; R211K; P233T; A235P; P244T; M294V; P318D; A323T; S324G; A383V; T391A; C424A; F427Y | Y14V; H26R; W57F; R88L; Y113L; N148Q; L163I | 99.6 | + | 99.4 | + |
| 99/100 | A9T; G18A; D21H; V31S; N45H; W57F; F86Y; A133R; R146L; W147K; V153S; K163I; V177L; R211K; P233T; A235P; P244T; M294V; E315G; P318D; A323T; S324G; A346L; A383V; T391A; S398L; Q419S; C424A; F427Y | M31S; W57F; L163I; E315G; A346L; S398L; Q419S | 99.8 | + | nd | nd |
| 111/112 | A9T; Y14V; G18A; D21H; V31S; N45H; W57F; F86Y; A133R; R146L; W147K; V153S; K163L; V177L; R211K; P233T; A235P; P244T; M294V; I314N; P318D; A323T; S324G; A346L; A383V; T391A; S398V; C424A; F427Y | Y14V; M31S; W57F; F163L; I314N; A346L; S398V | 99.7 | + | nd | nd |
| 133/134 | A9T; Y14V; G18A; D21H; V31M; N45H; F86Y; Y113L; A133R; R146L; W147K; V153S; K163L; V177L; R211K; P233T; A235P; P244T; S284A; M294V; P318D; A323T; S324G; A383V; T391A; C424V; F427Y | Y14V; Y113L; F163L; S284A; A424V | nd | nd | 99.8 | + |
| 143/144 | A9T; G18A; D21H; V31M; N45H; F86Y; R88L; A133R; R146L; W147K; V153S; K163L; V177L; R211K; P233T; A235P; P244T; M294V; P318D; A323T; S324G; A383V; T391A; C424A; F427Y | R88L; F163L | 99 | nd | nd | nd |

[a]Shake Flask Assay Conditions: 25 g/L (or 50 or 100 g/L) compound (2); 1 mM pyridoxal-5-phosphate (PLP); 2M isopropylamine (IPM), pH 7.0; 5% v/v PEG200; 100 mM triethanolamine (TEA), pH 7.0; 2 g/L protein of transaminase-containing shake flask preparation; and 50° C. for a reaction time of 24 h.

[b]DSP Assay Conditions: 25 g/L (or 50 or 100 g/L) compound (2); 1 mM pyridoxal-5-phosphate (PLP); 2M isopropylamine (IPM), pH 7; 5% v/v PEG200; 100 mM triethanolamine (TEA), pH 7; 2 g/L protein from transaminase-containing DSP preparation; and 50° C. for a reaction time of 24 h.

From an inspection of the exemplary polypeptides, improvements in enzyme properties are associated with residue differences as compared to SEQ ID NO:4 at residue positions: X14; X26; X31; X33; X41; X47; X57; X70; X86; X88; X107; X113; X132; X148; X163; X168; X173; X203; X250; X284; X314; X315; X324; X346; X395; X398; X400; X417; X419; X420; X423; X424; X448; and X451. The specific residue differences at each of these positions that are associated with the improved properties include: X14V; X26R; X31S; X33T; X41L; X47N; X57F; X57Y;

X70A; X86D; X88A; X88L; X107P; X113L; X113V; X132F; X148Q; X148R; X163I; X163L; X163R; X163V; X168K; X168S; X173A; X203S; X250A; X284A; X314N; X315G; X324H; X346L; X395P; X398L; X398V; X398W; X400G; X417M; X419S; X420N; X423I; X424V; X448E; and X451D.

The specific enzyme properties associated with the residues differences as compared to SEQ ID NO:4 at the residue positions above include, among others, enzyme activity, stability, and product tolerance. Improvements in enzyme activity are associated with residue differences at residue positions: X14; X26; X31; X33; X41; X57; X70; X86; X88; X163; X168; X284; X314; X417; X419; X420; and X424. Improvements in enzyme stability are associated with residue differences at residue positions: X14; X26; X31; X33; X41; X57; X70; X86; X88; X163; X168; X284; X314; X324; X417; X419; X420; X423; and X424. Improvements in refractoriness to product inhibition (i.e., product tolerance) are associated with residue differences at residue positions: X26; X70; X86; X88; X113; X132; X163; X168; X314; X315; X395; X398; X417; and X419. As will be appreciated by the skilled artisan, residue differences at the foregoing residue positions have no significant deleterious effects on enzyme enantioselectivity, maintaining greater than 90% ee for compound (1), and typically resulting in enantioselectivities equal to or greater than 99% ee. Accordingly, the residue differences at the foregoing residue positions can be used individually or in various combinations to produce engineered transaminase polypeptides having the desired improved properties, including, among others, enzyme activity, stereoselectivity, stability, substrate tolerance, and refractoriness to product inhibition.

In light of the guidance provided herein, it is further contemplated that any of the exemplary engineered polypeptides of SEQ ID NO: 4, 6, 8, 10, 12, 14, 16, 18, 20, 22, 24, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 96, 98, 102, 104, 106, 108, 110, 114, 116, 122, 124, 126, 128, 130, 132, 136, 138, 140, 142, 144, 146, 148, 150, 152, and 154 can be used as the starting amino acid sequence for synthesizing other engineered transaminase polypeptides, for example by subsequent rounds of evolution by adding new combinations of various amino acid differences from other polypeptides in Tables 2A and 2B, and other residue positions described herein. Further improvements may be generated by including amino acid differences at residue positions that had been maintained as unchanged throughout earlier rounds of evolution.

Accordingly, in some embodiments, the engineered polypeptide having transaminase activity, is capable of converting substrate compound (2), 1-(1H-5-fluoro-6-chloro-indol-3-yl)propan-2-one, to the product compound (1), (S)-1-(1H-5-fluoro-6-chloro-indol-3-yl)propan-2-amine with improved properties as compared to SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, where the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M.

In some embodiments, the engineered transaminase polypeptide with improved properties as compared to SEQ ID NO:4 comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:4 and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the engineered transaminase polypeptides are capable converting substrate compound (2) to product compound (1) with the improved enantioselectivities described herein, e.g., ≥90% ee.

In some embodiments, the engineered polypeptide having transaminase activity with improved properties as compared to SEQ ID NO:4 comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, where the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the reference sequence is selected from SEQ ID NO: 4, 8, 14, 16, 132, 134, and 146. In some embodiments, the reference sequence is SEQ ID NO:4. In some embodiments, the reference sequence is SEQ ID NO:8. In some embodiments, the reference sequence is SEQ ID NO:134. In some embodiments, the reference sequence is SEQ ID NO:146.

In some embodiments, the engineered polypeptide having transaminase activity has an amino acid sequence comprising a sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and having one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, where the residue differences at residue positions X31; X57; X86; X163; X168; X314; X324; X398; and X417 are selected from: X31S; X57Y; X86D; X163I; X163L; X163R; X163V;

X168S; X314N; X324H; X398L; X398V; X398W; and X417M. In some embodiments, the amino acid sequence is selected from SEQ ID NO: 4, 8, 14, 16, 132, 134, and 146. In some embodiments, the amino acid sequence is SEQ ID NO:4. In some embodiments, the amino acid sequence is SEQ ID NO:8. In some embodiments, the amino acid sequence is SEQ ID NO:134. In some embodiments, the amino acid sequence is SEQ ID NO:146.

In some embodiments, the residue differences at residue positions X14; X26; X33; X41; X47; X70; X88; X107; X132; X148; X173; X203; X250; X284; X31S; X346; X395; X400; X419; X423; X448; and X451 are selected from X14V; X26R; X33T; X41L; X47N; X70A; X88A; X88L; X107P; X132F; X148Q; X148R; X173A; X203S; X250A; X284A; X315G; X346L; X395P; X400G; X419S; X423I; X448E; and X451D.

Accordingly, in some embodiments, the engineered transaminase polypeptides displaying one or more of the improved properties described herein can comprise an amino acid sequence having the amino acid sequence identity to a reference sequence, as described above, and one or more residue differences as compared to SEQ ID NO:4 selected from: X14V; X26R; X31S; X33T; X41L; X47N; X57Y; X70A; X86D; X88A; X88L; X107P; X132F; X148Q; X148R; X163I; X163L; X163R; X163V; X168S; X173A; X203S; X250A; X284A; X314N; X315G; X324H; X346L; X395P; X398L; X398V; X398W; X400G; X417M; X419S; X423I; X448E; and X451D.

In some embodiments, the engineered transaminase polypeptide having one or more residue differences as compared to SEQ ID NO:4 at residue positions X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451 above can further comprise one or more residue differences as compared to SEQ ID NO:4 selected from: X57F; X113L; X113V; X168K; X420N; and X424V.

In some embodiments, the engineered transaminase has an amino acid sequence comprising at least one or more residue differences as compared to SEQ ID NO:4 selected from: X86D; X284A; and X400G. In some embodiments, the residue differences comprise at least X86D. In some embodiments, the residue differences comprise at least X400G.

In some embodiments, the engineered transaminase has an amino acid sequence comprising at least one or more residue differences as compared to SEQ ID NO:4 selected from: X14V; X26R; X31S; X163I/L/R/V; X315G; and X398L/V/W. In some embodiments, the residue differences comprise at least X14V. In some embodiments, the residue differences comprise at least X163I/L/R/V. In some embodiments, the residue differences comprise at least X398L/V/W.

In some embodiments, the engineered transaminase polypeptide comprises an amino acid sequence having at least a combination of residues differences as compared to SEQ ID NO:4 selected from: X14V and X163I/L/V/H/R; X86D and X400G; X57F/Y and X163I/L/R/V; X57F/Y and X398L/V/W; X14V, X113L/V, X163I/L/R/V, X284A, and X424V; and X31S, X57F/Y, X163I/L/V/H/R, X315G, X346L, and X398V/L/W.

In some embodiments, the engineered transaminase polypeptide comprises an amino acid sequence having at least a combination of residues differences as compared to SEQ ID NO:4 selected from: X14V, X113L, X163L, X284A, and X424V; X14V, X26R, X163L, X284A, and X400G; X14V, X26R, X88L, and X113L; X57F, X163L, X168K, X314N, X315G, X346L, and X398V; X14V, X163L, X173A, X400G, and X420N; X14V, X113L, X163L, and X284A; X14V, X26R, X163L, X284A, and X400G; and X14V, X33T, X57F, X113L, and X163L.

As will be appreciated by the skilled artisan, in some embodiments, one or a combination of residue differences above that is selected can be conserved in the engineered transaminases as a core sequence (or feature), and additional residue differences at other residue positions incorporated into the core sequence to generate additional engineered transaminase polypeptides with improved properties. Accordingly, it is to be understood for any engineered transaminase containing one or a subset of the residue differences above, the present disclosure contemplates other engineered transaminases that comprise the one or subset of the residue differences, and additionally one or more residue differences at the other residue positions disclosed herein. By way of example and not limitation, an engineered transaminase comprising a residue difference at residue position X163, can further incorporate one or more residue differences at the other residue positions, e.g., X14; X26; X31; X33; X41; X47; X57; X70; X86; X88; X107; X132; X148; X168; X173; X203; X250; X284; X314; X315; X324; X346; X395; X398; X400; X417; X419; X423; X448; and X451. Another example is an engineered transaminase comprising a residue difference at residue position X14, which can further comprise one or more residue differences at the other residue positions, e.g., X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451. For each of the forgoing embodiments, the engineered transaminase can further comprise additional residue differences selected from: X57F; X113L; X113V; X168K; X420N; and X424V.

In some embodiments, the engineered transaminase polypeptide is capable of converting the substrate compound (2) to the product compound (1) with at least 1.2 fold, 1.5 fold, 2 fold, 3 fold, 4 fold, 5 fold, 10 fold, 20 fold, 30 fold, 40 fold, 50 fold or more activity relative to the activity of the reference polypeptide of SEQ ID NO: 4. In some embodiments, the engineered transaminase polypeptide capable of converting the substrate compound (2) to the product compound (1) with at least 1.2 fold, 1.5 fold, 2 fold, 3 fold, 4 fold, 5 fold, 10 fold, 20 fold 30 fold, 40 fold, 50 fold or more activity relative to the activity of the reference polypeptide of SEQ ID NO:4 comprises an amino acid sequence having one or more residue differences as compared to SEQ ID NO:4 selected from: X14V, X26R; X31S; X33T; X41L; X70A; X86D; X88A/L; X163I/L; X284A; and X419S.

In some embodiments, the engineered transaminase polypeptide capable of converting the substrate compound (2) to the product compound (1) with at least 1.2 fold the activity relative to SEQ ID NO:4 comprises an amino acid sequence selected from: SEQ ID NO: 6, 8, 10, 12, 14, 16, 22, 24, 28, 30, 32, 48, 52, 56, 62, 64, 66, 68, 86, 88, 90, 92, 98, 100, 104, 106, 108, 110, 112, 114, 116, 118, 124, 126, 128, 132, 134, 136, 142, 144, 148, and 154.

In some embodiments, the engineered transaminase polypeptide is capable of converting the substrate compound (2) to the product compound (1) with at least 5 fold the activity relative to SEQ ID NO:4 and comprises an amino acid sequence having one or more residue differences selected from: X14V, X26R; X33T; X88A/L; X163I/L; and X284A.

In some embodiments, the engineered transaminase polypeptide capable of converting the substrate compound (2) to the product compound (1) with at least 5 fold the activity relative to SEQ ID NO:4 comprises an amino acid sequence selected from: SEQ ID NO: 6, 8, 10, 14, 16, 22, 24, 28, 30, 32, 48, 52, 56, 62, 64, 86, 88, 90, 92, 98, 100, 104, 106, 108, 110, 112, 114, 116, 118, 124, 126, 128, 132, 134, 136, 142, 144, 148, and 154.

As noted above, in some embodiments, the engineered transaminase polypeptide displays increased refractoriness or resistance to inhibition by product amine (S)-1-(1H-5-fluoro-6-chloro-indol-3-yl)propan-2-amine as compared to the wild-type or a reference engineered enzyme (e.g., SEQ ID NO;4). The improved property of refractoriness or resistance to product inhibition (i.e., product tolerance) can be measured by measuring the activity of the evolved enzyme in presence of product compound and comparing it to the activity of the control enzyme in presence of product compound under the same reaction conditions. The refractoriness to product inhibition can be assessed by the fold increased enzyme activity. Measuring enzyme activity can be performed using standard biochemistry techniques, such as HPLC analysis, subtracting the background from the pre-added product amine. In some embodiments, the engineered transaminase polypeptide has at least 1.2 fold, 1.5 fold, 2 fold, 3 fold, 4 fold, 5 fold, or more refractoriness to inhibition by 1-(1H-5-fluoro-6-chloro-indol-3-yl)propan-2-amine, in particular (S)-1-(1H-5-fluoro-6-chloro-indol-3-yl) propan-2-amine, as compared to the polypeptide represented by SEQ ID NO:4 in the conversion of compound (2) to compound (1). Generally, the increased refractoriness or resistance to inhibition by the product compound can be measured under HTP assay conditions in presence of 14 g/L or 16 g/L of compound (1), as described in Table 2A and 2B and the Examples. In some embodiments, the engineered transaminase polypeptide having at least 1.2 fold or greater refractoriness to inhibition by 1-(1H-5-fluoro-6-chloro-indol-3-yl)propan-2-amine comprises an amino acid sequence having one or more residue differences as compared to SEQ ID NO:4 selected from: X26R; X70A; X86D; X88A/L; X132F; X163L; X315G; X395P; X398L; and X419S.

In some embodiments, the engineered transaminase polypeptide having at least 1.2 fold or greater refractoriness to inhibition by 1-(1H-5-fluoro-6-chloro-indol-3-yl)propan-2-amine, in particular (S)-1-(1H-5-fluoro-6-chloro-indol-3-yl) propan-2-amine, comprises an amino acid sequence selected from SEQ ID NO: 6, 12, 16, 18, 22, 24, 26, 28, 30, 32, 34, 36, 38, 40, 42, 46, 48, 52, 54, 56, 58, 60, 62, 74, 76, 98, 122, 124, 130, 132, 134, 138, 140, 144, 146, and 152.

In some embodiments, the engineered transaminase polypeptide has at least 5 fold or greater refractoriness to inhibition by 1-(1H-5-fluoro-6-chloro-indol-3-yl)propan-2-amine, in particular (S)-1-(1H-5-fluoro-6-chloro-indol-3-yl) propan-2-amine, and comprises an amino acid sequence having one or more residue differences as compared to SEQ ID NO:4 selected from: X26R; X88L; and X163L.

In some embodiments, the engineered transaminase polypeptide having at least 5 fold or greater refractoriness to inhibition by 1-(1H-5-fluoro-6-chloro-indol-3-yl)propan-2-amine, in particular (S)-1-(1H-5-fluoro-6-chloro-indol-3-yl) propan-2-amine, comprises an amino acid sequence having at least a combination of residue differences selected from: X14V, X113L, X163L, X284A, and X424V; X14V, X26R, X163L, X284A, and X400G; X14V, X26R, X88L, and X113L; X57F, X163L, X168K, X314N, X315G, X346L, and X398V; X14V, X163L, X173A, X400G, and X420N; X14V, X113L, X163L, and X284A; X14V, X26R, X163L, X284A, and X400G; and X14V, X33T, X57F, X113L, and X163L.

In some embodiments, the engineered transaminase polypeptide having at least 5 fold or greater refractoriness to inhibition by 1-(1H-5-fluoro-6-chloro-indol-3-yl)propan-2-amine as compared to SEQ ID NO:4 comprises an amino acid sequence selected from SEQ ID NO: 16, 124, 132, 134, 140, and 146.

In some embodiments, the engineered transaminase polypeptides have increased stability to temperature and/or solvents used in the conversion reaction as compared to the reference engineered transaminase of SEQ ID NO:4. In some embodiments, the engineered transaminase polypeptide has at least 1.2 fold, 1.5 fold, 2 fold, 3 fold, 4 fold, 5 fold, 10 fold or more stability under suitable reaction conditions, for example activity at 55° C. compared to activity at 50° C. under HTP Assay conditions. In some embodiments, the engineered transaminase polypeptide having at least 1.2 fold increased stability as compared to the polypeptide of SEQ ID NO:4 comprises an amino acid sequence having one or more residue differences as compared to SEQ ID NO:4 selected from: X14V; X26R; X31S; X33T; X41L; X70A; X86D; X88A/L; X163I/L/R/V; X284A; X324H; X419S; and X423I.

In some embodiments, the engineered transaminase polypeptide having at least 1.2 fold increased stability as compared to the polypeptide of SEQ ID NO:4 comprises an amino acid sequence selected from: 6, 8, 12, 16, 18, 20, 22, 24, 28, 30, 32, 34, 36, 38, 40, 42, 44, 46, 48, 50, 52, 56, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 132, 134, 136, 142, 144, 146, 148, 150, 152, and 154.

In some embodiments, the engineered transaminase polypeptide is capable of converting at least 90% or more, 91% or more, 92% or more, 93% or more, 94% or more, or 95% or more of compound (2) to compound (1) in 72 h or less, 48 h or less, or 24 or less, at a substrate loading of about 100 g/L, about 50 g/, or about 25 g/L under HTP Assay conditions, Shake Flask Assay conditions, or DSP Assay conditions. In some embodiments, the engineered transaminase polypeptide is capable of converting at least 90% or more of compound (2) to compound (1) in 24 or less at a substrate loading of about 25 g/L under HTP Assay conditions at 50° C. In some embodiments, the engineered transaminase polypeptide capable of converting at least 90% or more of compound (2) to compound (1) in 24 or less at a substrate loading of about 25 g/L under HTP Assay conditions at 50° C. comprises an amino acid sequence selected from: 124, 132, 134, 140, 144, and 146.

In some embodiments, the engineered polypeptide having transaminase activity, particularly in the conversion of substrate compound (2) to product compound (1), has an amino acid sequence comprising a sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154.

In some embodiments, the engineered transaminase having transaminase activity comprises an amino acid sequence having at least 80%, 85%, 86%, 87%, 88%, 89%, 90%, 91%, 92%, 93%, 94%, 95%, 96%, 97%, 98%, or 99% identity to one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and the amino acid residue differences as compared to SEQ ID NO:4 present in any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, as provided in Tables 2A and 2B.

In addition to the residue positions specified above, any of the engineered transaminase polypeptides disclosed herein can further comprise other residue differences relative to SEQ ID NO:2 or 4 at other residue positions, i.e., residue positions other than X9; X14; X18; X21; X26; X31; X33; X41; X45; X47; X57; X70; X86; X88; X107; X113; X132; X133; X146; X147; X148; X153; X163; X168; X173; X177; X203; X211; X233; X235; X244; X250; X284; X294; X314; X315; X318; X323; X324; X346; X383; X391; X395; X398; X400; X417; X419; X420; X423; X424; X427; X448; and X451. Residue differences at these other residue positions provide for additional variations in the amino acid sequence without adversely affecting the ability of the polypeptide to carry out the transaminase reaction, such as the conversion of compound (2) to compound (1) in enantiomeric excess. Accordingly, in some embodiments, in addition to the amino acid residue differences of any one of the engineered transaminase polypeptides selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, the sequence can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, or 1-50 residue differences at other amino acid residue positions as compared to the SEQ ID NO:4. In some embodiments, the number of amino acid residue differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45 or 50 residue positions. The residue difference at these other positions can include conservative changes or non-conservative changes. In some embodiments, the residue differences can comprise conservative substitutions and non-conservative substitutions as compared to the wild-type transaminase polypeptide of SEQ ID NO: 2 or the engineered transaminase polypeptide of SEQ ID NO:4.

Amino acid residue differences at other positions relative to the wild-type sequence of SEQ ID NO: 2 and the effect of these differences on enzyme function are described for other engineered transaminase polypeptides in patent publications WO2010081053, US20100209981, and WO2011159910; Yun et al., 2005, Appl Environ Micriobiol., 71(8):4220-4224); and Cho et al., 2008, Biotechnol Bioeng. 99(2):275-84; all of which are incorporated herein by reference. Accordingly, in some embodiments, one or more of the amino acid differences as compared to the sequence of SEQ ID NO: 2 or 4 can also be introduced into an engineered transaminase polypeptide of the present disclosure at residue positions selected from X4; X6; X12; X18; X30; X44; X56; X81; X82; X85; X95; X112; X122; X127; X130; X157; X164; X166; X167; X174; X181; X208; X228; X253; X256; X272; X285; X286; X293; X297; X302; X311; X312; X316; X317; X319; X320; X321; X332; X385; X407; X408; X409; X415; X418; X431; X434; X438; X444; and X446. In particular, the amino acid residues at the forgoing positions can be selected from the following: X4R/Q/L; X6R/I/N; X12A/G/K; X18A/V/L/I; X30A; X44A; X56V; X81D; X82H; X85A/S/V/T/N/C/G; X95T; X112I; X122E; X127L; X130G/M/A/V/L/I; X157T; X164N/Q/S/T/G/M/A/V/L/I; X166S; X167K/R; X174E/D; X181R; X208I; X228G/T; X253M; X256A; X272A; X285H; X286N/Q/S/T; X293N/Q/S/T; X297A; X302K; X311V; X312D/E; X316K/H/P; X317L/M/Y; X319Q/G/M/N/V; X320A/K; X321L/M/I; X332N/Q/S/T; X385R; X407S; X408A; X409G; X415M/L; X418V/N/Q/S/T; X431D; X434V; X438L; X444V; and X446V. Guidance on the choice of the amino acid residues at these residue positions and their effect on desirable enzyme properties can be found in the cited references.

In some embodiments, the present disclosure also provides engineered transaminase polypeptides that comprise a fragment of any of the engineered polypeptides described herein that retains the functional activity and/or improved property of that engineered transaminase. Accordingly, in some embodiments, the present disclosure provides a polypeptide fragment having transaminase activity, such as in converting compound (2) to compound (1) under suitable reaction conditions, wherein the fragment comprises at least about 80%, 90%, 95%, 96%, 97%, 98%, or 99% of a full-length amino acid sequence of an engineered transaminase polypeptide of the present disclosure, such as an exemplary engineered transaminase polypeptide selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154.

In some embodiments, the engineered transaminase polypeptide can have an amino acid sequence comprising a deletion of any one of the engineered transaminase polypeptides described herein, such as the exemplary engineered polypeptides of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154. Thus, for each and every embodiment of the engineered transaminase polypeptides of the disclosure, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the transaminase polypeptides, where the associated functional activity and/or improved properties of the engineered transaminase described herein is maintained. In some embodiments, the deletions can comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residues. In some embodiments, the number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residues. In some embodiments, the deletions can comprise deletions of 1, 2, 3, 4, 5, 6, 7, 8, 9, 10, 11, 12, 13, 14, 15, 16, 18, 20, 21, 22, 23, 24, or 25 amino acid residues.

In some embodiments, the engineered transaminase polypeptide herein can have an amino acid sequence comprising an insertion as compared to any one of the engineered transaminase polypeptides described herein, such as the exemplary engineered polypeptides of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154. Thus, for each and every embodiment of the transaminase polypeptides of the disclosure, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, 20 or more amino acids, 30 or more amino acids, 40 or more amino acids, or 50 or more amino acids, where the associated functional activity and/or improved properties of the engineered transaminase described herein is maintained. The insertions can be to amino or carboxy terminus, or internal portions of the transaminase polypeptide.

In some embodiments, the engineered transaminase polypeptide herein can have an amino acid sequence comprising a sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In some embodiments, the present disclosure provides an engineered polypeptide having transaminase activity, which polypeptide comprises an amino acid sequence having at least 80%, 85%, 86%, 87%, 88%, 89%, 90%, 91%, 92%, 93%, 94%, 95%, 96%, 97%, 98%, or 99% identity to a sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, with the proviso that the amino acid sequence is not identical to (that is, it excludes) any of the exemplary engineered transaminase polypeptide amino acid sequences disclosed in patent application publications WO2010081053, US20100209981, and WO2011159910; Yun et al., 2005, Appl Environ Micriobiol., 71(8):4220-4224); and Cho et al., 2008, Biotechnol Bioeng. 99(2):275-84; all of which are incorporated by reference herein.

In the above embodiments, the suitable reaction conditions for the engineered polypeptides can be those described in Table 2A and 2B. Accordingly, in some embodiments, the suitable reaction conditions are HTP Assay conditions, which comprise: 10 g/L (44.4 mM) compound (2); 1 mM pyridoxal-5-phosphate (PLP); 2 M isopropylamine (IPM), pH 7; 100 mM triethanolamine (TEA), pH 7; 5% v/v PEG200; 10 μL of HTP Lysate; and 50° C. for 24 h.

In some embodiments, the suitable reaction conditions are those described for shake flask powder (SFP) assays, which comprise: 25 g/L, 50 or 100 g/L compound (2); 1 mM pyridoxal-5-phosphate (PLP); 2 M isopropylamine (IPM), pH 7; 5% v/v PEG200; 100 mM triethanolamine (TEA), pH 7; 2 g/L protein from transaminase-containing shake flask preparation; and 50° C. for 24 h.

In some embodiments, the suitable reaction conditions are those described for downstream process powder (DSP) assays, which comprise: 25 g/L, 50 or 100 g/L compound (2); 1 mM pyridoxal-5-phosphate (PLP); 2 M isopropylamine (IPM), pH 7; 5% v/v PEG200; 100 mM triethanolamine (TEA), pH 7; 2 g/L protein from transaminase-containing DSP preparation; and 50° C. for 24 h.

Guidance for use of these foregoing reaction conditions and the transaminase polypeptides are given in, among others, Tables 2A and 2B and the Examples.

In some embodiments, the polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

It is to be understood that the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered transaminase polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having transaminase activity of the present disclosure can be immobilized on a solid support such that they retain their improved activity, stereoselectivity, and/or other improved properties relative to the reference polypeptide of SEQ ID NO: 4. In such embodiments, the immobilized polypeptides can facilitate the biocatalytic conversion of the substrate compounds of formula (II) or other suitable substrates, to the product compound of formula (I), or corresponding product (e.g., as shown in Schemes 1 and 2 described herein), and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the engineered transaminase polypeptides of the present disclosure can be carried out using the same engineered transaminase polypeptides bound or immobilized on a solid support.

Methods of enzyme immobilization are well-known in the art. The engineered transaminase polypeptide can be bound non-covalently or covalently. Various methods for conjugation and immobilization of enzymes to solid supports (e.g., resins, membranes, beads, glass, etc.) are well known in the art and described in e.g., Yi et al., "Covalent immobilization of ω-transaminase from *Vibrio fluvialis* JS17 on chitosan beads," *Process Biochemistry* 42(5): 895-898 (May 2007); Martin et al., "Characterization of free and immobilized (S)-aminotransferase for acetophenone production," *Applied Microbiology and Biotechnology* 76(4): 843-851 (September 2007); Koszelewski et al., "Immobilization of ω-transaminases by encapsulation in a sol-gel/celite matrix," *Journal of Molecular Catalysis B: Enzymatic,* 63: 39-44 (April 2010); Truppo et al., "Development of an Improved Immobilized CAL-B for the Enzymatic Resolution of a Key Intermediate to Odanacatib," *Organic Process Research & Development*, published online: dx.doi.org/10.1021/op200157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," *Biotechnology Progress* 18(3):629-34 (2002); and Bioconjugation Protocols: Strategies and Methods, In Methods in Molecular Biology, C. M. Niemeyer ed., Humana Press (2004); the disclosures of each which are incorporated by reference herein. Solid supports useful for immobilizing the engineered transaminases of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered transaminases of the present disclosure include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the polypeptide described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the polypeptides can be provided on the solid support in the form of an array in which the polypeptides are arranged in positionally distinct locations. The array can be used to test a variety of substrate compounds for conversion by the polypeptides. A plurality of supports can be configured on an array at various locations, addressable for robotic delivery of reagents, or by detection methods and/or instruments. Various methods for conjugation to substrates, e.g., membranes, beads, glass, etc. are described in, among others, Hermanson, G. T., Bioconjugate Techniques, $2^{nd}$ Edition, Academic Press; (2008), and Bioconjugation Protocols: Strategies and Methods, In Methods in Molecular Biology, C. M. Niemeyer ed., Humana Press (2004); the disclosures of which are incorporated herein by reference.

In some embodiments, the kits of the present disclosure include arrays comprising a plurality of different engineered ketoreductase polypeptides disclosed herein at different addressable position, wherein the different polypeptides are different variants of a reference sequence each having at least one different improved enzyme property. Such arrays comprising a plurality of engineered polypeptides and methods of their use are described in WO2009008908.

5.4 Polynucleotides Encoding Engineered Polypeptides, Expression Vectors and Host Cells In another aspect, the present disclosure provides polynucleotides encoding the engineered transaminase polypeptides described herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered transaminase can be introduced into appropriate host cells to express the corresponding transaminase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved transaminase enzymes. Thus, having knowledge of a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Tables 2A and 2B, and disclosed in the sequence listing incorporated by reference herein as SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154.

In various embodiments, the codons are preferably selected to fit the host cell in which the protein is being produced. For example, preferred codons used in bacteria are used for expression in bacteria; preferred codons used in yeast are used for expression in yeast; and preferred codons used in mammals are used for expression in mammalian cells. In some embodiments, all codons need not be replaced to optimize the codon usage of the transaminases since the natural sequence will comprise preferred codons and because use of preferred codons may not be required for all amino acid residues. Consequently, codon optimized polynucleotides encoding the transaminase enzymes may contain preferred codons at about 40%, 50%, 60%, 70%, 80%, or greater than 90% of codon positions of the full length coding region.

In some embodiments, as described above, the polynucleotide encodes an engineered polypeptide having transaminase activity with the properties disclosed herein, in particular the ability to convert substrate compound (2) to product compound (1) with improved properties as compared to SEQ ID NO:4, where the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the reference sequence is selected from SEQ ID NO: 4, 8, 14, 16, 132, 134, and 146. In some embodiments, the reference sequence is SEQ ID NO:4. In some embodiments, the reference sequence is SEQ ID NO:8. In some embodiments, the reference sequence is SEQ ID NO:134. In some embodiments, the reference sequence is SEQ ID NO:146.

In some embodiments, the polynucleotide encodes an engineered polypeptide having transaminase activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 or 4 and one or more residue differences as compared to SEQ ID NO: 4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M.

In some embodiments, the polynucleotide encodes an engineered polypeptide having transaminase activity, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 or 4 and at least a combination of residue differences as compared to SEQ ID NO: 4 selected from: X14V and X163I/L/R/V; X86D and X400G; X57F/Y and X163I/L/R/V; X57F/Y and X398L/V/W; X14V, X113L/V, X163I/L/R/V, X284A, and X424V; and X31S, X57F/Y, X163I/L/R/V, X315G, X346L, and X398L/V/W. In some embodiments, the combination of residue differences are selected from:

X14V, X113L, X163L, X284A, and X424V; X14V, X26R, X163L, X284A, and X400G; X14V, X26R, X88L, and X113L; X57F, X163L, X168K, X314N, X315G, X346L, and X398V; X14V, X163L, X173A, X400G, and X420N; X14V, X113L, X163L, and X284A; X14V, X26R, X163L, X284A, and X400G; and X14V, X33T, X57F, X113L, and X163L.

In some embodiments, the polynucleotide encodes an engineered polypeptide having transaminase activity, wherein the polypeptide comprises an amino acid sequence having at least 80%, 85%, 86%, 87%, 88%, 89%, 90%, 91%, 92%, 93%, 94%, 95%, 96%, 97%, 98%, or 99% identity to a reference polypeptide selected from any one of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, with the proviso that the amino acid sequence comprises any one of the set of residue differences as compared to SEQ ID NO: 4 contained in any one of the polypeptide sequences of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, as listed in Tables 2A and 2B.

In some embodiments, the polynucleotide encoding the engineered transaminase comprises a polynucleotide sequence selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, and 153.

In some embodiments, the polynucleotides are capable of hybridizing under highly stringent conditions to a reference polynucleotide sequence selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, and 153, or a complement thereof, and encodes a polypeptide having transaminase activity with one or more of the improved properties described herein. In some embodiments, the polynucleotide capable of hybridizing under highly stringent conditions encodes a transaminase polypeptide comprising an amino acid sequence that has one or more residue differences as compared to SEQ ID NO: 4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M.

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered transaminase. In some embodiments, the reference polynucleotide sequence is selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, and 153.

An isolated polynucleotide encoding any of the engineered transaminase polypeptides herein may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoter, leader sequence, polyadenylation sequence, propeptide sequence, signal peptide sequence, and transcription terminator. Suitable promoters can be selected based on the host cells used. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region which directs the expressed polypeptide into the secretory pathway of a host cell of choice may be used for expression of the engineered polypeptides. Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57:109-137. Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase.

The control sequence may also be a propeptide coding region that codes for an amino acid sequence positioned at the amino terminus of a polypeptide. The resultant polypeptide is referred to as a proenzyme or propolypeptide (or a zymogen in some cases). A propolypeptide can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

In another aspect, the present disclosure is also directed to a recombinant expression vector comprising a polynucleotide encoding an engineered transaminase polypeptide, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an Aspergillus cell include the amdS and pyrG genes of *Aspergillus nidulans* or *Aspergillus oryzae* and the bar gene of *Streptomyces hygroscopicus.*

In another aspect, the present disclosure provides a host cell comprising a polynucleotide encoding an engineered transaminase polypeptide of the present disclosure, the polynucleotide being operatively linked to one or more control sequences for expression of the transaminase enzyme in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, BHK, 293, and Bowes melanoma cells; and plant cells. An exemplary host cells are *Escherichia coli* W3110 (ΔfhuA) and BL21.

Accordingly, in another aspect, the present disclosure provides methods of manufacturing the engineered transaminase polypeptides, where the method can comprise culturing a host cell capable of expressing a polynucleotide encoding the engineered transaminase polypeptide under conditions suitable for expression of the polypeptide. The method can further comprise isolated or purifying the expressed transaminases polypeptide, as described herein.

Appropriate culture mediums and growth conditions for the above-described host cells are well known in the art. Polynucleotides for expression of the transaminase may be introduced into cells by various methods known in the art. Techniques include, among others, electroporation, biolistic particle bombardment, liposome mediated transfection, calcium chloride transfection, and protoplast fusion.

For the embodiments herein, the engineered polypeptides and corresponding polynucleotides can be obtained using methods used by those skilled in the art. The parental polynucleotide sequence encoding the wild-type polypeptide of *Vibrio fluvialis* is described in Shin et al., 2003, Appl. Microbiol. Biotechnol. 61(5-6):463-471, and methods of generating engineered transaminase polypeptides with improved stability and substrate recognition properties are disclosed in patent application publications WO2010081053 and US20100209981, incorporated herein by reference.

The engineered transaminases with the properties disclosed herein can be obtained by subjecting the polynucleotide encoding the naturally occurring or engineered transaminase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, "Oligonucleotide-directed random mutagenesis using the phosphorothioate method," In Methods Mol. Biol. 57:369-74; Smith, 1985, Ann. Rev. Genet. 19:423-462; Botstein et al., 1985, Science 229:1193-1201; Carter, 1986, Biochem. J. 237:1-7; Kramer et al., 1984, Cell, 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; Stemmer, 1994, Nature 370:389-391; Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. All publications are incorporated herein by reference.

The clones obtained following mutagenesis treatment can be screened for engineered transaminases having a desired improved enzyme property. For example, where the improved enzyme property desired is thermostability, enzyme activity may be measured after subjecting the enzyme preparations to a defined temperature and measuring the amount of enzyme activity remaining after heat treatments. Clones containing a polynucleotide encoding a transaminase are then isolated, sequenced to identify the nucleotide sequence changes (if any), and used to express the enzyme in a host cell. Measuring enzyme activity from the expression libraries can be performed using the standard biochemistry techniques, such as HPLC analysis following derivatization, e.g., with OPA, of the product amine.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors.

Accordingly, in some embodiments, a method for preparing the engineered transaminase polypeptide can comprise: (a) synthesizing a polynucleotide encoding a polypeptide comprising an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154 and having one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X31S; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M; and (b) expressing the transaminase polypeptide encoded by the polynucleotide.

In some embodiments of the method, the residue differences at residue positions X14; X26; X33; X41; X47; X70; X88; X107; X132; X148; X173; X203; X250; X284; X31S; X346; X395; X400; X419; X423; X448; and X451 are selected from X14V; X26R; X33T; X41L; X47N; X70A; X88A; X88L; X107P; X132F; X148Q; X148R; X173A; X203S; X250A; X284A; X315G; X346L; X395P; X400G; X419S; X423I; X448E; and X451D.

In some embodiments of the method, the amino acid sequence further comprises one or more residue differences selected from X57F; X113L; X113V; X168K; X420N; and X424V.

In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered transaminase can be measured for the desired improved property, e.g., activity, enantioselectivity, stability, and product tolerance, in the conversion of compound (2) to compound (1) by any of the assay conditions described herein.

In some embodiments, any of the engineered transaminase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are provided in Tables 2A and the Examples, and also commercially available, e.g., CelLytic B™ from Sigma-Aldrich of St. Louis Mo.

Chromatographic techniques for isolation of the transaminase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved transaminase enzymes. For affinity chromatography purification, any antibody which specifically binds the transaminase polypeptide may be used. For the production of antibodies, various host animals, including but not limited to rabbits, mice, rats, etc., may be immunized by injection with a transaminase polypeptide, or a fragment thereof. The transaminase polypeptide or fragment may be attached to a suitable carrier, such as BSA, by means of a side chain functional group or linkers attached to a side chain functional group.

5.7 Methods of Using the Engineered Transaminase Enzymes

In another aspect, the transaminases described herein can be used in a process for carrying out transaminase reactions in which an amino group from an amino donor is transferred to an amino acceptor, e.g., ketone substrate, to produce an amine Use of a prochiral ketone acceptor can result in the production of a chiral amine in enantiomeric excess. Generally, the process for performing the transamination reaction comprises contacting or incubating an amino donor and an amino acceptor with an engineered transaminase polypeptide of the disclosure under reaction conditions suitable for converting the amino acceptor to an amine.

In some embodiments, the transaminases can be used in the conversion of substrate compound of formula (II) to product compound of formula (I), as illustrated in Scheme 2:

Scheme 2

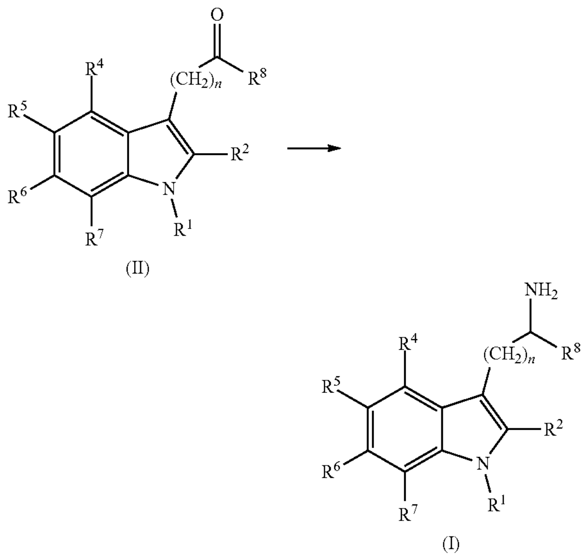

(II)

(I)

wherein $R^1$ is selected from the group consisting of hydrogen, carboxy, carboxy($C_1$-$C_6$)alkyl, optionally substituted ($C_1$-$C_6$)alkyl, optionally substituted ($C_2$-$C_6$)alkenyl, optionally substituted alkyloxycarbonyl, optionally substituted arylcarbonyl, optionally substituted arylsulfonyl, and a protecting group;

$R^2$ is selected from the group consisting of hydrogen, oxo, halo, hydroxy, amino, thio, optionally substituted ($C_1$-$C_6$) alkyl, ($C_1$-$C_6$)alkylamino, ($C_1$-$C_6$)dialkylamino, ($C_1$-$C_6$) alkylthio, ($C_1$-$C_6$)alkylsulfonyl, ($C_1$-$C_6$)alkylsulfinyl, and optionally substituted ($C_1$-$C_6$)alkyloxy;

$R^4$, $R^6$ and $R^7$ are each, independently of the others, selected from the group consisting of hydrogen, halo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$) alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl;

$R^5$ is selected from the group consisting of hydrogen, halo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$) alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$) alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl, or together with $R^4$ forms a 5 to 8 membered optionally substituted cycloalkyl or optionally substituted heterocyclic ring;

$R^8$ is selected from the group consisting of optionally substituted ($C_1$-$C_6$) alkyl, optionally substituted ($C_1$-$C_6$) alkyloxy, optionally substituted cycloalkyl, optionally substituted heterocycloalkyl, optionally substituted aryl, and optionally substituted heteroaryl, or together with $R^2$ forms an optionally substituted 5 to 8 membered cycloalkyl or heterocyclic ring; and n is 1 or 2;

with the provisos that (a) when $R^2$ is hydrogen, then at least one of the following applies:

(i) $R^1$ is not hydrogen, methyl, 4-(methyloxy)phenylcarbonyl-, 4-(trifluoromethyloxy)phenylsulfonyl-, 3-bromophenylcarbonyl-, 3-aminopropyl-, or 3-(methylcarbonylamino)propyl-;

(ii) $R^4$ and $R^7$ are each, independently of the other, not hydrogen or chloro;

(iii) $R^5$ is not hydrogen, hydroxy, methyl, methyloxy, fluoro, chloro, trifluoromethyl or cyano;

(iv) $R^6$ is not hydrogen, hydroxy, methyloxy, fluoro or chloro; or (v) $R^8$ is not methyl, ethyl, hydroxymethyl, carboxy, methyloxycarbonyl, ethyloxycarbonyl, or trifluoromethyl-; and (b) when n is 1, $R^2$ and $R^8$ together form a cyclohexyl ring, and $R^1$, $R^4$, $R^6$, and $R^7$ are hydrogen, then $R^5$ is not fluoro.

In some embodiments, the product compound of formula (I) above, and therefore the corresponding ketone substrate, i.e., compound of formula (II) below, have the following provisos:

(a) when $R^2$ is hydrogen, then at least one of the following applies:

(i) $R^1$ is not hydrogen, methyl, 4-(methyloxy)phenylcarbonyl-, 4-(trifluoromethyloxy)phenylsulfonyl-, 3-bromophenylcarbonyl-, 3-aminopropyl-, or 3-(methylcarbonylamino)propyl-;

(ii) $R^4$ and $R^7$ are each, independently of the other, not hydrogen or chloro;

(iii) $R^5$ is not hydrogen, hydroxy, methyl, methyloxy, fluoro, chloro, trifluoromethyl, or cyano;

(iv) $R^6$ is not hydrogen, hydroxy, methyloxy, fluoro or chloro; or (v) $R^8$ is not methyl, ethyl, hydroxymethyl, or trifluoromethyl-; and (b) when n is 1, $R^2$ and $R^8$ together form a cyclohexyl ring, and $R^1$, $R^4$, $R^6$, and $R^7$ are hydrogen, then $R^5$ is not fluoro.

Accordingly, specifically excluded from the compound of formula (I), and therefore the corresponding ketone substrate, i.e., compound of formula (II) below, are compounds of formula (I) in which $R^1$ is hydrogen, methyl, or

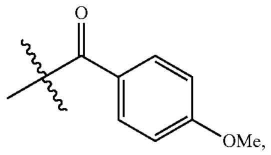

4-(methyloxy)phenylcarbonyl-

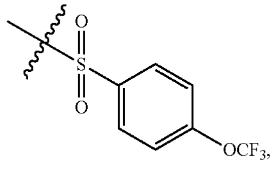

4-(trifluoromethyloxy) phenylsulfonyl-

-continued

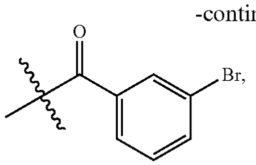

3-bromophenylcarbonyl-

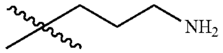
or 3-aminopropyl

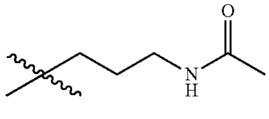
;

3-(methylcarbonylamino)propyl- $R^4$ and $R^7$ are each, independently of the other, hydrogen or chloro;

$R^5$ is hydrogen, hydroxy, methyl, methyloxy, fluoro, chloro, trifluoromethyl, or cyano;

$R^6$ is hydrogen, hydroxy, methyloxy, fluoro, or chloro;

$R^8$ is hydrogen, methyl, ethyl, hydroxymethyl, carboxy, methyloxycarbonyl (—$CO_2CH_3$), ethyloxycarbonyl-(—$CO_2CH_2CH_3$), or trifluoromethyl; and n is 1 or 2.

Accordingly, in some embodiments, a process for preparing product compound (I) can comprise contacting the substrate compound of formula (II)

(II)

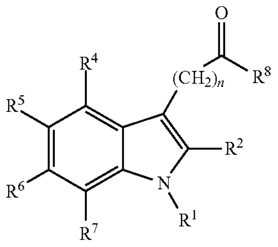

wherein $R^1$, $R^2$, $R^4$, $R^5$, $R^6$, $R^7$, $R^8$ and n are as defined above, in presence of an amino donor under suitable reaction conditions with an engineered transaminase polypeptide disclosed herein.

In some embodiments of the process, the compound of formula (I) comprises the compound of formula (IS), (IS)

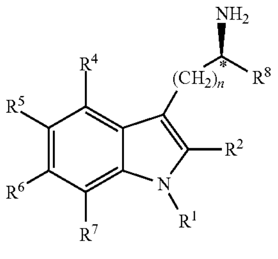

having the indicated stereochemistry at the carbon atom marked with an *, wherein the compound of formula (IS) is formed in enantiomeric excess. In some embodiments, compound of formula (IS) is formed in at least 90%, 91%, 92%, 93%, 94%, 95%, 96%, 97%, 98%, 99% or greater enantiomeric excess.

In some embodiments of the process, the compound of formula (I) above comprises the compound of formula (Ia):

(Ia)

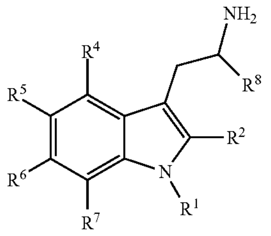

wherein $R^1$ is selected from the group consisting of hydrogen, carboxy, carboxy($C_1$-$C_6$)alkyl, optionally substituted ($C_1$-$C_6$)alkyl, optionally substituted ($C_2$-$C_6$)alkenyl, optionally substituted alkyloxycarbonyl, optionally substituted arylcarbonyl, optionally substituted arylsulfonyl, and a protecting group;

$R^2$ is selected from the group consisting of hydrogen, oxo, halo, hydroxy, amino, ($C_1$-$C_6$)alkylamino, ($C_1$-$C_6$)dialkylamino, optionally substituted ($C_1$-$C_6$)alkyl, and optionally substituted ($C_1$-$C_6$)alkyloxy;

$R^4$, $R^6$ and $R^7$ are each, independently of the others, selected from the group consisting of hydrogen, halo, hydroxy, hydroxy($C_1$-$C_6$)alkyl, amino, ($C_1$-$C_6$)alkylamino, ($C_1$-$C_6$)dialkylamino, cyano, nitro, sulfonyl, aminocarbonyl, aminocarbonyl($C_1$-$C_6$)alkyl, ($C_1$-$C_6$)alkylamino, carboxy, carboxy($C_1$-$C_6$)alkyl, optionally substituted ($C_1$-$C_6$) alkyl, optionally substituted($C_1$-$C_6$)alkyloxy, optionally substituted cycloalkyl, optionally substituted heterocycloalkyl, optionally substituted aryl, optionally substituted heteroaryl, alkylaminosulfonyl($C_1$-$C_6$)alkyl, arylsulfonyl($C_1$-$C_6$)alkyl, and heteroarylsulfonyl($C_1$-$C_6$)alkyl;

$R^5$ is selected from the group consisting of hydrogen, halo, hydroxy, hydroxy($C_1$-$C_6$)alkyl, amino, ($C_1$-$C_6$)alkylamino, ($C_1$-$C_6$)dialkylamino, cyano, nitro, sulfonyl, aminocarbonyl, aminocarbonyl($C_1$-$C_6$)alkyl, ($C_1$-$C_6$)alkylamino, carboxy, carboxy($C_1$-$C_6$)alkyl, optionally substituted ($C_1$-$C_6$) alkyl, optionally substituted($C_1$-$C_6$)alkyloxy, optionally substituted cycloalkyl, optionally substituted heterocycloalkyl, optionally substituted aryl, optionally substituted heteroaryl, alkylaminosulfonyl($C_1$-$C_6$)alkyl, arylsulfonyl ($C_1$-$C_6$)alkyl, and heteroarylsulfonyl($C_1$-$C_6$)alkyl, or together with $R^4$ forms a 5 to 7 membered optionally substituted cycloalkyl or optionally substituted heterocyclic ring;

$R^8$ is selected from the group consisting of optionally substituted ($C_1$-$C_6$) alkyl, optionally substituted ($C_1$-$C_6$) alkyloxy, optionally substituted cycloalkyl, optionally substituted heterocycloalkyl, optionally substituted aryl and optionally substituted heteroaryl;

with the proviso that when $R^2$ is hydrogen, then at least one of the following applies:

(i) $R^1$ is not hydrogen, methyl, 4-(methyloxy)phenylcarbonyl-, 4-(trifluoromethyloxy)phenylsulfonyl-, 3-bromophenylcarbonyl-, 3-aminopropyl-, or 3-(methylcarbonylamino)propyl-;

(ii) $R^4$ and $R^7$ are each, independently of the other, not hydrogen or chloro;

(iii) $R^5$ is not hydrogen, hydroxy, methyl, methyloxy, fluoro, chloro, trifluoromethyl or cyano;

(iv) $R^6$ is not hydrogen, hydroxy, methyloxy, fluoro or chloro; or (v) $R^8$ is not methyl, ethyl, hydroxymethyl-, or trifluoromethyl-.

Accordingly, in some embodiments, a process for preparing the compound of formula (Ia) comprises contacting the compound of formula (IIa)

(IIa)

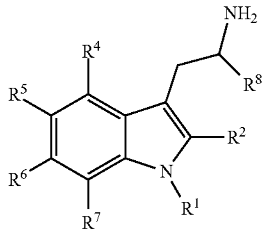

wherein $R^1$, $R^2$, $R^4$, $R^5$, $R^6$, $R^7$, and $R^8$ are as defined above, in presence of an amino donor under suitable reaction conditions with an engineered transaminase polypeptide disclosed herein.

In some embodiments of the process, the compound of formula (Ia) comprises the compound of formula (IaS)

(IaS)

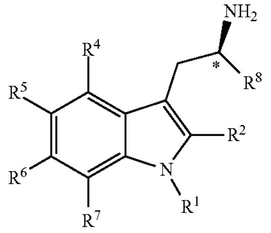

having the indicated stereochemistry at the carbon atom marked with an *, wherein compound (IaS) is formed in enantiomeric excess. In some embodiments, compound of formula (IaS) is formed in at least 90%, 91%, 92%, 93%, 94%, 95%, 96%, 97%, 98%, 99% or greater enantiomeric excess.

In some embodiments of the process, the compound of formula (I) above comprises the compound of formula (Ia1)

(Ia1)

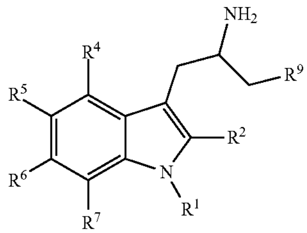

wherein $R^1$ is selected from the group consisting of hydrogen and $(C_1-C_6)$alkyl;

$R^2$ is selected from the group consisting of hydrogen, halo, and $(C_1-C_6)$alkyl;

$R^4$, $R^5$, $R^6$, and $R^7$ are each, independently of the others, selected from the group consisting of hydrogen, halo, hydroxy, optionally substituted $(C_1-C_6)$alkyl, hydroxy$(C_1-C_6)$alkyl, $(C_1-C_6)$alkyl; amino, $(C_1-C_6)$alkylamino, and $(C_1-C_6)$dialkylamino; and $R^9$ is selected from the group consisting of halo, hydroxy, hydroxy$(C_1-C_6)$alkyl, amino, $(C_1-C_6)$alkylamino, and $(C_1-C_6)$dialkylamino;

with the proviso that when $R^2$ is hydrogen, then at least one of the following applies:

(i) $R^1$ is not hydrogen or methyl;

(ii) $R^4$ and $R^7$ are each, independently of the other, not hydrogen or chloro;

(iii) $R^5$ is not hydrogen, hydroxy, methyl, methyloxy, fluoro, chloro, or trifluoromethyl;

(iv) $R^6$ is not hydrogen, hydroxy, methyloxy, fluoro or chloro; or (v) $R^9$ is not hydroxy.

Accordingly, in some embodiments, a process for preparing the compound of formula (Ia1) comprises contacting the compound of formula (IIa1)

(IIa1)

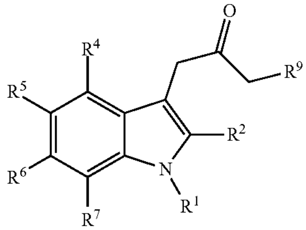

wherein $R^1$, $R^2$, $R^4$, $R^5$, $R^6$, $R^7$ and $R^9$ are as defined above, in presence of an amino donor under suitable reaction conditions with an engineered transaminase polypeptide disclosed herein.

In some embodiments of the process, the compound of formula (Ia) comprises the compound of formula (Ia2)

(Ia2)

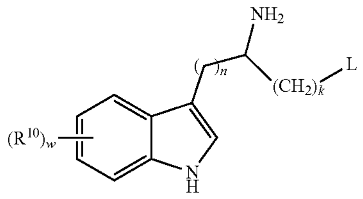

wherein

L is a leaving group;

each occurrence of $R^{10}$ is, independently of the others, selected from the group consisting of halo, hydroxy, amino, carboxy, cyano, nitro, thio, optionally substituted $(C_1-C_6)$ alkyl, hydroxy$(C_1-C_6)$alkyl, optionally substituted$(C_1-C_6)$ alkyloxy, optionally substituted $(C_1-C_6)$alkylamino, optionally substituted $(C_1-C_6)$dialkylamino, optionally substituted $(C_1-C_6)$alkylthio, optionally substituted $(C_1-C_6)$alkylsulfonyl, optionally substituted $(C_1-C_6)$alkylsulfinyl, carboxy $(C_1-C_6)$alkyl, $(C_1-C_6)$alkyloxycarbonyl, $(C_1-C_6)$alkylcarbonyloxy, optionally substituted aminocarbonyl, aminocarbonyl$(C_1-C_6)$alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$) alkyl;

k is an integer from 3 to 5;

n is 1 or 2; and w is an integer from 0 to 4.

In some embodiments of the compound of formula (Ia2), $R^{10}$ is selected from the group consisting of halo, hydroxy, hydroxy($C_1$-$C_6$)alkyl; amino, ($C_1$-$C_6$)alkylamino, ($C_1$-$C_6$) dialkylamino, optionally substituted ($C_1$-$C_6$)alkyl; optionally substituted ($C_1$-$C_6$)alkyloxy, alkylaminosulfonyl($C_1$-$C_6$)alkyl, arylsulfonyl($C_1$-$C_6$)alkyl, and heteroarylsulfonyl ($C_1$-$C_6$)alkyl.

Accordingly, in some embodiments, a process for preparing the compound of formula (Ia2) comprises contacting the compound of formula (IIa2), (IIa2)

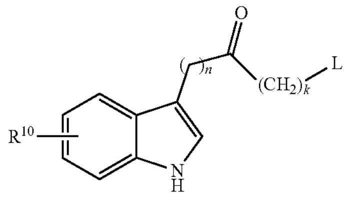

wherein

L, $R^{10}$, k, n and w are as defined above;

in presence of an amino donor under suitable reaction conditions with an engineered transaminase polypeptide disclosed herein.

The leaving group L can comprise any suitable group that can be replaced by the nucleophilic amino group. In some embodiments, L is selected from choro, bromo, alkyloxy, aryloxy, alkylcarbonyloxy, arylcarbonyloxy, alkythio, arylthio, and —$OPO_3$. In some embodiments, L is alkyloxy, wherein the alkyl group is selected from an optionally substituted methyl, ethyl, n-propyl, n-butyl, iso-butyl, sec-butyl, and tert-butyl. In some embodiments, L is chloro or bromo. In some embodiments, k is 3, 4, or 5.

As shown in Scheme 3, the presence of a leaving group L in the product compound of formula ((Ia2) permits cyclization of the product compound for preparing nitrogen containing heterocycles of structural formula (Ia3):

Scheme 3

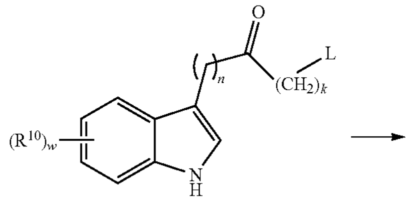

(IIa2)

-continued

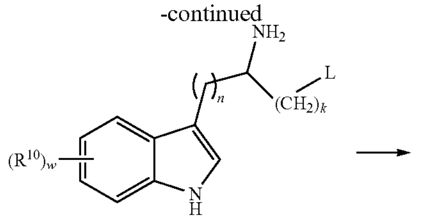

(Ia2)

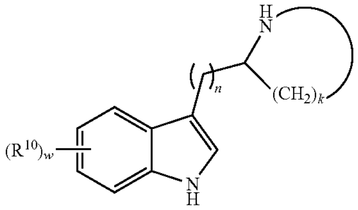

(Ia3)

Appropriate selection of the leaving group allows direct formation of compounds of structural formula (Ia3) under the reaction conditions of the transaminase reaction, thereby providing a facile method for synthesis of the heterocycle. Various substrate compounds within the scope of structural formula (IIa2) can be used to prepare the corresponding product compounds of structural formula (Ia2), which then serves as intermediates for preparing the heterocycles within the scope of structural formula (Ia3).

In some embodiments, the compound of formula (Ia3) comprises the compound of formula (Ia3'), which can be prepared by contacting the compound of formula (IIa2') with a transaminase of the disclosure to prepare the product compound of formula (Ia2'), as illustrated in Scheme 4:

Scheme 4

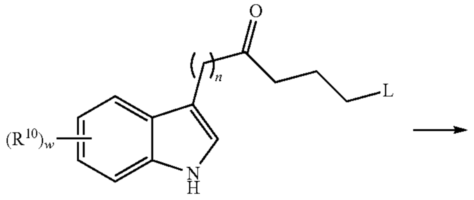

(IIa2')

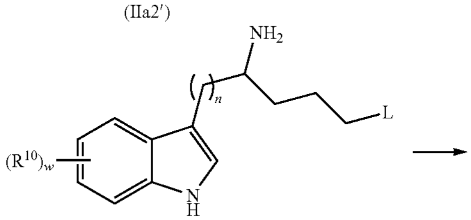

(Ia2')

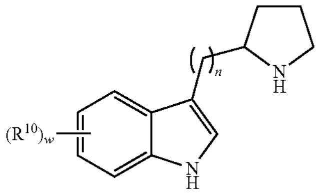

(Ia3')

wherein L, $R^{10}$, n and w are as defined for the compound of formula (Ia2). In some embodiments, L is chloro or bromo.

Cyclizing the compound of formula (Ia2') results in the compound of formula (Ia3'). In some embodiments, the cyclization can be carried under the reaction conditions of the transaminase reaction, or in some embodiments, separately after the termination of the transamination reaction.

In some embodiments of the process, the compound of formula (I) comprises the compound of formula (Ib), (Ib)

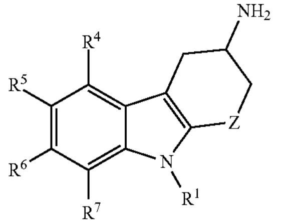

wherein

Z is selected from the group consisting of O, S, NH or $-(CH_2)_m-$, wherein m is 0, 1, 2 or 3;

$R^1$ is selected from the group consisting of hydrogen, carboxy, carboxy($C_1$-$C_6$)alkyl, optionally substituted ($C_1$-$C_6$)alkyl, optionally substituted ($C_2$-$C_6$)alkenyl, optionally substituted alkyloxycarbonyl, optionally substituted arylcarbonyl, optionally substituted arylsulfonyl, and a protecting group;

$R^4$, $R^5$, $R^6$ and $R^7$ are each, independently of the others, selected from the group consisting of hydrogen, halo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$)alkyl;

with the proviso that when Z is $-(CH_2)_m-$, m is 1, and $R^1$, $R^4$, $R^6$ and $R^7$ are hydrogen, then $R^5$ is not fluoro.

In some embodiments of the process for preparing the compounds of formula (IIb), Z is $-(CH_2)_m-$, wherein m is 1.

Accordingly, in some embodiments, a process for preparing the compound of formula (Ib) comprises contacting the compound of formula (IIb), (IIb)

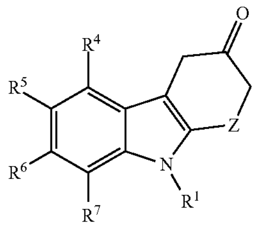

wherein wherein Z, $R^1$, $R^4$, $R^5$, $R^6$, and $R^7$ are as defined above;

in presence of an amino donor under suitable reaction conditions with an engineered transaminase polypeptide of the disclosure.

In some embodiments of the process, the compound of formula (Ib) comprises the compound of formula (IbS), (IbS)

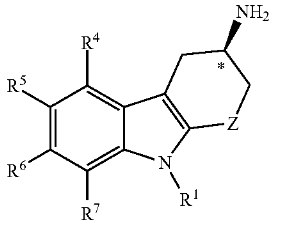

having the indicated stereochemistry at the carbon atom marked with an *, wherein compound (IbS) is formed in enantiomeric excess. In some embodiments, compound (IbS) is formed in at least 90%, 91%, 92%, 93%, 94%, 95%, 96%, 97%, 98%, 99% or greater enantiomeric excess.

In some embodiments of the process, the compound of formula (Ib) comprises the compound of formula (Ib1), (Ib1)

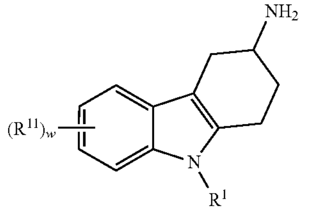

wherein $R^1$ is selected from the group consisting of hydrogen, carboxy($C_1$-$C_6$)alkyl, and ($C_1$-$C_6$)alkyl;

each occurrence of $R^{11}$ is, independently of the others, selected from the group consisting of chloro, bromo, iodo, hydroxy, amino, carboxy, cyano, nitro, thio, optionally substituted ($C_1$-$C_6$)alkyl, hydroxy($C_1$-$C_6$)alkyl, optionally substituted($C_1$-$C_6$)alkyloxy, optionally substituted ($C_1$-$C_6$)alkylamino, optionally substituted ($C_1$-$C_6$)dialkylamino, optionally substituted ($C_1$-$C_6$)alkylthio, optionally substituted ($C_1$-$C_6$)alkylsulfonyl, optionally substituted ($C_1$-$C_6$)alkylsulfinyl, carboxy($C_1$-$C_6$)alkyl, ($C_1$-$C_6$)alkyloxycarbonyl, ($C_1$-$C_6$)alkylcarbonyloxy, optionally substituted aminocarbonyl, aminocarbonyl($C_1$-$C_6$)alkyl, optionally substituted cycloalkyl, optionally substituted heterocycloalkyl, optionally substituted aryl, optionally substituted heteroaryl, optionally substituted aryloxy, optionally substituted acylamino, optionally substituted arylthio, optionally substituted arylsulfonyl, optionally substituted arylsulfinyl, optionally substituted aryloxycarbonyl, optionally substituted arylcarbonyloxy, optionally substituted heteroaryloxy, optionally substituted heteroarylamino, optionally substituted heteroarylthio, optionally substituted heteroarylsulfonyl, optionally substituted heteroarylsulfinyl, optionally substituted heteroaryloxycarbonyl, optionally substituted heteroarylcarbonyloxy, alkylaminosulfonyl($C_1$-$C_6$)alkyl, arylsulfonyl($C_1$-$C_6$)alkyl, and heteroarylsulfonyl($C_1$-$C_6$)alkyl; and w is an integer from 0 to 4.

In some embodiments of the compound of formula (Ib1), $R^{11}$ is selected from the group consisting of amino, aminocarbonyl, and aminocarbonyl($C_1$-$C_6$)alkyl.

Accordingly, a process for preparing the compound of formula (Ib1) comprises contacting the substrate compound of formula (Ib1),

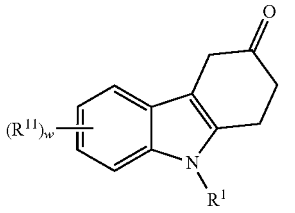

(Ib1)

wherein $R^1$, $R^{11}$ and w are as defined above;

in presence of an amino donor under suitable reaction conditions with an engineered transaminase polypeptide of the disclosure.

In some embodiments the process, the product compounds can be selected from the structures in Table 3, where the amine compound (i.e., Ia3, Ia4, Ia5, Ia6, Ia7, Ia8, Ia9, Ia10, Ia11, Ia12, Ia13, Ib2, Ib3, Ib4, Ib5 or Ib6) can be prepared by contacting the corresponding amino acceptor substrate compound (i.e., IIa3, IIa4, IIa5, IIa6, IIa7, IIa8, IIa9, IIa10, IIa11, IIa12, IIa13, IIb2, IIb3, IIb4, IIb5 or IIb6) with an engineered transaminase disclosed herein under suitable reaction conditions.

TABLE 3

| Substrate Compound | Product Compound | Chiral Product Compound |
|---|---|---|
| 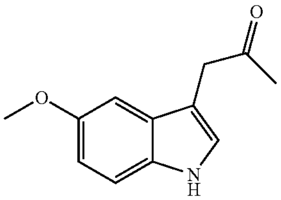 (IIa3) | 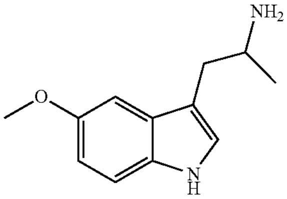 (Ia3) | 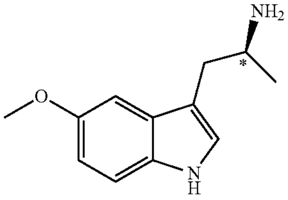 (Ia3S) |
| 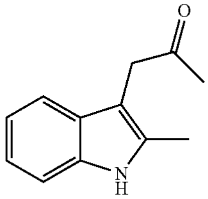 (IIa4) | 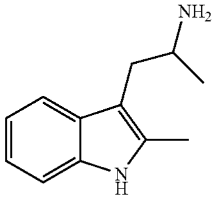 (Ia4) | 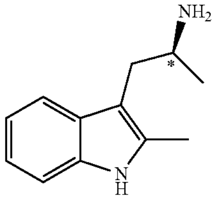 (Ia4S) |
| 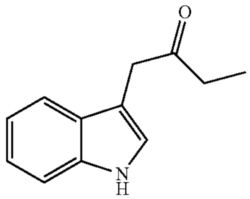 (IIa5) | 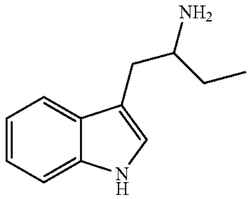 (Ia5) | 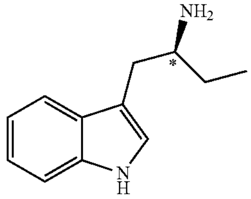 (Ia5S) |
| 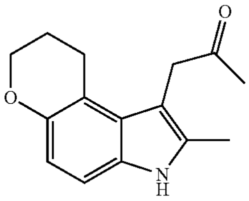 (IIa6) | 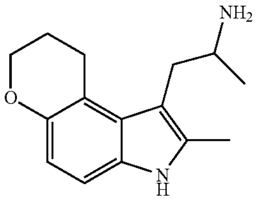 (Ia6) | 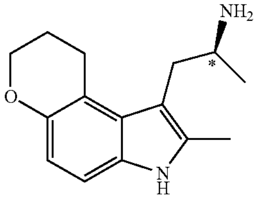 (Ia6S) |
| 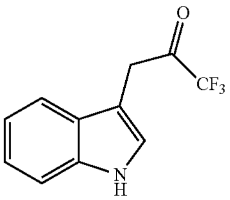 (IIa7) | 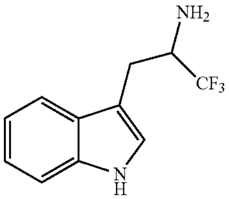 (Ia7) | 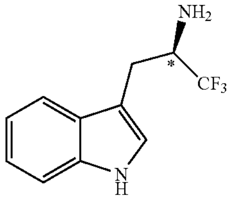 (Ia7S) |

TABLE 3-continued
| Substrate Compound | Product Compound | Chiral Product Compound |
|---|---|---|
| 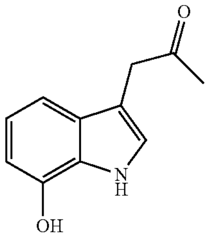<br>(IIa8) | 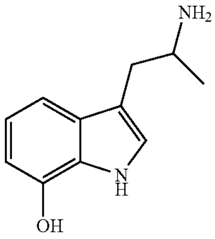<br>(Ia8) | 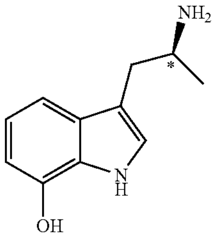<br>(Ia8S) |
| 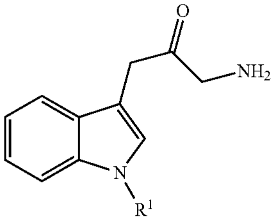<br>(IIa9) | 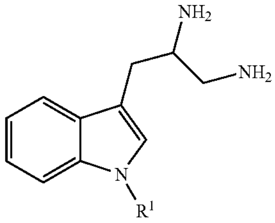<br>(Ia9) | 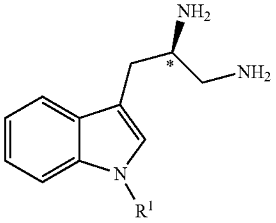<br>(Ia9S) |
| 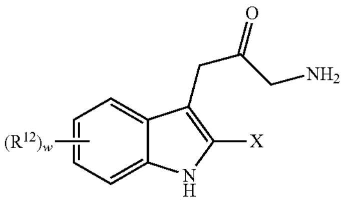<br>(IIa10) | 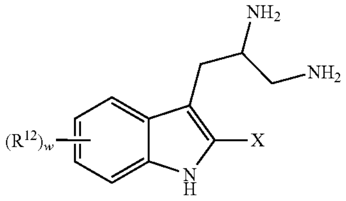<br>(Ia10) | 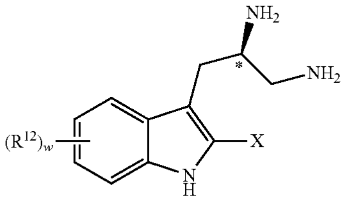<br>(Ia10S) |
| 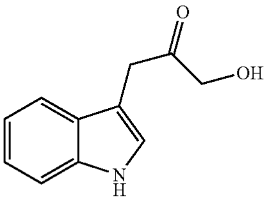<br>(IIa11) | 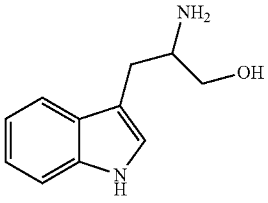<br>(Ia11) | 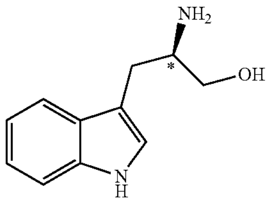<br>(Ia11S) |
| 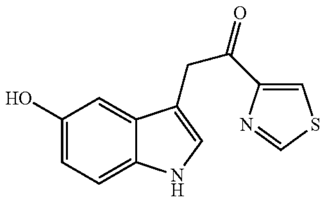<br>(IIa12) | 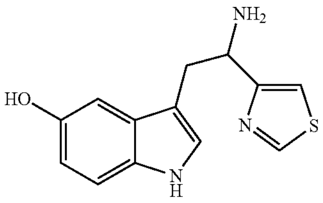<br>(Ia12) | 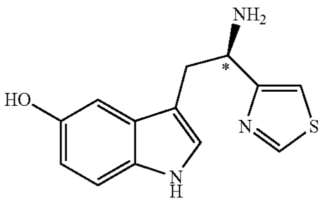<br>(Ia12S) |
| 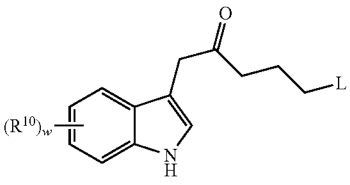<br>(IIa13) | 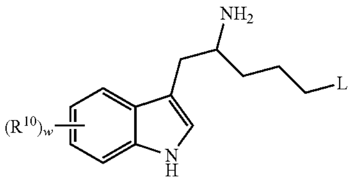<br>(Ia13) | 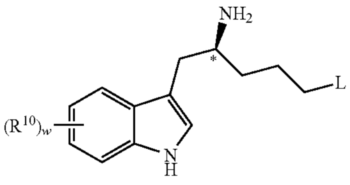<br>(Ia13S) |

TABLE 3-continued

| Substrate Compound | Product Compound | Chiral Product Compound |
|---|---|---|
| 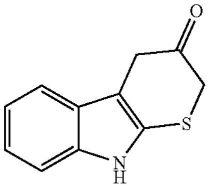 (IIb2) | 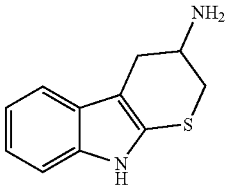 (Ib2) | 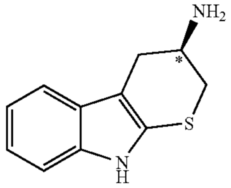 (Ib2S) |
| 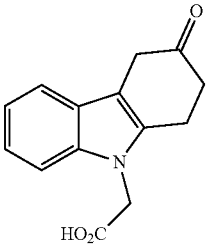 (IIb3) | 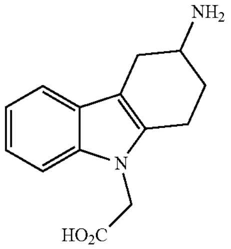 (Ib3) | 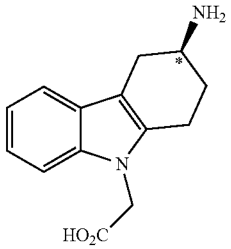 (Ib3S) |
| 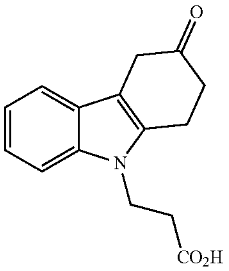 (IIb4) | 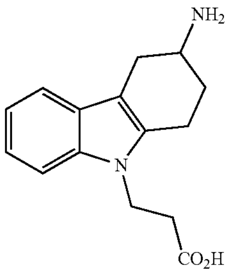 (Ib4) | 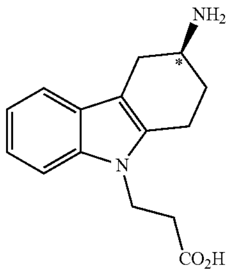 (Ib4S) |
| 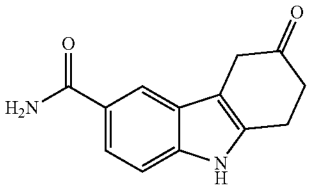 (IIb5) | 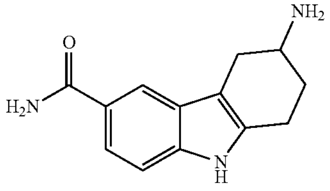 (Ib5) | 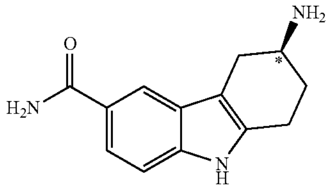 (Ib5S) |
| 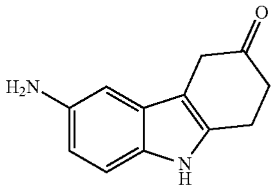 (IIb6) | 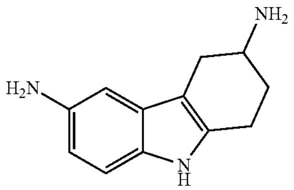 (Ib6) | 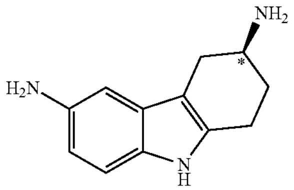 (Ib6S) |

For the compounds in Table 3, the following apply:

$R^1$ = hydrogen, carboxy, carboxy($C_1$-$C_6$)alkyl, or optionally substituted ($C_1$-$C_6$)alkyl.

$R^{10}$ = halo, hydroxy, hydroxy($C_1$-$C_6$)alkyl; amino, alkylamino, dialkylamino, optionally substituted ($C_1$-$C_6$)alkyl; optionally substituted ($C_1$-$C_6$)alkyloxy, alkylaminosulfonyl($C_1$-$C_6$)alkyl, arylsulfonyl($C_1$-$C_6$)alkyl, or heteroarylsulfonyl($C_1$-$C_6$)alkyl.

$R^{12}$ = halo, hydroxy, hydroxy($C_1$-$C_6$)alkyl, amino, ($C_1$-$C_6$)alkylamino, or ($C_1$-$C_6$)dialkylamino.

X = hydrogen, halo, or ($C_1$-$C_6$)alkyl.

L = Cl or Br w = 0, 1, 2, 3, or 4.

In view of the stereoselectivity of the engineered enzymes, in some embodiments, the process can be used to prepare chiral amine compounds in Table 3 (i.e., Ia3S, Ia4S, Ia5S, Ia6S, Ia7S, Ia8S, Ia9S, Ia10S, Ia11S, Ia12S, Ia13S, Ib2S, Ib3S, Ib4S, Ib5S, or Ib6S) with the stereochemistry at the carbon indicated with an * in enantiomeric excess. In some embodiments, the specific chiral compounds can be prepared in at least 90%, 91%, 92%, 93%, 94%, 95%, 96%, 97%, 98%, 99% or greater enantiomeric excess.

In some embodiments, the engineered transaminases can be used in preparing the compound of formula (1) with the indicated stereochemistry, (1)

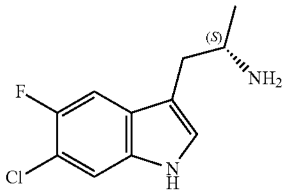

in enantiomeric excess. Accordingly, in some embodiments, a process for preparing the compound of formula (1) in enantiomeric excess comprises contacting the compound of formula (2)

(2)

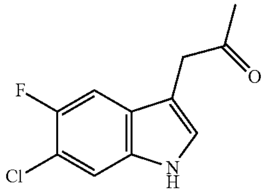

in presence of an amino donor under suitable reaction conditions with an engineered transaminase polypeptide described herein. In some embodiments of the process, the compound of formula (1) can be formed in at least 90%, 91%, 92%, 93%, 94%, 95%, 96%, 97%, 98%, 99% or greater enantiomeric excess.

For the embodiments herein, the prochiral ketone substrate compounds are available commercially or can be synthesized using methods available to the skilled artisan. For example, 1-(1H-indol-3-yl)-propan-2-one and 4-(1H-indol-3-yl)butan-2-one are commercially available. Substituted ketone substrates can be synthesized based on processes described in the art, for example, WO2009132921 and Pradhan et al., 2005, Synthetic Comm. 35:913-922. An exemplary process for synthesis of ketone substrates with substitutions on the indole is shown in Scheme 5, where $R^5$ are $R^6$ are hydrogen or halo (e.g., $R^5$ is F and $R^6$ is Cl):

Scheme 5

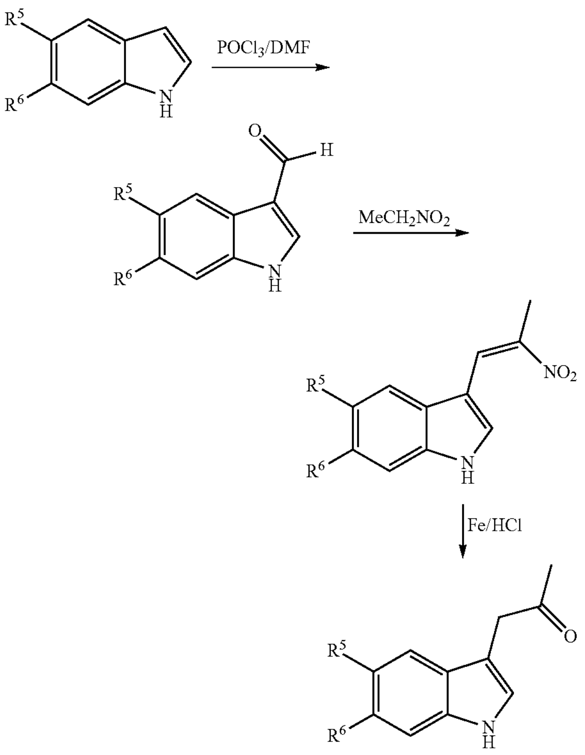

In Scheme 5, the substituted indole is reacted with phosphorous oxychloride to produce the indole-3-aldehyde, which is then converted to the substituted 3-(2-nitro-propenyl)-1H-indole with nitroethane. Oxidative hydrolysis of the nitroalkene to the corresponding ketone is accomplished with Fe—HCl (see Pradhan, supra). Alternatively, the nitroalkenes can be reduced with trialkylborohydrides and the resulting nitronate hydrolyzed to produce the ketone (see, e.g., Kabalka et al., 1999, Tetrahedron 46(21):7443-7457.

Another exemplary method for preparing the ketone substrates with substitutions on the indole is shown in Scheme 6:

Scheme 6

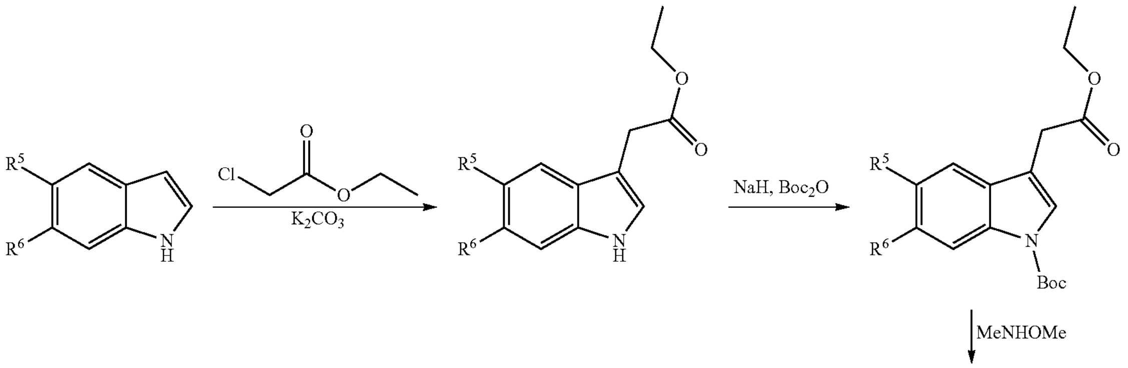

-continued

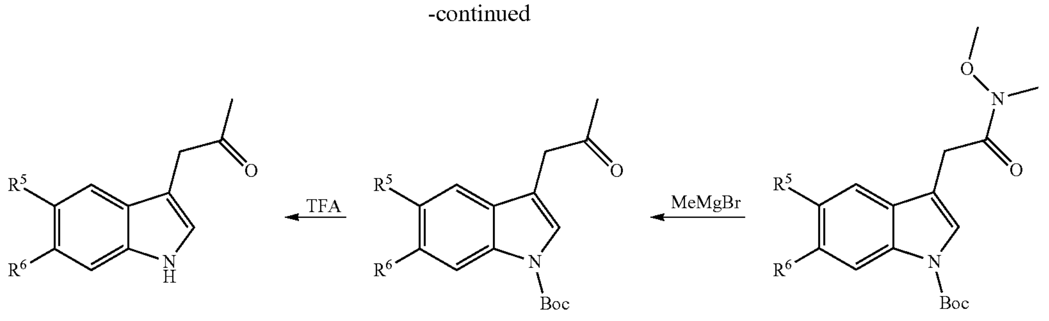

In Scheme 6, the substituted indole is reacted with ethylchloroacetate in presence of potassium carbonate to form the substituted ethyl-3-indoleacetate (see, e.g., Kumar et al., 2010, Oriental J Chem. 26(2):455-466). Protection of the indole nitrogen is followed by conversion to the Weinreb amide using N,O-dimethylhydroxylamine. Subsequent treatment with a Grignard reagent $CH_3$—MgBr or organolithium agent $CH_3$—Li results in the corresponding protected ketone. Acid-based deprotection yields the 5,6-substituted 1-(1H-indol-3-yl)-propan-2-one.

For the foregoing processes, any of the engineered transaminases described herein can be used. By way of example and without limitation, in some embodiments, the process can use an engineered transaminase polypeptide comprising an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154, and one or more residue differences as compared to SEQ ID NO:4 at residue positions selected from: X14; X26; X31; X33; X41; X47; X57; X70; X86; X88; X107; X132; X148; X163; X168; X173; X203; X250; X284; X314; X315; X324; X346; X395; X398; X400; X417; X419; X423; X448; and X451, wherein the residue differences at residue positions X31; X57; X86; X163; X168; X314; X324; X398; and X417 are selected from: X31S; X57Y; X86D; X163I; X163L; X163R; X163V; X168S; X314N; X324H; X398L; X398V; X398W; and X417M. In some embodiments, the reference sequence is selected from SEQ ID NO: 4, 8, 14, 16, 132, 134, and 146. In some embodiments, the reference sequence is SEQ ID NO:4. In some embodiments, the reference sequence is SEQ ID NO:8. In some embodiments, the reference sequence is SEQ ID NO:134. In some embodiments, the reference sequence is SEQ ID NO:146.

In some embodiments of the processes, the engineered transaminase polypeptide having one or more residue differences as compared to SEQ ID NO:4 at residue positions X14; X26; X31; X33; X41; X47; X57; X70; X86; X88; X107; X132; X148; X163; X168; X173; X203; X250; X284; X314; X31S; X324; X346; X395; X398; X400; X417; X419; X423; X448; and X451 above can further comprise one or more residue differences as compared to SEQ ID NO:4 selected from: X57F; X113L; X113V; X168K; X420N; and X424V.

In some embodiments, exemplary transaminases capable of carrying out the processes herein can be a polypeptide comprising an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, and 154. Guidance on the choice and use of the engineered transaminases is provided in the descriptions herein, for example Table 2 and the Examples.

In the embodiments herein and illustrated in the Examples, various ranges of suitable reaction conditions that can be used, including but not limited, to ranges of amino donor, pH, temperature, buffer, solvent system, substrate loading, polypeptide loading, cofactor loading, pressure, and reaction time. Further suitable reaction conditions for carrying out the process for biocatalytic conversion of substrate compounds to product compounds using an engineered transaminase polypeptide described herein can be readily optimized in view of the guidance provided herein by routine experimentation that includes, but is not limited to, contacting the engineered transaminase polypeptide and substrate compound under experimental reaction conditions of concentration, pH, temperature, solvent conditions, and detecting the product compound.

In some embodiments herein, the transaminase polypeptide uses an amino donor to form the product compounds. In some embodiments, the amino donor in the reaction condition can be selected from isopropylamine (also referred to herein as "IPM"), putrescine, L-lysine, α-phenethylamine, D-alanine, L-alanine, or D,L-alanine, or D,L-ornithine. In some embodiments, the amino donor is selected from IPM, putrescine, L-lysine, D- or L-alanine. In some embodiments, the amino donor is IPM. In some embodiments, the suitable reaction conditions comprise the amino donor, in particular IPM, present at a concentration of at least about 0.1 to about 3 M, 0.2 to about 2.5 M, about 0.5 to about 2 M or about 1 to about 2 M. In some embodiments, the amino donor is present at a concentration of about 0.1, 0.2, 0.3, 0.4, 0.5, 0.6, 0.7, 0.8, 1, 1.5, 2, 2.5 or 3 M. Higher concentrations of amino donor, e.g., IPM, can be used to shift the equilibrium towards amine product formation.

Suitable reaction conditions using the engineered transaminase polypeptides also typically comprise a cofactor. Cofactors useful for transaminase enzymes herein include, but are not limited to, pyridoxal-5'-phosphate (also known as pyridoxal-phosphate, PLP, P5P), pyridoxine (PN), pyridoxal (PL), pyridoxamine (PM), and their phosphorylated counterparts pyridoxine phosphate (PNP) and pyridoxamine phosphate (PMP). In some embodiments, the cofactor PLP is present naturally in the cell extract and does not need to be supplemented. In some embodiments of the processes, the suitable reaction conditions comprise exogenous cofactor added to the enzyme reaction mixture, for example, when using partially purified or purified transaminase enzyme. In some embodiments, the suitable reaction conditions can comprise the presence of a cofactor selected from PLP, PN, PL, PM, PNP, and PMP, at a concentration of about 0.1 g/L to about 10 g/L, about 0.2 g/L to about 5 g/L, about 0.5 g/L to about 2.5 g/L. In some embodiments, the reaction conditions comprise a PLP concentration of about 0.1 g/L or less, 0.2 g/L or less, 0.5 g/L or less, 1 g/L or less, 2.5 g/L or less, 5 g/L or less, or 10 g/L or less. In some embodiments, the cofactor can be added either at the beginning of the reaction and/or additional cofactor is added during the reaction.

Substrate compound in the reaction mixtures can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 200 g/L, 1 to about 200 g/L, about 5 to about 150 g/L, about 10 to about 100 g/L, about 20 to about 100 g/L, or about 50 to about 100 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L or at least about 200 g/L, or even greater. The values for substrate loadings provided herein are based on the molecular weight of compound (2), however it also contemplated that the equivalent molar amounts of various hydrates and salts of compound (2) also can be used in the process. In addition, substrates compounds covered by formulas (II), including compounds of formula (IIa) and (IIb), can also be used in appropriate amounts, in light of the amounts used for compound (2).

In carrying out the reactions described herein, the engineered transaminase polypeptide may be added to the reaction mixture in the form of a purified enzyme, whole cells transformed with gene(s) encoding the enzyme, and/or as cell extracts and/or lysates of such cells. Whole cells transformed with gene(s) encoding the engineered transaminase enzyme or cell extracts, lysates thereof, and isolated enzymes may be employed in a variety of different forms, including solid (e.g., lyophilized, spray-dried, and the like) or semisolid (e.g., a crude paste). The cell extracts or cell lysates may be partially purified by precipitation (ammonium sulfate, polyethyleneimine, heat treatment or the like), followed by a desalting procedure prior to lyophilization (e.g., ultrafiltration, dialysis, and the like). Any of the cell preparations may be stabilized by crosslinking using known crosslinking agents, such as, for example, glutaraldehyde, or immobilization to a solid phase (e.g., Eupergit C, and the like).

The gene(s) encoding the engineered transaminase polypeptides can be transformed into host cell separately or together into the same host cell. For example, in some embodiments one set of host cells can be transformed with gene(s) encoding one engineered transaminase polypeptide and another set can be transformed with gene(s) encoding another engineered transaminase polypeptide. Both sets of transformed cells can be utilized together in the reaction mixture in the form of whole cells, or in the form of lysates or extracts derived therefrom. In other embodiments, a host cell can be transformed with gene(s) encoding multiple engineered transaminase polypeptide. In some embodiments the engineered polypeptides can be expressed in the form of secreted polypeptides and the culture medium containing the secreted polypeptides can be used for the transaminase reaction.

The enhancements in activity and/or stereoselectivity of the engineered transaminase polypeptides disclosed herein provide for processes wherein higher percentage conversion can be achieved with lower concentrations of the engineered polypeptide. In some embodiments of the process, the suitable reaction conditions comprise an engineered polypeptide concentration of about 0.01 to about 50 g/L; about 0.05 to about 50 g/L; about 0.1 to about 40 g/L; about 1 to about 40 g/L; about 2 to about 40 g/L; about 5 to about 40 g/L; about 5 to about 30 g/L; about 0.1 to about 10 g/L; about 0.5 to about 10 g/L; about 1 to about 10 g/L; about 0.1 to about 5 g/L; about 0.5 to about 5 g/L; or about 0.1 to about 2 g/L. In some embodiments, the transaminase polypeptide is concentration at about 0.01, 0.05, 0.1, 0.2, 0.5, 1, 2, 5, 10, 15, 20, 25, 30, 35, 40, or 50 g/L.

During the course of the transamination reactions, the pH of the reaction mixture may change. The pH of the reaction mixture may be maintained at a desired pH or within a desired pH range. This may be done by adding an acid or base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, borate, carbonate, phosphate, triethanolamine (TEA), and the like. In some embodiments, the buffer is borate. In some embodiments of the process, the suitable reaction conditions comprise a buffer solution of TEA, where the TEA concentration is from about 0.01 to about 0.4 M, 0.05 to about 0.4 M, 0.1 to about 0.3 M, or about 0.1 to about 0.2 M. In some embodiments, the reaction condition comprises a TEA concentration of about 0.01, 0.02, 0.03, 0.04, 0.05, 0.07, 0.1, 0.12, 0.14, 0.16, 0.18, 0.2, 0.3, or 0.4 M. In some embodiments, the reaction conditions comprise water as a suitable solvent with no buffer present.

In the embodiments of the process, the reaction conditions can comprise a suitable pH. The desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH from about 6 to about 12, pH from about 6 to about 10, pH from about 6 to about 8, pH from about 7 to about 10, pH from about 7 to about 9, or pH from about 7 to about 8. In some embodiments, the reaction conditions comprise a solution pH of about 6, 6.5, 7, 7.5, 8, 8.5, 9, 9.5, 10, 10.5, 11, 11.5 or 12.

In the embodiments of the processes herein, a suitable temperature can be used for the reaction conditions, for example, taking into consideration the increased reaction rate at higher temperatures, and the activity of the enzyme during the reaction time period. For example, the engineered polypeptides of the present disclosure have increased stability relative to naturally occurring transaminase polypeptide e.g., the wild-type polypeptide of SEQ ID NO: 2, which allow the engineered polypeptides to be used at higher temperatures for increased conversion rates and improved substrate solubility characteristics. Accordingly, in some embodiments, the suitable reaction conditions comprise a temperature of about 10° C. to about 70° C., about 10° C. to about 65° C., about 15° C. to about 60° C., about 20° C. to about 60° C., about 20° C. to about 55° C., about 30° C. to about 55° C., or about 40° C. to about 50° C. In some embodiments, the suitable reaction conditions comprise a temperature of about 10° C., 15° C., 20° C., 25° C., 30° C., 35° C., 40° C., 45° C., 50° C., 55° C., 60° C., 65° C., or 70° C. In some embodiments, the temperature during the enzymatic reaction can be maintained at a temperature throughout the course of the reaction or adjusted over a temperature profile during the course of the reaction.

The processes herein are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the processes are generally carried out in an aqueous co-solvent system comprising an organic solvent (e.g., ethanol, isopropanol (IPA), dimethyl sulfoxide (DMSO), ethyl acetate, butyl acetate, 1-octanol, heptane, octane, methyl t-butyl ether (MTBE), toluene, and the like), ionic or polar solvents (e.g., 1 ethyl 4 methylimidazolium tetrafluoroborate, 1 butyl 3 methylimidazolium tetrafluoroborate, 1 butyl 3 methylimidazolium hexafluorophosphate, glycerol, polyethylene glycol, and the like). In some embodiments, the co-solvent can be a polar solvent, such as a polyol, dimethylsulfoxide, DMSO, or lower alcohol. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the transaminase enzyme under the reaction conditions. Appropriate co-solvent systems can be readily identified by measuring the enzymatic activity of the specified engineered transaminase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises a polymeric polyol solvent. Examples of suitable polyol solvents include, by way of example and not limitation, polyethylene glycol, polyethylene glycol methyl ether, diethylene glycol dimethyl ether, triethylene glycol dimethyl ether, and polypropylene glycol. In some embodiments, the aqueous co-solvent comprises polyethylene glycol, which is available in different molecular weights. Particularly useful are lower molecular weight polyethylene glycols, such as PEG200 to PEG600. Accordingly, in some embodiments, the aqueous co-solvent comprises PEG200 of about 1% to about 40% v/v; about 1% to about 40% v/v; about 2% to about 40% v/v; about 5% to about 40% v/v; 2% to about 30% v/v; 5% to about 30% v/v; 1 to about 20% v/v; about 2% to about 20% v/v; about 5% to about 20% v/v; about 1% to about 10% v/v; about 2% to about 10% v/v. In some embodiments, the suitable reaction conditions comprises an aqueous co-solvent comprising PEG200 at about 1%, 2%, 5%, 10%, 15%, 20%; 25%; 30%; 35%; 35% or about 40% v/v.

In some embodiments of the process, the suitable reaction conditions comprise an aqueous co-solvent, where the co-solvent comprises DMSO at about 1% to about 80% (v/v), about 1 to about 70% (v/v), about 2% to about 60% (v/v), about 5% to about 40% (v/v), 10% to about 40% (v/v), 10% to about 30% (v/v), or about 10% to about 20% (v/v). In some embodiments of the process, the suitable reaction conditions comprise an aqueous co-solvent comprising DMSO at least about 1%, 5%, 10%, 15%, 20%, 25%, 30%, 35%, 40%, 45%, 50%, 55%, 60%, 65%, 70%, 75%, or 80% (v/v).

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent.

The solid reactants (e.g., enzyme, salts, substrate compounds, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the transaminase and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase.

The transamination reaction is generally allowed to proceed until further conversion of ketone substrate to amine product does not change significantly with reaction time, e.g., less than 10% of substrate being converted, or less than 5% of substrate being converted). In some embodiments, the reaction is allowed to proceed until there is complete or near complete conversion of substrate ketone to product amine. Transformation of substrate to product can be monitored using known methods by detecting substrate and/or product. Suitable methods include gas chromatography, HPLC, and the like. Conversion yields of the chiral amine product generated in the reaction mixture are generally greater than about 50%, may also be greater than about 60%, may also be greater than about 70%, may also be greater than about 80%, may also be greater than 90%, and may be greater than about 97%. In some embodiments, the methods for preparing compound (2) using an engineered transaminase polypeptide under suitable reaction conditions results in at least about 91%, 92%, 93%, 94%, 95%, 96%, 97%, 98%, 99% or greater conversion of ketone substrate, e.g, compound of formula (II), to the amine product compound, e.g., compound of formula (I) in about 48 h or less, in about 36 h or less, in about 24 h or less, or even less time.

In some embodiments of the process, the suitable reaction conditions comprise a substrate loading of at least about 20 g/L, 30 g/L, 40 g/L, 50 g/L, 60 g/L, 70 g/L, 100 g/L, or more, and wherein the process results in at least about 91%, 92%, 93%, 94%, 95%, 96%, 97%, 98%, 99% or greater conversion of substrate compound to product compound in about 48 h or less, in about 36 h or less, or in about 24 h or less.

The engineered transaminase polypeptides of the present disclosure when used in the process under suitable reaction conditions result in an enantiomeric excess of the chiral amine in at least 90%. 91%. 92%, 93%, 94%, 95% 97%, 98, 99%, 99.1%, 99.2%, 99.3%, 99.4%, 99.5%, 99.6%, 99.7%, 99.8%, or 99.9%. e.e.

In a further embodiment of the processes, the suitable reaction conditions can comprise an initial substrate loading to the reaction solution which is then contacted by the polypeptide. This reaction solution is then further supplemented with additional substrate compound as a continuous addition over time at a rate of at least about 1 g/L/h, at least about 2 g/L/h, at least about 4 g/L/h, at least about 6 g/L/h, or higher. Thus, according to these suitable reaction conditions, polypeptide is added to a solution having an initial substrate loading of at least about 20 g/L, 30 g/L, or 40 g/L. This addition of polypeptide is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the process, the suitable reaction conditions comprise addition of the polypeptide to a solution having an initial substrate loading of at least about 20 g/L, 30 g/L, or 40 g/L followed by addition of further substrate to the solution at a rate of about 2 g/L/h, 4 g/L/h, or 6 g/L/h until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of ketone substrate to amine product of at least about 91%, 92%, 93%, 94%, 95%, 96%, 97%, 98%, 99% or greater. In some embodiments of this process, the further substrate added is in a solution comprising isopropylamine or isopropylamine acetate at a concentration of at least about 0.5 M, at least about 1.0 M, at least about 2.5 M, at least about 5.0 M, at least about 7.5 M, at least about 10.0 M.

In some embodiments of the processes, the transamination reaction can comprise the following suitable reaction conditions: (a) substrate loading at about 5 g/L to 200 g/L; (b) about 0.1 to 50 g/L of transaminase polypeptide; (c) about 0.1 to 4 M of isopropylamine (IPM); (d) about 0.1 to 10 g/L of pyridoxal phosphate (PLP) cofactor; (e) pH of about 6 to 9; and (f) temperature of about 30 to 60° C.

In some embodiments of the processes, the transamination reaction can comprise the following suitable reaction conditions: (a) substrate loading at about 5 to about 20 g/L; (b) about 0.05 to 2 g/L of transaminase polypeptide; (c) about 1 to 10% v/v of PEG200; (d) about 1 to 2 M of isopropylamine (IPM); (e) about 0.1 to 1 g/L of pyridoxal phosphate (PLP) cofactor; (f) about 0.1 to about 0.5 M of triethanolamine (TEA); (g) pH of about 6 to 8; and (h) temperature of about 45 to 55° C.

In some embodiments of the processes, the transamination reaction can comprise the following suitable reaction conditions: (a) substrate loading of about 25 to about 100 g/L; (b) about 0.5 to 10 g/L of transaminase polypeptide; (c) about 1 to 10% v/v of PEG200; (d) about 1 to 2 M of isopropylamine (IPM); (e) about 0.1 to 1 g/L of pyridoxal phosphate (PLP) cofactor; (f) about 0.1 to about 0.5 M of triethanolamine; (g) pH of about 6 to 8; and (h) temperature of about 45 to 55° C.

In some embodiments, additional reaction components or additional techniques carried out to supplement the reaction conditions. These can include taking measures to stabilize or prevent inactivation of the enzyme, reduce product inhibition, and/or shift reaction equilibrium to product amine formation.

Accordingly, in some embodiments of the process for preparing an amine, such as a chiral amine, additional quantities of the amino acceptor can be added (up to saturation) and/or the amino acceptor (ketone) formed can be continuously removed from the reaction mixture. For example, a solvent bridge or a two phase co-solvent system can be used to move the amine product to an extraction solution, and thereby reduce inhibition by amine product and also shift the equilibrium towards product formation (see, e.g., Yun and Kim, 2008, Biosci. Biotechnol. Biochem. 72(11):3030-3033).

In some embodiments of the processes, the suitable reaction conditions comprise the presence of the reduced cofactor, nicotinamide adenine dinucleotide (NADH), which can act to limit the inactivation of the transaminase enzyme (see e.g., van Ophem et al., 1998, Biochemistry 37(9):2879-88). In such embodiments where NADH is present, a cofactor regeneration system, such as glucose dehydrogenase (GDH) and glucose or formate dehydrogenase and formate can be used to regenerate the NADH in the reaction medium.

In some embodiments, the process can further comprise removal of the carbonyl by-product formed from the amino group donor when the amino group is transferred to the amino group acceptor. Such removal in situ can reduce the rate of the reverse reaction such that the forward reaction dominates and more substrate is then converted to product. Removal of the carbonyl by-product can be done in a number of ways. Where the amino group donor is an amino acid, such as alanine, the carbonyl by-product, a keto acid, can be removed by reaction with a peroxide (see, e.g., US 2008/0213845, incorporated herein by reference). Peroxides that can be used include, among others, hydrogen peroxide; peroxyacids (peracids), such as peracetic acid ($CH_3CO_3H$), trifluoroperacetic acid and metachloroperoxybenzoic acid; organic peroxides such as t-butyl peroxide ($(CH_3)_3COOH$); or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation by employing pyruvate decarboxylase (see, e.g., Höhne et al., 2008, Chem BioChem 9:363-365) or acetolactate synthase (see, e.g., Yun and Kim, supra).

Alternatively, in embodiments where an amino acid is used as amino group donor, the keto acid carbonyl by-product can be recycled back to the amino acid by reaction with ammonia and NADH using an appropriate dehydrogenase enzyme, e.g., amino acid dehydrogenase, in presence of an amine donor, such as ammonia, thereby replenishing the amino group donor.

In some embodiments, where the choice of the amino donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas. In some embodiments, the amino donor used in the process is isopropylamine (IPM), which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a transaminase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal and to maintain the pH of the reaction.

In further embodiments, any of the above described process for the conversion of substrate compound to product compound can also comprise one or more steps selected from: extraction, isolation, purification, and crystallization of product compound. Methods, techniques, and protocols for extracting, isolating, purifying, and/or crystallizing the product amine from biocatalytic reaction mixtures produced by the above disclosed methods are known to the ordinary artisan and/or accessed through routine experimentation. Additionally, illustrative methods are provided in the Examples below.

Various features and embodiments of the disclosure are illustrated in the following representative examples, which are intended to be illustrative, and not limiting.

6. EXAMPLES

Example 1: Synthesis, Optimization, and Screening Engineered Transaminase Polypeptides Gene Synthesis and Optimization:

The polynucleotide sequence encoding the reported wild-type ω-transaminase polypeptide from *Vibrio fluvialis* of SEQ ID NO: 2 was codon optimized and synthesized as the gene of SEQ ID NO: 1. The synthetic gene of SEQ ID NO: 1 was cloned into a pCK110900 vector system (see e.g., US Patent Application Publication 20060195947, which is hereby incorporated by reference herein) and subsequently expressed in *E. coli* W3110fhuA. The *E. coli* W3110 expresses the transaminase polypeptides as an intracellular protein under the control of the lac promoter. The polynucleotide (SEQ ID NO:3) encoding the engineered transaminase polypeptide of SEQ ID NO: 4 was obtained by directed evolution of the codon-optimized gene SEQ ID NO:1. The polypeptide of SEQ ID NO:4 has 24 amino acid residue differences (A9T; G18A; D21H; V31M; N45H; F86Y; A133R; R146L; W147K; V153S; K163F; V177L; R211K; P233T; A235P; P244T; M294V; P318D; A323T; S324G; A383V; T391A; C424A; and F427Y) relative to SEQ ID NO:2. This synthetic gene, SEQ ID NO: 3 (encoding the polypeptide of SEQ ID NO: 4), was used as the starting backbone for further optimization using standard methods of directed evolution via iterative variant library generation by gene synthesis followed by screening and sequencing of the hits to generate genes encoding engineered transaminases capable of converting compound (2) to compound (1) with enhanced enzyme properties relative to the polypeptides SEQ ID NOs: 2 and 4. The resulting engineered transaminase polypeptide sequences and specific mutations and relative activities are listed in Table 2A.

Example 2: Production of Engineered Transaminases

The engineered transaminase polypeptides were produced in host *E. coli*. W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic processes disclosed herein.

High-Throughput Growth and Expression.

Cells were picked and grown overnight in LB media containing 1% glucose and 30 μg/mL chloramphenicol (CAM) under culture conditions of 30° C., 200 rpm, and 85% humidity. A 20 μL aliquot of overnight growth were transferred to a deep well plate containing 380 μL 2× YT growth media containing 30 μg/mL CAM, 1 mM IPTG, and incubated for ~18 h at 30° C., 200 rpm, and 85% humidity. Subculture TB media was made up of TB media (380 μL/well), 30 μg/mL CAM, and 1 mM IPTG. Cell cultures were centrifuged at 4000 rpm, 4° C. for 10 min., and the media discarded. Cell pellets were resuspended in 250 or 4004 Lysis Buffer (0.1 M triethanolamine (TEA) buffer, pH 9.0, containing 400 μg/mL PMBS and 500 μg/mL Lysozyme), as described below.

Production of Shake Flask Powders (SFP).

A shake-flask procedure was used to generate engineered transaminase polypeptide powders used in secondary screening assays or in the biocatalytic processes disclosed herein. Shake flask powder (SFP) includes approximately 30% total protein and accordingly provide a more purified preparation of an engineered enzyme as compared to the cell lysate used in HTP assays. A single colony of *E. coli* containing a plasmid encoding an engineered transaminase of interest is inoculated into 50 mL Luria Bertani broth containing 30 μg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM $MgSO_4$) containing 30 μg/ml chloramphenicol, in a 1 liter flask to an optical density of 600 nm (OD600) of 0.2 and allowed to grow at 30° C. Expression of the transaminase gene is induced by addition of isopropyl-β-D-thiogalactoside ("IPTG") to a final concentration of 1 mM when the OD600 of the culture is 0.6 to 0.8. Incubation is then continued overnight (at least 16 hours). Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.0, and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 minutes, 4° C.). The clear lysate supernatant is collected and stored at −20° C. Lyophilization of frozen clear lysate provides a dry shake-flask powder of crude transaminase polypeptide. Alternatively, the cell pellet (before or after washing) can be stored at 4° C. or −80° C.

Production of Downstream Process (DSP) Powders:

DSP powders contain approximately 80% total protein and accordingly provide a more purified preparation of the engineered transaminase enzyme as compared to the cell lysate used in the high throughput assay. Larger-scale (~100-120 g) fermentation of the engineered transaminase for production of DSP powders can be carried out as a short batch followed by a fed batch process according to standard bioprocess methods. Briefly, transaminase expression is induced by addition of IPTG to a final concentration of 1 mM. Following fermentation, the cells are harvested and resuspended in 100 mM Triethanolamine-$H_2SO_4$ buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 3: Analytical Procedures

HPLC Analysis of HTP Reactions:

An aliquot of the quenched reaction was subject to HPLC analysis under the following conditions.

| | |
|---|---|
| Column | Mightysil RP-18 GP Aqua 150 × 4.6 mm, 5 μm |
| Temperature | 30° C. |
| Mobile Phase | Isocratic, 60% 20 mM $NH_4Ac$ (pH 6.6)/40% acetonitrile |
| Flow Rate | 2.5 mL/min |
| Detection Wavelength | 254 nm |
| Retention Times | Amine product compound (1): 0.96 min; Substrate Impurity: 1.8 min; Ketone substrate compound (2): 2.7 min |

Conversion of compound (2) to compound (1) was determined from the resulting chromatograms as follows:

Conversion (%)=Product Area/(Product Area+Substrate Area×0.73)×100%

HPLC Analysis of 5 mL and 100 mL Scale Reactions:

Aliquots of the quenched reaction was subject to HPLC analysis under the following conditions.

| | |
|---|---|
| Column | Mightysil RP-18 GP Aqua 250 × 4.6 mm, 5 □m |
| Temperature | 30° C. |
| Mobile Phase | Isocratic: 60% 20 mM $NH_4Ac$ (pH 6.6)/40% acetonitrile |
| Flow Rate | 2.0 mL/min |
| Detection | 254 nm |
| Retention Times | Amine product compound (1): 2.1 min Ketone substrate compound (2): 7.6 min |

Conversion of compound (2) to compound (1) was determined from the chromatograms as follows:

Conversion (%)=Product Area/(Product Area+Substrate Area×0.73)×100%

Determination of Product Chiral Purity (% Ee):

The chiral purity or enantiomeric excess of compound (1) was assessed by HPLC using the following conditions.

| | |
|---|---|
| Column | Astec Chirobiotic TAG column |
| Temperature | 15° C. |
| Mobile Phase | Methanol/Acetic acid/Triethylamine (100/0.2/0.1) |
| Flow Rate | 1.0 mL/min |
| Detection Wavelength | 225 nm |
| Retention Times | Ketone substrate: 3.6 min |

-continued

| | |
|---|---|
| | R-product: 17.9 min; S-product: 18.9 min |

Determination of Product Purity:

The purity of product was determined by HPLC using the following conditions.

| | | |
|---|---|---|
| Column | Mightysil Rp-18 GP aqua 250 × 4.6 mm, 5 μm | |
| Temperature | 30° C. | |
| Mobile Phase | Gradient. A: 20 mM $NH_4Ac$ (pH 6.6); B: acetonitrile | |
| | Time | Composition |
| | 0 min | 5% B |
| | 1.5 min | 5% B |
| | 35 min | 70% B |
| | 40 min | 70% B |
| | 45 min | 5% B |
| | 60 min | 5% B |
| Flow Rate | 1.5 mL/min | |
| Detection Wavelength | 254 nm | |
| Retention Times | Major impurity: 22.2 min; amine product: 17.5 min; ketone substrate: 25.4 min | |

Example 4: High Throughput (HTP) Screening of Transaminases for Conversion of Compound (2) to Compound (1)

HTP Screening Assays:

High-throughput screening used to guide primary selection of variants was carried out in 96-well plates using cell lysates under assay conditions of 10 g/L compound (2); 1 mM pyridoxal phosphate (PLP); 2 M isopropylamine (IPM), pH 7.0; 0.1 M triethanolamine (TEA), pH 7; 5% v/v PEG200; 10 μL lysate; and 50 or 55° C.

For preparing the lysates, cells were grown in 96-well plates as described above and lysates prepared by dispensing 250 μL (for Round 1) or 400 μL (for Round 2) of Lysis Buffer (1 mg/mL lysozyme, 0.5 mg/mL polymyxin B sulfate, 1 mM PLP, 0.1 M triethanolamine (TEA), pH 7.0) into each well. Plates were sealed, shaken for 2 h, and then centrifuged for 20 min at 4,000 rpm, 4° C. to pellet the cell debris.

A 10 μL of stock substrate solution (200 g/L compound (2) dissolved in PEG200) was added to each well of a 96-well plate followed by 180 μL of a stock solution of isopropylamine (IPM)/pyridoxal phosphate (PLP) (2.2 M IPM and 1.06 mM PLP in 100 mM TEA, pH 7.0). For assessing refractoriness to product compound (1) inhibition, compound (1) was added to the reaction mixture to a final 14 g/L for Round 1 assays and 16 g/L for Round 2 assays. Reactions were initiated by adding 10 μL of cell lysate/well. Plates were sealed and incubated with shaking at 50 or 55° C. for 24 h. Reactions were quenched with 600 μL of acetonitrile and samples examined by HPLC as described in Example 3.

Example 5: Process for Conversion of Compound (2) to Compound (1) in 5 mL Scale A 5 ml scale reaction was carried out as follows. To a 20 mL glass vial equipped with a cross-shaped magnetic stirring bar was added 0.75 mL (or 0.5 mL in case of 10% v/v PEG 200 concentration) of 100 mM TEA buffer (pH 7.0). 2 mL of 5 M IPM•HCl stock solution was added to the vial followed by 1 mL of 5 mM PLP stock solution. The mixture was stirred at 500 rpm (magnetic stirring). The pH of the mixture was then adjusted to 7 using 1 M NaOH solution. Solid substrate, 125 mg (or 250 mg for 50 g/L, or 500 mg for 100 g/L concentration), was then added to the vial. 0.25 mL (or 0.5 mL for 10% v/v) PEG 200 was then added to the mixture. Final concentrations of components were: 25 g/L (or 50 or 100 g/L) of compound (2); 1 mM PLP; 2 M IPM; 5% v/v (or 10%) PEG 200; 2 g/L transaminase preparation; and 100 mM TEA, pH 7.0. The mixture was then stirred and heated to 50° C.

Reactions were initiated by adding 1 mL of the enzyme stock solution (10 g/L). Aliquots of 20 μL were taken at different time points and diluted with 750 μL methanol and analyzed by HPLC. After 24 h, the reaction mixtures were quenched with 5 mL acetonitrile and samples analyzed by HPLC to get the final % conversion.

Example 6: Process for Conversion of Compound (2) to Compound (1) in 100 mL Scale A 100 mL scale reaction was carried out as follows. To a 250 mL round bottom flask with an anchor-shaped stirring blade was added 15 mL of 100 mM TEA buffer (pH 7). 40 mL of a 5 M IPM•HCl stock solution was added to the round bottom flask followed by 20 mL of the 5 mM PLP stock solution. The mixture was stirred at 100 rpm (overhead stirring) and the pH adjusted to 7 using 10 M NaOH. Solid substrate compound (2) was then added to the round bottom flask over ~5 min with stirring. PEG200 (5 mL) was then added and the mixture heated to 50° C. 20 mL of the enzyme stock solution (10 g/L) was then added to start the reaction. The reaction was stirred at 200 rpm (overhead stirring). Aliquots of 20 μL were taken at different time points and diluted with 750 μL methanol and analyzed by HPLC. In some cases, the reaction mixtures after 24 h were quenched with 100 mL acetonitrile and samples analyzed by HPLC to get the final % conversion. The final reaction conditions were: substrate compound (2), 25 g/L (or 50 or 100 g/L); 1 mM PLP; 2 M IPM; 5% v/v PEG200; 2 g/L of transaminase enzyme; and 100 mM TEA, pH 7. Conversion of substrate to product was analyzed by HPLC as described in Example 3.

Product Workup:

After 24 h reaction under the conditions described above, the reaction mixture was cooled to room temperature and then filtered through a standard G4 sintered glass funnel with a piece of filter paper (Whatman 1, pore size 11 μm). The round bottom flask was rinsed with 20 mL deionized water which was then filtered through the same funnel. The filtered cake was washed twice with 20 mL deionized water. The pH of the filtrate was adjusted from 6.8 to 3 using a 5 M HCl solution. The filtrate was then transferred into a separatory funnel and extracted with 100 mL MTBE. The biphasic mixture was allowed to separate. The MTBE layer containing unreacted substrate and impurities was discarded. The aqueous layer was transferred into a beaker, and 100 mL MTBE was added. The pH of the aqueous layer was adjusted from pH 3 to pH 10 using 10 M NaOH solution. The mixture was transferred into a separatory funnel and the phases allowed to separate. The aqueous layer was then extracted with 100 mL MTBE until product was not present in the aqueous layer (~three extractions). The MTBE phases from the extractions were combined and evaporated to dryness using a rotary evaporator. The crude product was further dried under vacuum for 48 h.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polypeptide having transaminase activity, comprising an amino acid sequence having at least 80% sequence identity to SEQ ID NO:2 and as compared to SEQ ID NO: 2 residue difference at residue X424V, X448E and X451D, and wherein said engineered polypeptide comprises an amino acid sequence having at least 90% sequence identity to SEQ ID NO:4, and wherein said engineered polypeptide comprises an amino acid sequence having one or more further residue differences as compared to SEQ ID NO:2 at residue positions selected from: X14, X26, X31, X33, X41, X47, X57, X70, X86, X88, X107, X132, X148, X168, X173, X203, X250, X284, X314, X315, X324, X346, X395, X398, X400, X417, X419 and, X423.

2. The engineered polypeptide of claim 1, wherein the amino acid sequence further comprises one or more residue differences selected from X383A and X420N.

3. The engineered polypeptide of claim 1, wherein the amino acid sequence further comprises at least one or more residue differences selected from X14V, X26R, X31S/D, X86D, X284A, X315G, X398L/V/W, and X400G.

4. The engineered polypeptide of claim 1, wherein the amino acid sequence comprises a combination of residue differences selected from:

X86D and X400G,

X57F/Y,

X57F/Y and X398L/V/W,

X31S, X57F/Y, X315G, X346L, and X398L/V/W

X14V, X284A, and X424V,
X14V, X26R, and X88L,
X57F, X168K, X314N, X315G, X346L, and X398V,
X14V, X173A, X400G, and X420N,
X14V, and X284A,
X14V, X26R, X284A, and X400G, and
X14V, X33T, and X57F.

5. The engineered polypeptide of claim 1, wherein said polypeptide is immobilized on a solid support.

* * * * *

SEQUENCE LISTING

```
<160> NUMBER OF SEQ ID NOS: 154

<210> SEQ ID NO 1
<211> LENGTH: 1362
<212> TYPE: DNA
<213> ORGANISM: Artificial Sequence
<220> FEATURE:
<223> OTHER INFORMATION: Codon optimized transaminase gene from Vibrio
      fluvialis

<400> SEQUENCE: 1

atgaacaaac cgcagagctg ggaagcgcgt gcggaaacct atagcctgta tggctttacc      60

gatatgccga gcctgcatca gcgtggcacc gtggtggtga cccatggcga aggcccgtat     120

atcgtggatg tgaacggccg tcgttatctg gatgcgaaca gcggcctgtg gaacatggtg     180

gcgggctttg atcataaagg cctgattgat gcggcgaaag cgcagtatga acgttttccg     240

ggctatcatg cgttttttgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatgcgg cggaaggcaa accgcagaaa     420

cgtaaaattc tgacccgttg gaacgcgtat catggcgtga ccgcggtgag cgcgagcatg     480
```

-continued

```
accggcaaac cgtataacag cgtgtttggc ctgccgctgc cgggctttgt gcatctgacc    540

tgcccgcatt attggcgtta tggcgaagaa ggcgaaaccg aagaacagtt tgtggcgcgt    600

ctggcccgtg aactggaaga aaccattcag cgtgaaggcg cggataccat tgcgggcttt    660

tttgcggaac cggtgatggg tgcgggcggt gttattccgc cggcgaaagg ctattttcag    720

gcgattctgc cgatcctgcg caaatatgat attccggtga tcagcgatga agtgatttgc    780

ggctttggcc gtaccggcaa cacctggggc tgcgtgacct atgattttac cccggatgcg    840

attattagca gcaaaaacct gaccgcgggt ttttttccga tgggcgcggt gattctgggt    900

ccggaactga gcaaacgtct ggaaaccgcg attgaagcga tcgaagaatt tccgcatggt    960

tttaccgcga gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gcattggctt tatgtgggcg   1140

ctggaagcgg tgaaagataa agcgagcaaa accccgtttg atggcaacct gagcgtgagc   1200

gaacgtattg cgaacacctg caccgatctg ggcctgattt gccgtccgct gggccagagc   1260

gtggttctgt gcccgccgtt tattctgacc gaagcgcaga tggatgaaat gttcgataaa   1320

ctggaaaaag cgctggataa agtgtttgcg gaagtggcgt aa                      1362
```

<210> SEQ ID NO 2
<211> LENGTH: 453
<212> TYPE: PRT
<213> ORGANISM: Vibrio fluvialis

<400> SEQUENCE: 2

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220
```

```
Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 3
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 3

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720
```

```
gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 4
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 4

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
```

-continued

```
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 5
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 5

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840
```

```
attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gcccgtttg atggcaacct gagcgtgagc    1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 6
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 6

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 7
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 7

```
atgaacaaac cgcagagctg ggaaacgcgt gcggaaacct atagcctgta tgcctttacc     60
cacatgccga gcctacatca gcgtggcacc atggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggcattc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
```

```
atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 8
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 8

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300
```

```
Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 9
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 9

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccgtc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140
```

```
ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 10
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 10

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Arg Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
```

```
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 11
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 11

atgaacaaac cgcagagctg ggaaacgcgt gcggaaacct atagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgtttgatgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga tcgaagaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gccccgtttg atggcaacct gagcgtgagc    1200

gaacgtattg cgaacacctg caccgatctg ggactgattt gccgaccgtt gggccagagc    1260

gtggttctgg caccgccgta cattctgacc gaagcgcaga tggatgaaat gttcgataaa    1320
```

```
ctggaaaaag cgctggataa agtgtttgcg gaagtggcgt aa                   1362


<210> SEQ ID NO 12
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 12

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350
```

-continued

```
Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 13
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 13

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcgtgc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                       1362
```

<210> SEQ ID NO 14

-continued

<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 14

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Val Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380
```

```
Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 15
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 15

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 16
<211> LENGTH: 453
<212> TYPE: PRT
<213> ORGANISM: Artificial Sequence
<220> FEATURE:
<223> OTHER INFORMATION: Engineered variant of V. fluvialis transaminase -continued

<400> SEQUENCE: 16

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
```

```
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 17
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 17

```
atgaacaaac cgcagagctg ggaaacgcgt gcggaaaccg tgagcctgta tgcctttacc     60
cacatgccga gcctacgtca gcgtggcacc atggtggtga cccatggcga aggcccgtat    120
atcgtggatg tgcatggccg tcgttatctg gatgcgaaca gcggcctgtt caacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                      1362
```

<210> SEQ ID NO 18
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 18

```
Met Asn Lys Pro Gln Ser Trp Glu Thr Arg Ala Glu Thr Val Ser Leu
1               5                   10                  15
```

-continued

```
Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430
```

-continued

```
Gln Met Asp Glu Met Phe Asp Lys Leu Glu Lys Ala Leu Asp Lys Val
        435                 440                 445

Phe Ala Glu Val Ala
    450


<210> SEQ ID NO 19
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 19

atgaacaaac cgcagagctg ggaaacgcgt gcggaaaccg tgagcctgta tgcctttacc     60

cacatgccga gcctacatca gcgtggcacc atggtgacca cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agagtttgcg gaagtggcgt aa                      1362


<210> SEQ ID NO 20
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 20

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Thr Thr His Gly Glu Gly Pro Tyr Ile Val Asp Val His Gly Arg Arg
```

-continued

```
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Glu
        435                 440                 445

Phe Ala Glu Val Ala
    450
```

<210> SEQ ID NO 21
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 21
atgaacaaac cgcagagctg ggaaacgcgt gcggaaaccg tgagcctgta tgcctttacc 60
cacatgccga gcctacgtca gcgtggcacc atggtggtaa cccatggcga aggcccgtat 120
atcgtggatg tgcatggccg tcgttatctg gatgcgaaca gcggcctgtg gaacatggtg 180
gcgggctttg atcataaagg cctgattgat gcggcgaaag cgcagtatga acgttttccg 240
ggctatcatg cgttttacgg cgccatgagc gatcagaccg tgatgctgtc tgaaaaactg 300
gtggaagtga gcccgtttga tagcggccgt gtgtttctga ccaacagcgg cagcgaagcg 360
aacgatacca tggtgaaaat gctgtggttt ctgcatcgtg cggaaggcaa accgcagaaa 420
cgtaaaattc tgaccctgaa gcaggcgtat catggctcca ccgcggtgag cgcgagcatg 480
accggcatcc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggccagtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gatttggggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gcccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 22
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 22

Met Asn Lys Pro Gln Ser Trp Glu Thr Arg Ala Glu Thr Val Ser Leu
1 5 10 15

Tyr Ala Phe Thr His Met Pro Ser Leu Arg Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Trp Asn Met Val Ala Gly Phe Asp
50 55 60

-continued

His Lys Gly Leu Ile Asp Ala Ala Lys Ala Gln Tyr Glu Arg Phe Pro
65 70 75 80

Gly Tyr His Ala Phe Tyr Gly Ala Met Ser Asp Gln Thr Val Met Leu
85 90 95

Ser Glu Lys Leu Val Glu Val Ser Pro Phe Asp Ser Gly Arg Val Phe
100 105 110

Leu Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Gln Ala Tyr His Gly Ser Thr Ala Val Ser Ala Ser Met
145 150 155 160

Thr Gly Ile Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Ser Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln
225 230 235 240

Ala Ile Leu Thr Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Glu Glu Phe Asp His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Leu Gly Gln Ser Val Val Leu Ala Pro Pro Tyr Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 23
<211> LENGTH: 1362
<212> TYPE: DNA

<213> ORGANISM: Artificial Sequence
<220> FEATURE:
<223> OTHER INFORMATION: Engineered variant of V. fluvialis transaminase

<400> SEQUENCE: 23

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gcaggcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agagtttgcg gaagtggcgt aa                       1362
```

<210> SEQ ID NO 24
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 24

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95
```

```
Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Glu
        435                 440                 445

Phe Ala Glu Val Ala
    450
```

<210> SEQ ID NO 25
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 25

-continued

```
atgaacaaac cgcagagctg ggaaacgcgt gcggaaaccg tgagcctgta tgcctttacc     60
cacatgccga gcctacatca gcgtggcacc atggtggtga cccatggcga aggcccgtat    120
atcgtggatg tgcatggccg tcgttatctg gatgcgaaca gcggcctgtg gaacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttga tagcggccgt gtgttttata ccaacagcgg cagcgaagcg    360
aacgatacca tggtgaaaat gctgtggttt ctgcatcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gatttttgggg   900
ccggaactga gcaaacgtct ggaaaccgcg attgaagcga tcgaagaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atggcaacct gagcgtgagc   1200
gaacgtattg cgaacacctg caccgatctg ggactgattt gccgaccgtt gggccagagc   1260
gtggttctgg caccgccgta cattctgacc gaagcgcaga tggatgaaat gttcgataaa   1320
ctggaaaaag cgctggataa agtgtttgcg gaagtggcgt aa                       1362
```

<210> SEQ ID NO 26
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 26

```
Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
```

```
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 27
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 27

atgaacaaac cgcagagctg ggaaacgcgt gcggaaaccg tgagcctgta tgcctttacc      60

cacatgccga gcctacgtca gcgtggcacc atggtggtga cccatggcga aggcccgtat     120
```

-continued

```
atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg cgccatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gcaggcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gatttttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 28
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 28

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Ala Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140
```

```
Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 29
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 29

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300
```

```
gtggaagtga gcccgtttga tagcggccgt gtgtttgtga ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 30
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 30

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Val Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175
```

```
Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 31
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 31

```
atgaacaaac cgcagagctg ggaaacgcgt gcggaaaccg tgagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgcatgagc gatcagaccg tgatgctgtc tgaaaaactg    300

gtggaagtga gcccgtttga tagcggccgt gtgtttgtga ccaacagcgg cagcgaagcg    360

aacgatacca tggtgaaaat gctgtggttt ctgcatcgtg cggaaggcaa accgcagaaa    420
```

cgtaaaattc tgaccctgaa gcaggcgtat catggctcca ccgcggtgag cgcgagcatg 480
accggccttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 32
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 32

Met Asn Lys Pro Gln Ser Trp Glu Thr Arg Ala Glu Thr Val Ser Leu
1 5 10 15

Tyr Ala Phe Thr His Met Pro Ser Leu His Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Arg Met Ser Asp Gln Thr Val Met Leu
85 90 95

Ser Glu Lys Leu Val Glu Val Ser Pro Phe Asp Ser Gly Arg Val Phe
100 105 110

Val Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Gln Ala Tyr His Gly Ser Thr Ala Val Ser Ala Ser Met
145 150 155 160

Thr Gly Leu Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr

```
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 33
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 33

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gcaggcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600
```

```
ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 34
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 34

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220
```

-continued

```
Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 35
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 35

```
atgaacaaac cgcagagctg ggaaacgcgt gcggaaaccg tgagcctgta tgcctttacc      60

cacatgccga gcctacgtca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggccttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720
```

-continued gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 36
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 36

Met Asn Lys Pro Gln Ser Trp Glu Thr Arg Ala Glu Thr Val Ser Leu
1 5 10 15

Tyr Ala Phe Thr His Met Pro Ser Leu Arg Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Trp Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Arg Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Leu Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln
225 230 235 240

Ala Ile Leu Thr Ile Leu Arg Lys Tyr Asp Ile Pro Val Ile Ser Asp
245 250 255

```
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 37
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 37

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgcatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac ccccggatgcg    840

attattagca gtaaaaacct aaccgcgggt ttttttccag taggagcggt gattttgggg    900
```

ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 38
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 38

Met Asn Lys Pro Gln Ser Trp Glu Thr Arg Ala Glu Thr Val Ser Leu
1 5 10 15

Tyr Ala Phe Thr His Met Pro Ser Leu Arg Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Arg Met Ser Asp Gln Thr Val Met Leu
85 90 95

Ser Glu Lys Leu Val Glu Val Ser Pro Phe Asp Ser Gly Arg Val Phe
100 105 110

Leu Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Leu Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln
225 230 235 240

Ala Ile Leu Thr Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr

```
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 39
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 39

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020
```

```
atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 40
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 40

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300
```

-continued

```
Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 41
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 41

atgaacaaac cgcagagctg ggaaacgcgt gcggaaaccg tgagcctgta tgcctttacc      60

cacatgccga gcctacgtca gcgtggcacc atggtggtga cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg cctgatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggcatcc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga tcgaagaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gccccgtttg atggcaacct gagcgtgagc    1200
```

```
gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 42
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 42

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335
```

```
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 43
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 43

atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgtttgtga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320
```

ctggaaaaag cgctggataa agtgtttgcg gaagtggcgt aa 1362

<210> SEQ ID NO 44
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 44

Met Asn Lys Pro Gln Ser Trp Glu Thr Arg Ala Glu Thr Val Ser Leu
1 5 10 15

Tyr Ala Phe Thr His Met Pro Ser Leu Arg Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Trp Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Arg Met Ser Asp Gln Thr Val Met Leu
85 90 95

Ser Glu Lys Leu Val Glu Val Ser Pro Phe Asp Ser Gly Arg Val Phe
100 105 110

Val Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Ile Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln
225 230 235 240

Ala Ile Leu Thr Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Glu Glu Phe Asp His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn

```
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 45
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 45

```
atgaacaaac cgcagagctg ggaaacgcgt gcggaaaccg tgagcctgta tgcctttacc     60

cacatgccga gcctacgtca gcgtggcacc atggtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gcaggcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 46
<211> LENGTH: 453

<212> TYPE: PRT
<213> ORGANISM: Artificial Sequence
<220> FEATURE:
<223> OTHER INFORMATION: Engineered variant of V. fluvialis transaminase

<400> SEQUENCE: 46

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380
```

-continued

```
Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 47
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 47
atgaacaaac cgcagagctg ggaaacgcgt gcggaaaccg tgagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg cctgatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gcaggcgtat catggctcca ccgcggtgag cgcgagcatg     480
accggcatcc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                      1362

<210> SEQ ID NO 48
<211> LENGTH: 453
<212> TYPE: PRT
<213> ORGANISM: Artificial Sequence
<220> FEATURE:
<223> OTHER INFORMATION: Engineered variant of V. fluvialis transaminase
```

<400> SEQUENCE: 48

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

```
Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 49
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 49

atgaacaaac cgcagagctg ggaaacgcgt gcggaaaccg tgagcctgta tgcctttacc      60

cacatgccga gcctacgtca gcgtggcacc atggtggtga cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg cctgatgagc gatcagaccg tgatgctgtc tgaaaaactg     300

gtggaagtga gcccgtttga tagcggccgt gtgtttgtga ccaacagcgg cagcgaagcg     360

aacgatacca tggtgaaaat gctgtggttt ctgcatcgtg cggaaggcaa accgcagaaa     420

cgtaaaattc tgaccctgaa gcgtgcgtat catggctcca ccgcggtgag cgcgagcatg     480

accggccttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga tcgaagaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gccccgtttg atggcaacct gagcgtgagc    1200

gaacgtattg cgaacacctg caccgatctg ggactgattt gccgaccgtt gggccagagc    1260

gtggttctgg caccgccgta cattctgacc gaagcgcaga tggatgaaat gttcgataaa    1320

ctggaaaaag cgctggataa agtgtttgcg gaagtggcgt aa                       1362


<210> SEQ ID NO 50
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 50

Met Asn Lys Pro Gln Ser Trp Glu Thr Arg Ala Glu Thr Val Ser Leu
1               5                   10                  15
```

-continued

```
Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Val Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Arg Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
```

```
        435                 440                 445

Phe Ala Glu Val Ala
    450


<210> SEQ ID NO 51
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 51

atgaacaaac cgcagagctg ggaaacgcgt gcggaaaccg tgagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgttttacgg cgccatgagc gatcagaccg tgatgctgtc tgaaaaactg     300

gtggaagtga gcccgtttga tagcggccgt gtgtttgtga ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggcatcc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gatttgggg      900

ccggaactga gcaaacgtct ggaaaccgcg attgaagcga tcgaagaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gcccgtttg atggcaacct gagcgtgagc     1200

gaacgtattg cgaacacctg caccgatctg ggactgattt gccgaccgtt gggccagagc    1260

gtggttctgg caccgccgta cattctgacc gaagcgcaga tggatgaaat gttcgataaa    1320

ctggaaaaag cgctggataa agtgtttgcg gaagtggcgt aa                       1362


<210> SEQ ID NO 52
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 52

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45
```

-continued

```
Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Ala Met Ser Asp Gln Thr Val Met Leu
                85                  90                  95

Ser Glu Lys Leu Val Glu Val Ser Pro Phe Asp Ser Gly Arg Val Phe
            100                 105                 110

Val Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 53
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 53

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgcatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgct attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gatttggggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 54
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 54

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
```

-continued

```
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Ala Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 55
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 55

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                       1362
```

<210> SEQ ID NO 56
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 56

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95
```

-continued

```
Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 57
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 57

```
atgaacaaac cgcagagctg ggaaacgcgt gcggaaaccg tgagcctgta tgcctttacc      60
cacatgccga gcctacatca gcgtggcacc atggtggtga cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg cgccatgagc gatcagaccg tgatgctgtc tgaaaaactg     300
gtggaagtga gcccgtttga tagcggccgt gtgtttctga ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 58
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 58

```
Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Ala Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125
```

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 59
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 59
atgaacaaac cgcagagctg ggaaacgcgt gcggaaaccg tgagcctgta tgcctttacc 60
cacatgccga gcctacgtca gcgtggcacc atggtggtga cccatggcga aggcccgtat 120
atcgtggatg tgcatggccg tcgttatctg gatgcgaaca gcggcctgtt caacatggtg 180

-continued

```
gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gcgtgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 60
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 60

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Arg Ala Tyr His Gly Ser Thr Ala Val Ser Ala Ser Met
```

-continued

```
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 61
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 61

```
atgaacaaac cgcagagctg ggaaacgcgt gcggaaaccg tgagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg ccgcatgagc gatcagaccg tgatgctgtc tgaaaaactg     300
```

```
gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

```
<210> SEQ ID NO 62
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 62

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175
```

-continued

```
Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

```
<210> SEQ ID NO 63
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 63

atgaacaaac cgcagagctg ggaaacgcgt gcggaaacct atagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgttttacgg cctgatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480
```

accggcatcc cgtataacag cgtgtttggc ctgccggctc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagcg ccaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgggt 1200
gaacgtattg cgaacacctg caccgatctg ggactgattt gtcgaccgat gggccagagc 1260
gtggttctgg tgccgccgta cattctgacc gaagcgcaga tggatgaaat gttcgataaa 1320
ctggaaaaag cgctggataa agtgtttgcg gaagtggcgt aa 1362

<210> SEQ ID NO 64
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 64

Met Asn Lys Pro Gln Ser Trp Glu Thr Arg Ala Glu Thr Tyr Ser Leu
1 5 10 15

Tyr Ala Phe Thr His Met Pro Ser Leu His Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Trp Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Leu Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Ile Pro Tyr Asn Ser Val Phe Gly Leu Pro Ala Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Met Gly Gln Ser Val Val Leu Val Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 65
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 65
atgaacaaac cgcagagctg ggaaacgcgt gcggaaacct atagcctgta tgcctttacc 60
cacatgccga gcctacatca gcgtggcacc atggtgacca cccatggcga aggcccgtat 120
atcgtggatg tgcatggccg tcgttatctg gatgcgaaca gcggcctgtg gaacatggtg 180
gcgggctttg atcataaagg cctgattgat gcggcgaaag cgcagtatga acgttttccg 240
ggctatcatg cgttttacgg cctgatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggctttc cgtataacag cgtgtttggc ctgccggctc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagcg ccaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagccg tgaaagataa agcgagcaaa gccccgtttg atggcaacct gagcgtgggt 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 66
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 66

Met Asn Lys Pro Gln Ser Trp Glu Thr Arg Ala Glu Thr Tyr Ser Leu
1 5 10 15

Tyr Ala Phe Thr His Met Pro Ser Leu His Gln Arg Gly Thr Met Val
20 25 30

Thr Thr His Gly Glu Gly Pro Tyr Ile Val Asp Val His Gly Arg Arg
35 40 45

Tyr Leu Asp Ala Asn Ser Gly Leu Trp Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Leu Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Phe Pro Tyr Asn Ser Val Phe Gly Leu Pro Ala Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln

```
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 67
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 67

```
atgaacaaac cgcagagctg ggaaacgcgt gcggaaacct atagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgtttgatgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggctttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780
```

-continued

```
ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacac acggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgggt   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 68
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 68

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255
```

```
Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 69
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 69

atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgtttgatgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggctttc cgtataacag caagtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900
```

-continued

```
ccggaactga gcaaacgtct ggaaaccgcg attgaagcga tcgaagaatt tgatcatggt    960

tttaccacac acggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagccg tgaaagataa agcgagcaaa gccccgtttg atggcaacct gagcgtgggt   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

```
<210> SEQ ID NO 70
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 70

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Lys Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285
```

```
Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 71
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 71

atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgtttgatgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggctttc cgtataacag cgtgtttggc ctgccggctc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960

tttaccacac acggccatcc ggtgggttgt gcgattgcgc tgaaagcgat tgatgtggtg   1020

atgaacgaag gcctggccga aaacgtgcgt cgtctggccc cgcgttttga agaacgtctg   1080
```

```
aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 72
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 72

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
```

-continued

```
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 73
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 73

atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgtttgatgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagccg tgaaagataa agcgagcaaa gccccgtttg atggcaacct gagcgtgggt   1200
```

```
gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 74
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 74

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335
```

-continued

```
Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 75
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 75

atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgtttgatgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggctttc cgtataacag cgtgtttggc ctgccggctc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgggt   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agagtttgcg gaagtggcgt aa                       1362
```

<210> SEQ ID NO 76
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 76

Met Asn Lys Pro Gln Ser Trp Glu Thr Arg Ala Glu Thr Tyr Ser Leu
1 5 10 15

Tyr Ala Phe Thr His Met Pro Ser Leu His Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Trp Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Asp Gly Arg Met Ser Asp Gln Thr Val Met Leu
85 90 95

Ser Glu Lys Leu Val Glu Val Ser Pro Phe Asp Ser Gly Arg Val Phe
100 105 110

Tyr Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Phe Pro Tyr Asn Ser Val Phe Gly Leu Pro Ala Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln
225 230 235 240

Ala Ile Leu Thr Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Glu Glu Phe Asp His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Ala Glu Asn Val Arg Arg Leu
340 345 350

Ala Pro Arg Phe Glu Glu Arg Leu Lys His Ile Ala Glu Arg Pro Asn
355 360 365

```
Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Glu
        435                 440                 445

Phe Ala Glu Val Ala
    450
```

<210> SEQ ID NO 77
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 77

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgtttgatgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggctttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gatttttgggg    900

ccggaactga gcaaacgtct ggaaaccgcg attgaagcga tcgaagaatt tgatcatggt    960

tttaccacac acggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgggt   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                       1362
```

<210> SEQ ID NO 78
<211> LENGTH: 453
<212> TYPE: PRT

```
<213> ORGANISM: Artificial Sequence
<220> FEATURE:
<223> OTHER INFORMATION: Engineered variant of V. fluvialis transaminase

<400> SEQUENCE: 78

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
```

385 390 395 400

Glu Arg Ile Ala Asn Thr Cys Thr Asp Leu Gly Leu Ile Cys Arg Pro
405 410 415

Leu Gly Gln Ser Val Val Leu Ala Pro Pro Tyr Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 79
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 79
atgaacaaac cgcagagctg ggaaacgcgt gcggaaacct atagcctgta tgcctttacc 60
cacatgccga gcctacatca gcgtggcacc atggtggtga cccatggcga aggcccgtat 120
atcgtggatg tgcatggccg tcgttatctg gatgcgaaca gcggcctgtg gaacatggtg 180
gcgggctttg atcataaagg cctgattgat gcggcgaaag cgcagtatga acgttttccg 240
ggctatcatg cgtttgatgg ccgtatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggctttc cgtataacag cgtgtttggc ctgccggctc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagcg ccaaaaacct aaccgcgggt ttttttccag taggagcggt gattttgggg 900
ccggaactga gcaaacgtct ggaaaccgcg attgaagcga tcgaagaatt tgatcatggt 960
tttaccacac acggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgggt 1200
gaacgtattg cgaacacctg caccgatctg ggactgattt gccgaccgct gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 80
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 80

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Asp Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Phe Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415
```

```
Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 81
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 81

```
atgaacaaac cgcagagctg ggaaacgcgt gcggaaacct atagcctgta tgcctttacc     60

cacatgccga gcctacatca gcgtggcacc atggtggtga cccatggcga aggcccgtat    120

ctggtggatg tgcatggccg tcgttatctg gatgcgaaca gcggcctgta taacatggtg    180

gcgggctttg atcataaagg cctgattgcg gcggcgaaag cgcagtatga acgttttccg    240

ggctatcatg cgttttacgg ccgtatgagc gatcagaccg tgatgctgtc tgaaaaactg    300

gtggaagtga gcccgtttcc aagcggccgt gtgttttata ccaacagcgg cagcgaagcg    360

aacgatacca tggtgaaaat gctgtggttt ctgtttcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atgaggaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gatgtggcgt aa                      1362
```

<210> SEQ ID NO 82
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 82

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
```

```
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Ala Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445
```

-continued

Phe Ala Asp Val Ala
450

<210> SEQ ID NO 83
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 83
atgaacaaac cgcagagctg ggaaacgcgt gcggaaacct atagcctgta tgcctttacc 60
cacatgccga gcctacatca gcgtggcacc atggtggtga cccatggcga aggcccgtat 120
ctggtggatg tgcatggcaa ccgttatctg gatgcgaaca gcggcctgta taacatggtg 180
gcgggctttg atcataaagg cctgattgat gcggcgaaag cgcagtatga acgttttccg 240
ggctatcatg cgttttacgg ccgtatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggccttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga ttggggaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggtaacct ggttgtgagc 1200
gaacgtattg cgaacacctg caccgatctg ggactgattt gccgaccgtt gggccagagc 1260
gtggttatcg cgccgccgta cattctgacc gaagcgcaga tggatgaaat gttcgataaa 1320
ctggaaaaag cgctggataa agtgtttgcg gaagtggcgt aa 1362

<210> SEQ ID NO 84
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 84

Met Asn Lys Pro Gln Ser Trp Glu Thr Arg Ala Glu Thr Tyr Ser Leu
1 5 10 15

Tyr Ala Phe Thr His Met Pro Ser Leu His Gln Arg Gly Thr Met Val
20 25 30

Val Thr His Gly Glu Gly Pro Tyr Leu Val Asp Val His Gly Asn Arg
35 40 45

```
Tyr Leu Asp Ala Asn Ser Gly Leu Tyr Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 85
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 85
atgaacaaac cgcagagctg ggaaacgcgt gcggaaacct atagcctgta tgcctttacc 60
cacatgccga gcctacatca gcgtggcacc atggtggtga cccatggcga aggcccgtat 120
ctggtggatg tgcatggccg tcgttatctg gatgcgaaca gcggcctgta taacatggtg 180
gcgggctttg atcataaagg cctgattgat gcggcgaaag cgcagtatga acgttttccg 240
ggctatcatg cgttttacgg ccgtatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggccttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gatttggggg 900
ccggaactga gcaaacgtct ggaaaccgcg attgaagcga ttggggaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggtaacct ggttgtgagc 1200
gaacgtattg cgaacacctg caccgatctg ggactgattt gccgaccgtt gggccagagc 1260
gtggttctgg cgccgccgta cattctgacc gaagcgcaga tggatgaaat gttcgataaa 1320
ctggaaaaag cgctggataa agtgtttgcg gaagtggcgt aa 1362

<210> SEQ ID NO 86
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 86

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Asp Ala Ala Lys Ala Gln Tyr Glu Arg Phe Pro
65                  70                  75                  80

```
Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 87
<211> LENGTH: 1362
<212> TYPE: DNA
<213> ORGANISM: Artificial Sequence
<220> FEATURE:

<223> OTHER INFORMATION: Engineered variant of V. fluvialis transaminase

<400> SEQUENCE: 87

```
atgaacaaac cgcagagctg ggaaacgcgt gcggaaacct atagcctgta tgcctttacc     60
cacatgccga gcctacatca gcgtggcacc atggtggtga cccatggcga aggcccgtat    120
ctggtggatg tgcatggccg tcgttatctg gatgcgaaca gcggcctgta taacatggtg    180
gcgggctttg atcataaagg cctgattgat gcggcgaaag cgcagtatga acgttttccg    240
ggctatcatg cgttttacgg ccgtatgagc gatcagaccg tgatgctgtc tgaaaaactg    300
gtggaagtga gcccgtttcc aagcggccgt gtgttttata ccaacagcgg cagcgaagcg    360
aacgatacca tggtgaaaat gctgtggttt ctgtttcgtg cggaaggcaa accgcagaaa    420
cgtaaaattc tgaccctgaa gaacgcgtat catggctcca ccgcggtgag cgcgagcatg    480
accggccttc cgtataacag cgtgtttggc ctgccgctgc cgggctttct gcatctgacc    540
tgcccgcatt attggcgtta tggcgaagaa ggcgaaaccg aagaacagtt tgtcgcgcgt    600
ctggcccgtg aactggaaga aaccattcag aaggaaggcg cggataccat tgcgggcttt    660
tttgcggaac cggtgatggg tgcgggcggt gttattaccc cgccaaaagg ctattttcag    720
gcgattctga ccatcctgcg caaatatgat attccggtga tcagcgatga agtgatttgc    780
ggctttggtc gtaccggcaa cacctggggc tgcgtgacct atgattttac cccggatgcg    840
attattagca gtaaaaacct aaccgcgggt ttttttccag taggagcggt gattttgggg    900
ccggaactga gcaaacgtct ggaaaccgcg attgaagcga ttggggaatt tgatcatggt    960
tttaccacag gcggccatcc ggtgggttgt gcgattgcgc tgaaagcgat tgatgtggtg   1020
atgaacgaag gcctggccga aaacgtgcgt cgtctggccc cgcgttttga agaacgtctg   1080
aaacatattg cggaacgtcc gaacattggc gaatatcgtg gtattggctt tatgtgggcg   1140
ctggaagtgg tgaaagataa agcgagcaaa gccccgtttg atccaaacct gtgggtgagc   1200
gaacgtattg cgaacacctg caccgatctg ggactgattt gccgaccgtt gggccagagc   1260
gtggttctgg cgccgccgta cattctgacg gaagcgcaga tggatgaaat gttcgataaa   1320
ctggaaaaag cgctggataa agtgtttgcg gaagtggcgt aa                      1362
```

<210> SEQ ID NO 88
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 88

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
```

-continued

```
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Pro Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 89
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 89

atgaacaaac cgcagagctg ggaaacgcgt gcggaaacct atagcctgta tgcctttacc     60
```

```
cacatgccga gcctacatca gcgtggcacc atggtggtga cccatggcga aggcccgtat    120

ctggtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttcc aagcggccgt gtgttttata ccaacagcgg cagcgaagcg    360

aacgatacca tggtgaaaat gctgtggttt ctgtttcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gatgtggcgt aa                      1362
```

<210> SEQ ID NO 90
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 90

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125
```

```
Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 91
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 91

```
atgaacaaac cgcagagctg ggaaacgcgt gcggaaacct atagcctgta tgcctttacc      60

cacatgccga gcctacatca gcgtggcacc atggtggtga cccatggcga aggcccgtat     120

ctggtggatg tgcatggccg tcgttatctg gatgcgaaca gcggcctgta taacatggtg     180
```

-continued

```
gcgggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttcc aagcggccgt gtgttttata ccaacagcgg cagcgaagcg     360

aacgatacca tggtgaaaat gctgtggttt ctgtttcgtg cggaaggcaa accgcagaaa     420

cgtaaaattc tgaccctgaa gaacgcgtat catggctcca ccgcggtgag cgcgagcatg     480

accggccttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga atggggaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gccccgtttg atggtaacct ggttgtgagc    1200

gaacgtattg cgaacacctg caccgatctg ggactgattt gccgaccgtt gggccagagc    1260

gtggttatcg cgccgccgta cattctgacc gaagcgcaga tggatgaaat gttcgataaa    1320

ctggaaaaag cgctggataa agtgtttgcg gatgtggcgt aa                       1362
```

<210> SEQ ID NO 92
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 92

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160
```

```
Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 93
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 93

```
atgaacaaac cgcagagctg ggaaacgcgt gcggaaacct atagcctgta tgcctttacc      60

cacatgccga gcctacatca gcgtggcacc atggtggtga cccatggcga aggcccgtat     120

ctggtggatg tgcatggccg tcgttatctg gatgcgaaca gcggcctgta taacatggtg     180

gcgggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttcc aagcggccgt gtgttttata ccaacagcgg cagcgaagcg     360
```

```
aacgatacca tggtgaaaat gctgtggttt ctgtttcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttatcg cgccgccgta cattctgacc gaagcgcaga tggatgaaat gttcgataaa   1320

ctggaaaaag cgctggataa agtgtttgcg gaagtggcgt aa                      1362
```

<210> SEQ ID NO 94
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 94

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
```

```
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 95
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 95

atgaacaaac cgcagagctg ggaaacgcgt gcggaaacct atagcctgta tgcctttacc      60

cacatgccga gcctacatca gcgtggcacc atggtggtga cccatggcga aggcccgtat     120

ctggtggatg tgcatggccg tcgttatctg gatgcgaaca gcggcctgta taacatggtg     180

gcgggctttg atcataaagg cctgattgcg gcggcgaaag cgcagtatga acgttttccg     240

ggctatcatg cgttttacgg ccgtatgagc gatcagaccg tgatgctgtc tgaaaaactg     300

gtggaagtga gcccgtttcc aagcggccgt gtgttttata ccaacagcgg cagcgaagcg     360

aacgatacca tggtgaaaat gctgtggttt ctgtttcgtg cggaaggcaa accgcagaaa     420

cgtaaaattc tgaccctgaa gaacgcgtat catggctcca ccgcggtgag cgcgagcatg     480
```

-continued

```
accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atgaggaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct gtgggtgagc   1200

gaacgtattg cgaacacctg caccgatctg ggactgattt gccgaccgtt gggcagcagc   1260

gtggttctgg cgccgccgta cattctgacc gaagcgcaga tggatgaaat gttcgataaa   1320

ctggaaaaag cgctggataa agtgtttgcg gaagtggcgt aa                      1362
```

```
<210> SEQ ID NO 96
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 96

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Tyr Asn Met Val Ala Gly Phe Asp
    50                  55                  60

His Lys Gly Leu Ile Ala Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Pro Ser Gly Arg Val Phe
            100                 105                 110

Tyr Thr Asn Ser Gly Ser Glu Ala Asn Asp Thr Met Val Lys Met Leu
        115                 120                 125

Trp Phe Leu Phe Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205
```

```
Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 97
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 97

```
atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660
```

```
tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atgaggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gcccgtttg atccaaacct gtgggtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gatgtggcgt aa                      1362
```

```
<210> SEQ ID NO 98
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 98

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240
```

```
Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Pro Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 99
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 99

```
atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780
```

```
ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct gttggtgagc   1200

gaacgtattg cgaacacctg caccgatctg ggactgattt gccgaccgtt gggcagcagc   1260

gtggttctgg cgccgccgta cattctgacc gaagcgcaga tggatgaaat gttcgataaa   1320

ctggaaaaag cgctggataa agtgtttgcg gaagtggcgt aa                      1362
```

<210> SEQ ID NO 100
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 100

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
```

```
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Leu Val Ser
385                 390                 395                 400

Glu Arg Ile Ala Asn Thr Cys Thr Asp Leu Gly Leu Ile Cys Arg Pro
                405                 410                 415

Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 101
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 101

atgaacaaac cgcagagctg ggaaacgcgt gcggaaacct atagcctgta tgcctttacc      60

cacatgccga gcctacatca gcgtggcacc tcagtggtaa cccatggcga aggcccgtat     120

ctggtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg cgccatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggcatcc cgtataacag cagctttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga tcgaagaatt tgatcatggt     960
```

```
tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gatgtggcgt aa                      1362
```

<210> SEQ ID NO 102
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 102

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Leu Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Ala Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Ser Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

-continued

```
Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 103
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 103

```
atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cagctttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080
```

```
aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggcagcagc   1260

gtggttctgg cgccgccgta cattctgacc gaagcgcaga tggatgaaat gttcgataaa   1320

ctggaaaaag cgctggataa agtgtttgcg gaagtggcgt aa                      1362


<210> SEQ ID NO 104
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 104

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Ser Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320
```

```
Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 105
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 105

atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atgaggaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct gtgggtgagc   1200

gaacgtattg cgaacacctg caccgatctg ggactgattt gccgaccgtt gggccagagc   1260
```

```
gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 106
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 106

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
```

```
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 107
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 107
atgaacaaac cgcagagctg ggaaacgcgt gcggaaacct atagcctgta tgcctttacc      60
cacatgccga gcctacatca gcgtggcacc tcagtggtaa cccatggcga aggcccgtat     120
atcgtggatg tgcatggccg tcgttatctg gatgcgaaca gcggcctgtt caacatggtg     180
gcgggctttg atcataaagg cctgattgat gcggcgaaag cgcagtatga acgttttccg     240
ggctatcatg cgttttacgg ccgtatgagc gatcagaccg tgatgctgtc tgaaaaactg     300
gtggaagtga gcccgtttga tagcggccgt gtgttttata ccaacagcgg cagcgaagcg     360
aacgatacca tggtgaaaat gctgtggttt ctgcatcgtg cggaaggcaa accgcagaaa     420
cgtaaaattc tgaccctgaa gaacgcgtat catggctcca ccgcggtgag cgcgagcatg     480
accggccttc cgtataacag cgtgtttggc ctgccgctgc cgggctttct gcatctgacc     540
tgcccgcatt attggcgtta tggcgaagaa ggcgaaaccg aagaacagtt tgtcgcgcgt     600
ctggcccgtg aactggaaga aaccattcag aaggaaggcg cggataccat tgcgggcttt     660
tttgcggaac cggtgatggg tgcgggcggt gttattaccc cgccaaaagg ctattttcag     720
gcgattctga ccatcctgcg caaatatgat attccggtga tcagcgatga agtgatttgc     780
ggctttggtc gtaccggcaa cacctggggc tgcgtgacct atgattttac cccggatgcg     840
attattagca gtaaaaacct aaccgcgggt ttttttccag taggagcggt gattttgggg     900
ccggaactga gcaaacgtct ggaaaccgcg attgaagcga tcgaagaatt tgatcatggt     960
tttaccacag gcggccatcc ggtgggttgt gcgattgcgc tgaaagcgat tgatgtggtg    1020
atgaacgaag gcctggccga aaacgtgcgt cgtctggccc cgcgttttga agaacgtctg    1080
aaacatattg cggaacgtcc gaacattggc gaatatcgtg gtattggctt tatgtgggcg    1140
ctggaagtgg tgaaagataa agcgagcaaa gccccgtttg atggcaacct gagcgtgagc    1200
gaacgtattg cgaacacctg caccgatctg ggactgattt gccgaccgtt gggccagagc    1260
gtggttctgg caccgccgta cattctgacc gaagcgcaga tggatgaaat gttcgataaa    1320
ctggaaaaag cgctggataa agtgtttgcg gaagtggcgt aa                       1362
```

<210> SEQ ID NO 108
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 108

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365
```

```
Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

```
<210> SEQ ID NO 109
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 109

atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag caagtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct gtgggtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gatgtggcgt aa                      1362

<210> SEQ ID NO 110
<211> LENGTH: 453
<212> TYPE: PRT
<213> ORGANISM: Artificial Sequence
```

<220> FEATURE:
<223> OTHER INFORMATION: Engineered variant of V. fluvialis transaminase

<400> SEQUENCE: 110

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Lys Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Trp Val Ser
385                 390                 395                 400
```

```
Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 111
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 111

```
atgaacaaac cgcagagctg ggaaacgcgt gcggaaaccg tgagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atgaggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gaagtggcgt aa                       1362
```

<210> SEQ ID NO 112
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 112

-continued

```
Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
```

```
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 113
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 113

atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct gttggtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gaagtggcgt aa                      1362


<210> SEQ ID NO 114
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 114

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30
```

-continued

```
Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Leu Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445
```

```
Phe Ala Glu Val Ala
    450


<210> SEQ ID NO 115
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 115

atgaacaaac cgcagagctg ggaaacgcgt gcggaaacct atagcctgta tgcctttacc     60

cacatgccga gcctacatca gcgtggcacc tcagtggtaa cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaattg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gatgtggcgt aa                      1362


<210> SEQ ID NO 116
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 116

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
```

-continued

```
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 117

-continued

<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 117

```
atgaacaaac cgcagagctg ggaaacgcgt gcggaaacct atagcctgta tgcctttacc      60

cacatgccga gcctacatca gcgtggcacc tcagtggtaa cccatggcga aggcccgtat     120

atcgtggatg tgcatggccg tcgttatctg gatgcgaaca gcggcctgtt caacatggtg     180

gcaggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggcatcc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gatttgggg      900

ccggaactga gcaaacgtct ggaaaccgcg attgaagcga ttggggaatt tgatcatggt     960

tttaccacag gcggccatcc ggtgggttgt gcgattgcgc tgaaagcgat tgatgtggtg    1020

atgaacgaag gcctgctgga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gccccgtttg atggtaacct gtgggtgagc    1200

gaacgtattg cgaacacctg caccgatctg ggactgattt gccgaccgtt gggccagagc    1260

gtggttctgg cgccgccgta cattctgacc gaagcgcaga tggatgaaat gttcgataaa    1320

ctggaaaaag cgctggataa agtgtttgcg gatgtggcgt aa                       1362
```

<210> SEQ ID NO 118
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 118

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80
```

-continued

```
Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Trp Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Asp Val Ala
    450
```

<210> SEQ ID NO 119
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 119
atgaacaaac cgcagagctg ggaaacgcgt gcggaaacct atagcctgta tgcctttacc 60
cacatgccga gcctacatca gcgtggcacc tcagtggtaa cccatggcga aggcccgtat 120
atcgtggatg tgcatggccg tcgttatctg gatgcgaaca gcggcctgtt caacatggtg 180
gcgggctttg atcataaagg cctgattgat gcggcgaaag cgcagtatga acgttttccg 240
ggctatcatg cgttttacgg ccgtatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggcatcc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga ttggggaatt tgatcatggt 960
tttaccacag gcggccatcc ggtgggttgt gcgattgcgc tgaaagcgat tgatgtggtg 1020
atgaacgaag gcctgctgga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggtaacct ggttgtgagc 1200
gaacgtattg cgaacacctg caccgatctg ggactgattt gccgaccgtt gggccagagc 1260
gtggttctgg cgccgccgta cattctgacc gaagcgcaga tggatgaaat gttcgataaa 1320
ctggaaaaag cgctggataa agtgtttgcg gaagtggcgt aa 1362

<210> SEQ ID NO 120
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 120

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
115 120 125

Trp Phe Leu His Arg Ala Glu Gly Lys Pro Gln Lys Arg Lys Ile Leu
130 135 140

Thr Leu Lys Asn Ala Tyr His Gly Ser Thr Ala Val Ser Ala Ser Met
145 150 155 160

Thr Gly Ile Pro Tyr Asn Ser Val Phe Gly Leu Pro Leu Pro Gly Phe
165 170 175

Leu His Leu Thr Cys Pro His Tyr Trp Arg Tyr Gly Glu Glu Gly Glu
180 185 190

Thr Glu Glu Gln Phe Val Ala Arg Leu Ala Arg Glu Leu Glu Glu Thr
195 200 205

Ile Gln Lys Glu Gly Ala Asp Thr Ile Ala Gly Phe Phe Ala Glu Pro
210 215 220

Val Met Gly Ala Gly Gly Val Ile Thr Pro Pro Lys Gly Tyr Phe Gln
225 230 235 240

Ala Ile Leu Thr Ile Leu Arg Lys Tyr Asp Ile Pro Val Ile Ser Asp
245 250 255

Glu Val Ile Cys Gly Phe Gly Arg Thr Gly Asn Thr Trp Gly Cys Val
260 265 270

Thr Tyr Asp Phe Thr Pro Asp Ala Ile Ile Ser Ser Lys Asn Leu Thr
275 280 285

Ala Gly Phe Phe Pro Val Gly Ala Val Ile Leu Gly Pro Glu Leu Ser
290 295 300

Lys Arg Leu Glu Thr Ala Ile Glu Ala Ile Gly Glu Phe Asp His Gly
305 310 315 320

Phe Thr Thr Gly Gly His Pro Val Gly Cys Ala Ile Ala Leu Lys Ala
325 330 335

Ile Asp Val Val Met Asn Glu Gly Leu Leu Glu Asn Val Arg Arg Leu
340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Val Val
370 375 380

Lys Asp Lys Ala Ser Lys Ala Pro Phe Asp Gly Asn Leu Val Val Ser
385 390 395 400

Glu Arg Ile Ala Asn Thr Cys Thr Asp Leu Gly Leu Ile Cys Arg Pro
405 410 415

Leu Gly Gln Ser Val Val Leu Ala Pro Pro Tyr Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 121
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 121
atgaacaaac cgcagagctg ggaaacgcgt gcggaaacct atagcctgta tgcctttacc 60

-continued

```
cacatgccga gcctacatca gcgtggcacc atggtggtga cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttgaggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct gttggtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gaagtggcgt aa                      1362
```

<210> SEQ ID NO 122
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 122

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
```

-continued

```
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Leu Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 123
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 123

atgaacaaac cgcagagctg ggaaacgcgt gcggaaacct atagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240
```

```
ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag caagtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttctgg cgccgccgta cattctgacc gaagcgcaga tggatgaaat gttcgataaa   1320

ctggaaaaag cgctggataa agtgtttgcg gaagtggcgt aa                       1362
```

<210> SEQ ID NO 124
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 124

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160
```

-continued

```
Thr Gly Leu Pro Tyr Asn Ser Lys Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

```
<210> SEQ ID NO 125
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 125

atgaacaaac cgcagagctg ggaaacgcgt gcggaaacct atagcctgta tgcctttacc      60

cacatgccga gcctacatca gcgtggcacc tcagtggtaa cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttga tagcggccgt gtgttttata ccaacagcgg cagcgaagcg     360
```

```
aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga ttggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggccagagc   1260

gtggttatcg cgccgccgta cattctgacc gaagcgcaga tggatgaaat gttcgataaa   1320

ctggaaaaag cgctggataa agtgtttgcg gaagtggcgt aa                      1362


<210> SEQ ID NO 126
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 126

Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190
```

-continued

```
Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Ile Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 127
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 127

```
atgaacaaac cgcagagctg ggaaacgcgt gcggaaacct atagcctgta tgcctttacc      60

cacatgccga gcctacatca gcgtggcacc tcagtggtaa cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggccttc cgtataacag cgtgtttggc ctgccgctgc cgggctttct gcatctgacc     540
```

```
tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga atggggaatt tgatcatggt    960

tttaccacag gcggccatcc ggtgggttgt gcgattgcgc tgaaagcgat tgatgtggtg   1020

atgaacgaag gcctgctgga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggtaacct ggttgtgagc   1200

gaacgtattg cgaacacctg caccgatctg ggactgattt gccgaccgtt gggcagcagc   1260

gtggttctgg cgccgccgta cattctgacc gaagcgcaga tggatgaaat gttcgataaa   1320

ctggaaaaag cgctggataa agtgtttgcg gaagtggcgt aa                      1362
```

<210> SEQ ID NO 128
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 128

```
Met Asn Lys Pro Gln Ser Trp Glu Thr Arg Ala Glu Thr Tyr Ser Leu
1               5                   10                  15

Tyr Ala Phe Thr His Met Pro Ser Leu His Gln Arg Gly Thr Ser Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
```

```
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Asn Gly Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Leu Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Val Val Ser
385                 390                 395                 400

Glu Arg Ile Ala Asn Thr Cys Thr Asp Leu Gly Leu Ile Cys Arg Pro
                405                 410                 415

Leu Gly Ser Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 129
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 129

```
atgaacaaac cgcagagctg ggaaacgcgt gcggaaaccg tgagcctgta tgcctttacc      60

cacatgccga gcctacgtca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgttttacgg ccgtatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggcatcc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660
```

```
tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gcccccgtttg atggcaacct gagcgtgggt   1200

gaacgtattg cgaacacctg caccgatctg ggactgattt gtcgaccgat gggccagaac   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 130
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 130

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240
```

```
Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Met Gly Gln Asn Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 131
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 131

```
atgaacaaac cgcagagctg ggaaacgcgt gcggaaaccg tgagcctgta tgcctttacc     60

cacatgccga gcctacatca gcgtggcacc atggtggtaa cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccggctc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840
```

```
attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgggt   1200

gaacgtattg cgaacacctg caccgatctg ggactgattt gtcgaccgct gggccagaac   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 132
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 132

```
Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

```
Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Asn Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 133
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 133

```
atgaacaaac cgcagagctg ggaaacgcgt gcggaaaccg tgagcctgta tgcctttacc     60

cacatgccga gcctacatca gcgtggcacc atggtggtaa cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgcatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960
```

```
tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg tgccgccgta cattctgacc gaagcgcaga tggatgaaat gttcgataaa   1320

ctggaaaaag cgctggataa agtgtttgcg gaagtggcgt aa                      1362


<210> SEQ ID NO 134
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 134

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
```

-continued

```
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Val Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 135
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 135

atgaacaaac cgcagagctg ggaaacgcgt gcggaaaccg tgagcctgta tgcctttacc     60

cacatgccga gcctacatca gcgtggcacc atggtggtaa cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg cctgatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacac acggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140
```

```
ctggaagtgg tgaaagataa agcgagcaaa gccccgtttg atggcaacct gagcgtgggt   1200

gaacgtattg cgaacacctg caccgatctg ggactgattt gtcgaccgat gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 136
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 136

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320
```

```
Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Met Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450


<210> SEQ ID NO 137
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 137

atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtt caacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcacgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgagc   1200

gaacgtattg cgaacacctg caccgatctg ggactgattt gccgaccgtt gggccagagc   1260
```

-continued

```
gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 138
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 138

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350
```

-continued

```
Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

```
<210> SEQ ID NO 139
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 139

atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagccg tgaaagataa agcgagcaaa gccccgtttg atggcaacct gagcgtgggt   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 140
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 140

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
```

```
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 141
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 141

```
atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgcatgagc gatcagaccg tgatgctgtc tgaaaaactg    300

gtggaagtga gcccgtttga tagcggccgt gtgtttctga ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagca gtaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagccg tgaaagataa agcgagcaaa gccccgtttg atggcaacct gagcgtgagc   1200

gaacgtattg cgaacacctg caccgatctg ggactgattt gccgaccgtt gggccagagc   1260

gtggttctgg tgccgccgta cattctgacc gaagcgcaga tggatgaaat gttcgataaa   1320

ctggaaaaag cgctggataa agtgtttgcg gaagtggcgt aa                      1362
```

<210> SEQ ID NO 142
<211> LENGTH: 453
<212> TYPE: PRT
<213> ORGANISM: Artificial Sequence
<220> FEATURE:

<223> OTHER INFORMATION: Engineered variant of V. fluvialis transaminase

<400> SEQUENCE: 142

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Ser
385                 390                 395                 400
```

-continued

```
Glu Arg Ile Ala Asn Thr Cys Thr Asp Leu Gly Leu Ile Cys Arg Pro
                405                 410                 415

Leu Gly Gln Ser Val Val Leu Val Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 143
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 143

```
atgaacaaac cgcagagctg ggaaacgcgt gcggaaacct atagcctgta tgcctttacc      60

cacatgccga gcctacatca gcgtggcacc atggtggtga cccatggcga aggcccgtat     120

atcgtggatg tgcatggccg tcgttatctg gatgcgaaca gcggcctgtg gaacatggtg     180

gcgggctttg atcataaagg cctgattgat gcggcgaaag cgcagtatga acgttttccg     240

ggctatcatg cgttttacgg cctgatgagc gatcagaccg tgatgctgtc tgaaaaactg     300

gtggaagtga gcccgtttga tagcggccgt gtgttttata ccaacagcgg cagcgaagcg     360

aacgatacca tggtgaaaat gctgtggttt ctgcatcgtg cggaaggcaa accgcagaaa     420

cgtaaaattc tgaccctgaa gaacgcgtat catggctcca ccgcggtgag cgcgagcatg     480

accggccttc cgtataacag cgtgtttggc ctgccgctgc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga tcgaagaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagtgg tgaaagataa agcgagcaaa gccccgtttg atggcaacct gagcgtgagc    1200

gaacgtattg cgaacacctg caccgatctg ggactgattt gccgaccgtt gggccagagc    1260

gtggttctgg caccgccgta cattctgacc gaagcgcaga tggatgaaat gttcgataaa    1320

ctggaaaaag cgctggataa agtgtttgcg gaagtggcgt aa                       1362
```

<210> SEQ ID NO 144
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 144

```
Met Asn Lys Pro Gln Ser Trp Glu Thr Arg Ala Glu Thr Tyr Ser Leu
```

-continued

```
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430
```

```
Gln Met Asp Glu Met Phe Asp Lys Leu Glu Lys Ala Leu Asp Lys Val
        435                 440                 445

Phe Ala Glu Val Ala
    450


<210> SEQ ID NO 145
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 145

atgaacaaac cgcagagctg ggaaacgcgt gcggaaaccg tgagcctgta tgcctttacc     60

cacatgccga gcctacgtca gcgtggcacc atggtggtga cccatggcga aggcccgtat    120

atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gcaggcgtat catggctcca ccgcggtgag cgcgagcatg    480

accggcatcc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960

tttaccacag gcggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagccg tgaaagataa agcgagcaaa gccccgtttg atggcaacct gagcgtgggt   1200

gaacgtattg cgaacacctg caccgatctg ggactgattt gtcgaccgct gggccagaac   1260

gtggttctgg caccgccgta cattctgacc gaagcgcaga tggatgaaat gttcgataaa   1320

ctggaaaaag cgctggataa agtgtttgcg gaagtggcgt aa                      1362


<210> SEQ ID NO 146
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 146

Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30
```

-continued

```
Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Asn Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
```

450

<210> SEQ ID NO 147
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 147
atgaacaaac cgcagagctg ggaaacgcgt gcggaaaccg tgagcctgta tgcctttacc 60
cacatgccga gcctacatca gcgtggcacc atggtgacca cccatggcga aggcccgtat 120
atcgtggatg tgcatggccg tcgttatctg gatgcgaaca gcggcctgtt caacatggtg 180
gcgggctttg atcataaagg cctgattgat gcggcgaaag cgcagtatga acgttttccg 240
ggctatcatg cgttttacgg ccgtatgagc gatcagaccg tgatgctgtc tgaaaaactg 300
gtggaagtga gcccgtttga tagcggccgt gtgtttctga ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggccttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 148
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 148

Met Asn Lys Pro Gln Ser Trp Glu Thr Arg Ala Glu Thr Val Ser Leu
1 5 10 15

Tyr Ala Phe Thr His Met Pro Ser Leu His Gln Arg Gly Thr Met Val
20 25 30

Thr Thr His Gly Glu Gly Pro Tyr Ile Val Asp Val His Gly Arg Arg
35 40 45

Tyr Leu Asp Ala Asn Ser Gly Leu Phe Asn Met Val Ala Gly Phe Asp
50 55 60

```
His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 149
<211> LENGTH: 1362

```
<212> TYPE: DNA
<213> ORGANISM: Artificial Sequence
<220> FEATURE:
<223> OTHER INFORMATION: Engineered variant of V. fluvialis transaminase

<400> SEQUENCE: 149

atgaacaaac cgcagagctg ggaaacgcgt gcggaaaccg tgagcctgta tgcctttacc      60

cacatgccga gcctacatca gcgtggcacc atggtggtaa cccatggcga aggcccgtat     120

atcgtggatg tgcatggccg tcgttatctg gatgcgaaca gcggcctgtt caacatggtg     180

gcgggctttg atcataaagg cctgattgat gcggcgaaag cgcagtatga acgttttccg     240

ggctatcatg cgttttacgg cctgatgagc gatcagaccg tgatgctgtc tgaaaaactg     300

gtggaagtga gcccgtttga tagcggccgt gtgtttctga ccaacagcgg cagcgaagcg     360

aacgatacca tggtgaaaat gctgtggttt ctgcatcgtg cggaaggcaa accgcagaaa     420

cgtaaaattc tgaccctgaa gcaggcgtat catggctcca ccgcggtgag cgcgagcatg     480

accggcatcc cgtataacag cgtgtttggc ctgccggctc cgggctttct gcatctgacc     540

tgcccgcatt attggcgtta tggcgaagaa ggcgaaaccg aagaacagtt tgtcgcgcgt     600

ctggcccgtg aactggaaga aaccattcag aaggaaggcg cggataccat tgcgggcttt     660

tttgcggaac cggtgatggg tgcgggcggt gttattaccc cgccaaaagg ctattttcag     720

gcgattctga ccatcctgcg caaatatgat attccggtga tcagcgatga agtgatttgc     780

ggctttggtc gtaccggcaa cacctggggc tgcgtgacct atgattttac cccggatgcg     840

attattagca gtaaaaacct aaccgcgggt ttttttccag taggagcggt gattttgggg     900

ccggaactga gcaaacgtct ggaaaccgcg attgaagcga tcgaagaatt tgatcatggt     960

tttaccacag gcggccatcc ggtgggttgt gcgattgcgc tgaaagcgat tgatgtggtg    1020

atgaacgaag gcctggccga aaacgtgcgt cgtctggccc cgcgttttga agaacgtctg    1080

aaacatattg cggaacgtcc gaacattggc gaatatcgtg gtattggctt tatgtgggcg    1140

ctggaagccg tgaaagataa agcgagcaaa gccccgtttg atggcaacct gagcgtgggt    1200

gaacgtattg cgaacacctg caccgatctg ggactgattt gccgaccgtt gggccagagc    1260

gtggttctgg caccgccgta cattctgacc gaagcgcaga tggatgaaat gttcgataaa    1320

ctggaaaaag cgctggataa agtgtttgcg gaagtggcgt aa                       1362


<210> SEQ ID NO 150
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 150

Met Asn Lys Pro Gln Ser Trp Glu Thr Arg Ala Glu Thr Val Ser Leu
1               5                   10                  15

Tyr Ala Phe Thr His Met Pro Ser Leu His Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Phe Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Leu Met Ser Asp Gln Thr Val Met Leu
```

```
                85                  90                  95

Ser Glu Lys Leu Val Glu Val Ser Pro Phe Asp Ser Gly Arg Val Phe
            100                 105                 110

Leu Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Gln Ala Tyr His Gly Ser Thr Ala Val Ser Ala Ser Met
145                 150                 155                 160

Thr Gly Ile Pro Tyr Asn Ser Val Phe Gly Leu Pro Ala Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 151
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 151
atgaacaaac cgcagagctg ggaaacgcgt gcggaaacct atagcctgta tgcctttacc 60
cacatgccga gcctacatca gcgtggcacc atggtggtga cccatggcga aggcccgtat 120
atcgtggatg tgcatggccg tcgttatctg gatgcgaaca gcggcctgtt caacatggtg 180
gcgggctttg atcataaagg cctgattgat gcggcgaaag cgcagtatga acgttttccg 240
ggctatcatg cgttttacgg ccgtatgagc gatcagaccg tgatgctgtc tgaaaaactg 300
gtggaagtga gcccgtttga tagcggccgt gtgttttata ccaacagcgg cagcgaagcg 360
aacgatacca tggtgaaaat gctgtggttt ctgcatcgtg cggaaggcaa accgcagaaa 420
cgtaaaattc tgaccctgaa gaacgcgtat catggctcca ccgcggtgag cgcgagcatg 480
accggccttc cgtataacag cgtgtttggc ctgccgctgc cgggctttct gcatctgacc 540
tgcccgcatt attggcgtta tggcgaagaa ggcgaaaccg aagaacagtt tgtcgcgcgt 600
ctggcccgtg aactggaaga aaccattcag aaggaaggcg cggataccat tgcgggcttt 660
tttgcggaac cggtgatggg tgcgggcggt gttattaccc cgccaaaagg ctattttcag 720
gcgattctga ccatcctgcg caaatatgat attccggtga tcagcgatga agtgatttgc 780
ggctttggtc gtaccggcaa cacctggggc tgcgtgacct atgattttac cccggatgcg 840
attattagca gtaaaaacct aaccgcgggt ttttttccag taggagcggt gattttgggg 900
ccggaactga gcaaacgtct ggaaaccgcg attgaagcga tcgaagaatt tgatcatggt 960
tttaccacag gcggccatcc ggtgggttgt gcgattgcgc tgaaagcgat tgatgtggtg 1020
atgaacgaag gcctggccga aaacgtgcgt cgtctggccc cgcgttttga agaacgtctg 1080
aaacatattg cggaacgtcc gaacattggc gaatatcgtg gtattggctt tatgtgggcg 1140
ctggaagtgg tgaaagataa agcgagcaaa gccccgtttg atggcaacct gagcgtgagc 1200
gaacgtattg cgaacacctg caccgatctg ggactgattt gccgaccgtt gggccagagc 1260
gtggttctgg caccgccgta cattctgacc gaagcgcaga tggatgaaat gttcgataaa 1320
ctggaaaaag cgctggataa agtgtttgcg gaagtggcgt aa 1362

<210> SEQ ID NO 152
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 152

Met Asn Lys Pro Gln Ser Trp Glu Thr Arg Ala Glu Thr Tyr Ser Leu
1 5 10 15

Tyr Ala Phe Thr His Met Pro Ser Leu His Gln Arg Gly Thr Met Val
20 25 30

Val Thr His Gly Glu Gly Pro Tyr Ile Val Asp Val His Gly Arg Arg
35 40 45

Tyr Leu Asp Ala Asn Ser Gly Leu Phe Asn Met Val Ala Gly Phe Asp
50 55 60

His Lys Gly Leu Ile Asp Ala Ala Lys Ala Gln Tyr Glu Arg Phe Pro
65 70 75 80

Gly Tyr His Ala Phe Tyr Gly Arg Met Ser Asp Gln Thr Val Met Leu
85 90 95

Ser Glu Lys Leu Val Glu Val Ser Pro Phe Asp Ser Gly Arg Val Phe
100 105 110

```
Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140

Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr Gly Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 153
<211> LENGTH: 1362
<212> TYPE: DNA
<213> ORGANISM: Artificial Sequence
<220> FEATURE:
<223> OTHER INFORMATION: Engineered variant of V. fluvialis transaminase

<400> SEQUENCE: 153

```
atgaacaaac cgcagagctg ggaaacgcgt gcggaaaccg tgagcctgta tgcctttacc      60

cacatgccga gcctacgtca gcgtggcacc atggtggtga cccatggcga aggcccgtat     120
```

```
atcgtggatg tgcatggccg tcgttatctg gatgcgaaca gcggcctgtg gaacatggtg    180

gcgggctttg atcataaagg cctgattgat gcggcgaaag cgcagtatga acgttttccg    240

ggctatcatg cgttttacgg ccgtatgagc gatcagaccg tgatgctgtc tgaaaaactg    300

gtggaagtga gcccgtttga tagcggccgt gtgttttata ccaacagcgg cagcgaagcg    360

aacgatacca tggtgaaaat gctgtggttt ctgcatcgtg cggaaggcaa accgcagaaa    420

cgtaaaattc tgaccctgaa gaacgcgtat catggctcca ccgcggtgag cgcgagcatg    480

accggccttc cgtataacag cgtgtttggc ctgccgctgc cgggctttct gcatctgacc    540

tgcccgcatt attggcgtta tggcgaagaa ggcgaaaccg aagaacagtt tgtcgcgcgt    600

ctggcccgtg aactggaaga aaccattcag aaggaaggcg cggataccat tgcgggcttt    660

tttgcggaac cggtgatggg tgcgggcggt gttattaccc cgccaaaagg ctattttcag    720

gcgattctga ccatcctgcg caaatatgat attccggtga tcagcgatga agtgatttgc    780

ggctttggtc gtaccggcaa cacctggggc tgcgtgacct atgattttac cccggatgcg    840

attattagcg ccaaaaacct aaccgcgggt ttttttccag taggagcggt gattttgggg    900

ccggaactga gcaaacgtct ggaaaccgcg attgaagcga tcgaagaatt tgatcatggt    960

tttaccacac acggccatcc ggtgggttgt gcgattgcgc tgaaagcgat tgatgtggtg   1020

atgaacgaag gcctggccga aaacgtgcgt cgtctggccc cgcgttttga agaacgtctg   1080

aaacatattg cggaacgtcc gaacattggc gaatatcgtg gtattggctt tatgtgggcg   1140

ctggaagtgg tgaaagataa agcgagcaaa gccccgtttg atggcaacct gagcgtgggt   1200

gaacgtattg cgaacacctg caccgatctg ggactgattt gccgaccgtt gggccagagc   1260

gtggttctgg caccgccgta cattctgacc gaagcgcaga tggatgaaat gttcgataaa   1320

ctggaaaaag cgctggataa agtgtttgcg gaagtggcgt aa                      1362
```

<210> SEQ ID NO 154
<211> LENGTH: 453
<212> TYPE: PRT
<213> ORGANISM: Artificial Sequence
<220> FEATURE:
<223> OTHER INFORMATION: Engineered variant of V. fluvialis transaminase

<400> SEQUENCE: 154

```
Met Asn Lys Pro Gln Ser Trp Glu Thr Arg Ala Glu Thr Val Ser Leu
1               5                   10                  15

Tyr Ala Phe Thr His Met Pro Ser Leu Arg Gln Arg Gly Thr Met Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Tyr Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Arg Ala Glu Gly Lys Pro Gln Lys Arg Lys Ile Leu
    130                 135                 140
```

-continued

```
Thr Leu Lys Asn Ala Tyr His Gly Ser Thr Ala Val Ser Ala Ser Met
145                 150                 155                 160

Thr Gly Leu Pro Tyr Asn Ser Val Phe Gly Leu Pro Leu Pro Gly Phe
                165                 170                 175

Leu His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Lys Glu Gly Ala Asp Thr Ile Ala Gly Phe Phe Ala Glu Pro
    210                 215                 220

Val Met Gly Ala Gly Gly Val Ile Thr Pro Pro Lys Gly Tyr Phe Gln
225                 230                 235                 240

Ala Ile Leu Thr Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ala Lys Asn Leu Thr
        275                 280                 285

Ala Gly Phe Phe Pro Val Gly Ala Val Ile Leu Gly Pro Glu Leu Ser
    290                 295                 300

Lys Arg Leu Glu Thr Ala Ile Glu Ala Ile Glu Glu Phe Asp His Gly
305                 310                 315                 320

Phe Thr Thr His Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Val Val
    370                 375                 380

Lys Asp Lys Ala Ser Lys Ala Pro Phe Asp Gly Asn Leu Ser Val Gly
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Ala Pro Pro Tyr Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```